US012668632B2

(12) United States Patent
Murphy et al.

(10) Patent No.: US 12,668,632 B2
(45) Date of Patent: *Jun. 30, 2026

(54) BISPECIFIC ANTI-MUC16 X ANTI-CD28 ANTIBODIES AND USES THEREOF

(71) Applicant: Regeneron Pharmaceuticals, Inc., Tarrytown, NY (US)

(72) Inventors: Andrew J. Murphy, Croton-on-Hudson, NY (US); Dimitris Skokos, New York, NY (US); Janelle Waite, Bronx, NY (US); Erica Ullman, Yorktown Heights, NY (US); Aynur Hermann, New York, NY (US); Eric Smith, New York, NY (US); Lauric Haber, Rye Brook, NY (US); George D. Yancopoulos, Yorktown Heights, NY (US); Alison Crawford, Dobbs Ferry, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 121 days.

This patent is subject to a terminal disclaimer.

(21) Appl. No.: 17/890,078

(22) Filed: Aug. 17, 2022

(65) Prior Publication Data
US 2023/0279113 A1    Sep. 7, 2023

Related U.S. Application Data

(63) Continuation of application No. 16/719,273, filed on Dec. 18, 2019, now Pat. No. 11,453,721.

(60) Provisional application No. 62/815,861, filed on Mar. 8, 2019, provisional application No. 62/782,142, filed on Dec. 19, 2018.

(51) Int. Cl.
| | |
|---|---|
| *C07K 16/28* | (2006.01) |
| *A61K 39/00* | (2006.01) |
| *A61K 39/395* | (2006.01) |
| *A61P 35/00* | (2006.01) |
| *C07K 16/30* | (2006.01) |

(52) U.S. Cl.
CPC ...... *C07K 16/2818* (2013.01); *A61K 39/3955* (2013.01); *A61P 35/00* (2018.01); *C07K 16/2809* (2013.01); *C07K 16/3092* (2013.01); *A61K 2039/507* (2013.01); *C07K 2317/24* (2013.01); *C07K 2317/565* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 11,453,721 B2 * | 9/2022 | Murphy | ............ C07K 16/3069 |
| 2014/0099254 A1 | 4/2014 | Chang et al. | |
| 2017/0224818 A1 | 8/2017 | Lindhoffer et al. | |

FOREIGN PATENT DOCUMENTS

| | | | | |
|---|---|---|---|---|
| WO | WO-2010151792 A1 * | 12/2010 | .......... | A61K 39/395 |
| WO | 2015/03666 A1 | 3/2015 | | |
| WO | 18/067331 A1 | 4/2018 | | |

OTHER PUBLICATIONS

Chames et al., "Bispecific antibodies for cancer therapy The light at the end of the tunnel?," Landes Bioscience Review, vol. 1(No. 6): 539-547, (2009). [<URL: www.landesbioscience.com>].

Dondelinger et al., "Understanding the Significance and Implications of Antibody Numbering and Antigen-Binding Surface/Residue Definition," Frontiers in Immunology, vol. 9:1-15, (2016).

Koneru et al., "A phase I clinical trial of adoptive T cell therapy using IL-12 secreting MUC-16ecto directed chimeric antigen receptors for recurrent ovarian cancer," Journal of Translational Medicine, vol. 13:102:1-11, (2015). [DOI 10.1186/s12967-015-0460-x].

Renner, et al., "Cure of Xenografted Human Tumors by Bispecific Monoclonal Antibodies and Human T Cells," Science, vol. 264: 883-835, (1994).

Skokos et al., "A class of costimulatory CD28-bispecific antibodies that enhance the antitumor activity of CD3-bispecific antibodies," Science Translational Medicine: Research Article, vol. 12:1-14, (2020).

Smith et al., "A novel, native-format bispecific antibody triggering T-cell killing of B-cells is robustly active in mouse tumor models and cynomolgus monkeys," Scientific Reports, 17943:1-12, (2015).

U.S. Appl. No. 16/719,273, Requirement for Restriction/Election mailed Sep. 21, 2021.

U.S. Appl. No. 16/719,273, Non-Final Office Action mailed Dec. 16, 2021.

U.S. Appl. No. 16/719,273, Notice of Allowance mailed May 18, 2022.

WIPO Application No. PCT/US2019/067109, PCT International Search Report and Written Opinion of the International Searching Authority mailed Mar. 11, 2020.

Zhukovsky et al., "Bispecific antibodies and CARs: generalized immunotherapeutics harnessing T cell redirection," ScienceDirect: Current Opinion in Immunology, vol. 40:24-35, (2016).

(Continued)

*Primary Examiner* — Gregory S Emch
*Assistant Examiner* — Sarah A Alsomairy
(74) *Attorney, Agent, or Firm* — Schwabe, Williamson & Wyatt PC; Aparna Patankar

(57) ABSTRACT

The present invention provides bispecific antigen-binding molecules comprising a first antigen-binding domain that specifically binds human CD28, and a second antigen-binding molecule that specifically binds human MUC16. In certain embodiments, the bispecific antigen-binding molecules of the present invention are capable of inhibiting the growth of tumors expressing MUC16, such as ovarian tumors. The antibodies and bispecific antigen-binding molecules of the invention are useful for the treatment of diseases and disorders in which an up-regulated or induced targeted immune response is desired and/or therapeutically beneficial.

26 Claims, 24 Drawing Sheets

Specification includes a Sequence Listing.

(56) References Cited

OTHER PUBLICATIONS

U.S. Appl. No. 62/782,142, filed Dec. 19, 2018, Expired.
U.S. Appl. No. 62/815,861, filed Mar. 8, 2019, Expired.
PCT/US2019/067109, Dec. 18, 2019, WO 2020/132024, Published.
U.S. Appl. No. 16/719,273, filed Dec. 18, 2019, U.S. Pat. No. 11,453,721, Issued.

* cited by examiner

MC38     EL4     B16F10.9

TARGET CELLS: OVARIAN CANCER LINE PEO-1 (ENDOGENOUS MUC16+)

MUC16xCD3 ALONE

MUC16xCD3
+MUC16xCD28 (2.5 µg/ml)

─●─    MUC16xCD3 + MUC16xCD28

─○─    MUC16xCD3

─■─    NONTARGETxCD3 + MUC16xCD28

─⊟─    NONTARGETxCD3

TUMOR CELL KILL

IFNγ

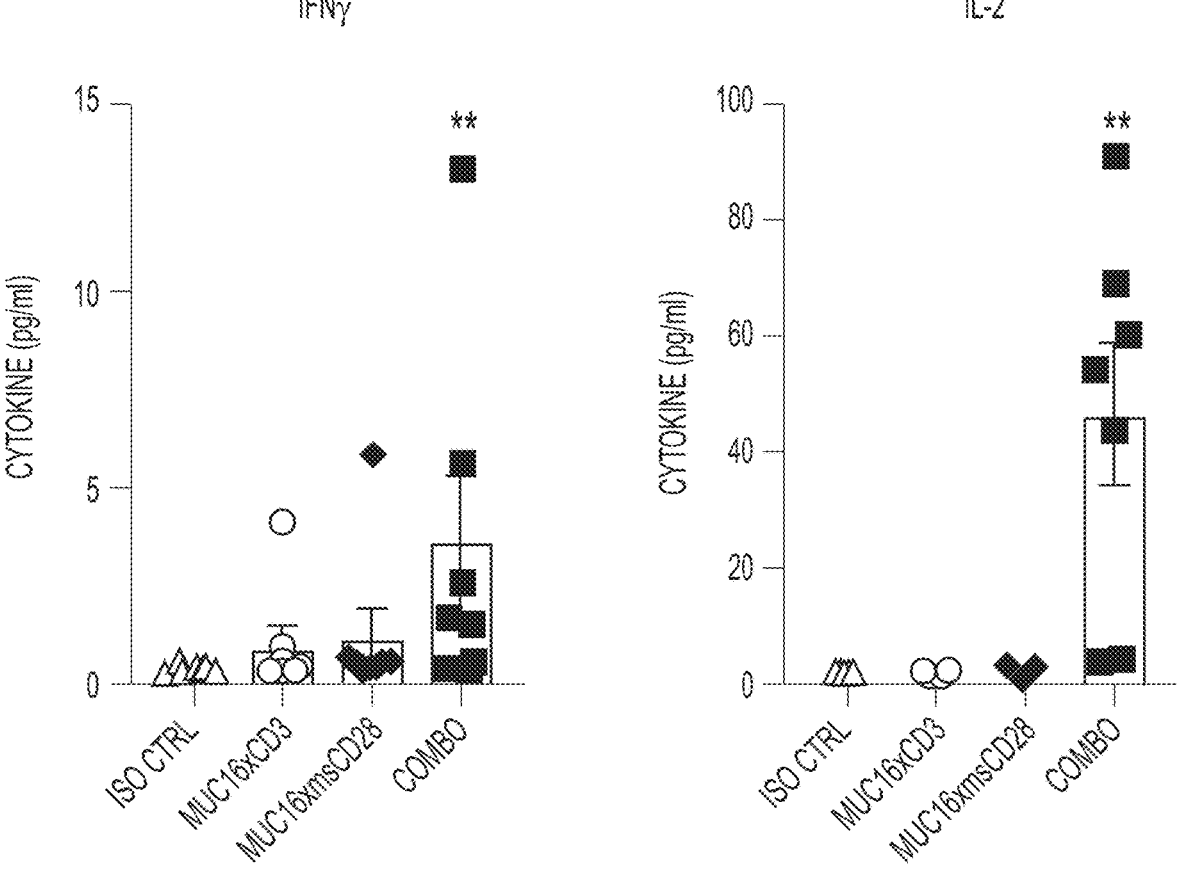
FIG. 6C           FIG. 6D

SEQUENCE LISTING

Sequence total quantity: 54
SEQ ID NO: 1              moltype = DNA   length = 387
FEATURE                  Location/Qualifiers
misc_feature             1..387
                         note = synthetic
source                   1..387
                         mol_type = other DNA
                         organism = synthetic construct
SEQUENCE: 1
gaggtgcagc tggtggagtc tggggggaggc ttggaacagc cagggcggtc cctgagactc   60
tcctgtacag cttctggatt cgcctttggt gatcatacta tgagctgggt ccgccaggct   120
ccagggaagg ggctggagtg ggtaggtttc attagaagta gagcttatgg tgggacaaca   180
gaatacgccg cgtctgtgaa aggcagattc accatctcaa gagatgattc caaaagcatc   240
gcctatctgc aaatggacag cctgaaaacc gaggacacac ccgtgtatta ttgtactagc   300
gggggatatg atagtagtct tcattactac tattactacc acggtatgga cgtctggggc   360
cgagggacca cggtcaccgt ctcctca                                       387

SEQ ID NO: 2              moltype = AA   length = 129
FEATURE                  Location/Qualifiers
REGION                   1..129
                         note = synthetic
source                   1..129
                         mol_type = protein
                         organism = synthetic construct
SEQUENCE: 2
EVQLVESGGG LEQPGRSLRL SCTASGFAFG DHTMSWVRQA PGKGLEWVGF IRSRAYGGTT   60
EYAASVKGRF TISRDDSKSI AYLQMDSLKT EDTAVYYCTS GGYDSSLHYY YYYHGMDVWG   120
RGTTVTVSS                                                           129

SEQ ID NO: 3              moltype = DNA   length = 24
FEATURE                  Location/Qualifiers
misc_feature             1..24
                         note = synthetic
source                   1..24
                         mol_type = other DNA
                         organism = synthetic construct
SEQUENCE: 3
ggattcgcct ttggtgatca tact                                          24

SEQ ID NO: 4              moltype = AA   length = 8
FEATURE                  Location/Qualifiers
REGION                   1..8
                         note = synthetic
source                   1..8
                         mol_type = protein
                         organism = synthetic construct
SEQUENCE: 4
GFAFGDHT                                                             8

SEQ ID NO: 5              moltype = DNA   length = 30
FEATURE                  Location/Qualifiers
misc_feature             1..30
                         note = synthetic
source                   1..30
                         mol_type = other DNA
                         organism = synthetic construct
SEQUENCE: 5
attagaagta gagcttatgg tgggacaaca                                    30

SEQ ID NO: 6              moltype = AA   length = 10
FEATURE                  Location/Qualifiers
REGION                   1..10
                         note = synthetic
source                   1..10

-continued

```
                        mol_type = protein
                        organism = synthetic construct
SEQUENCE: 6
IRSRAYGGTT                                                         10

SEQ ID NO: 7           moltype = DNA   length = 60
FEATURE                Location/Qualifiers
misc_feature           1..60
                        note = synthetic
source                 1..60
                        mol_type = other DNA
                        organism = synthetic construct
SEQUENCE: 7
actagcgggg gatatgatag tagtcttcat tactactatt actaccacgg tatggacgtc   60

SEQ ID NO: 8           moltype = AA   length = 20
FEATURE                Location/Qualifiers
REGION                 1..20
                        note = synthetic
source                 1..20
                        mol_type = protein
                        organism = synthetic construct
SEQUENCE: 8
TSGGYDSSLH YYYYYHGMDV                                               20

SEQ ID NO: 9           moltype = DNA   length = 324
FEATURE                Location/Qualifiers
misc_feature           1..324
                        note = synthetic
source                 1..324
                        mol_type = other DNA
                        organism = synthetic construct
SEQUENCE: 9
gaaattgtgt tgacgcagtc tccaggcacc ctgtctttgt ctccagggga aagagccacc   60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcaccttg gacgttcggc  300
caagggacca aggtggaaat caaa                                        324

SEQ ID NO: 10          moltype = AA   length = 108
FEATURE                Location/Qualifiers
REGION                 1..108
                        note = synthetic
source                 1..108
                        mol_type = protein
                        organism = synthetic construct
SEQUENCE: 10
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QYGSSPWTFG QGTKVEIK               108

SEQ ID NO: 11          moltype = DNA   length = 21
FEATURE                Location/Qualifiers
misc_feature           1..21
                        note = synthetic
source                 1..21
                        mol_type = other DNA
                        organism = synthetic construct
SEQUENCE: 11
cagagtgtta gcagcagcta c                                            21

SEQ ID NO: 12          moltype = AA   length = 7
FEATURE                Location/Qualifiers
REGION                 1..7
                        note = synthetic
source                 1..7
                        mol_type = protein
                        organism = synthetic construct
SEQUENCE: 12
QSVSSSY                                                            7

SEQ ID NO: 13          moltype =    length =
SEQUENCE: 13
000

SEQ ID NO: 14          moltype =    length =
SEQUENCE: 14
000
```

```
SEQ ID NO: 15           moltype = DNA  length = 27
FEATURE                 Location/Qualifiers
misc_feature            1..27
                        note = synthetic
source                  1..27
                        mol_type = other DNA
                        organism = synthetic construct
SEQUENCE: 15
cagcagtatg gtagctcacc ttggacg                                      27

SEQ ID NO: 16           moltype = AA  length = 9
FEATURE                 Location/Qualifiers
REGION                  1..9
                        note = synthetic
source                  1..9
                        mol_type = protein
                        organism = synthetic construct
SEQUENCE: 16
QQYGSSPWT                                                          9

SEQ ID NO: 17           moltype = DNA  length = 366
FEATURE                 Location/Qualifiers
misc_feature            1..366
                        note = synthetic
source                  1..366
                        mol_type = other DNA
                        organism = synthetic construct
SEQUENCE: 17
caggtgcagc tgcaggagtc gggcccagga ctggtgaagc cttcggagac cctgtccctc   60
acctgcactg tctctggtgg ctccatcagt agttactact ggagctggat ccggcagccc   120
ccagggaagg gactggagtg gattgggtat atctattaca gtgggatcac ccactacaac   180
ccctccctca agagtcgagt caccatatca gtagacacgt ccaagatcca gttctccctg   240
aagctgagtt ctgtgaccgc tgcggacacg gccgtgtatt actgtgcgag atggggggtt   300
cggagggact actactacta cggtatggac gtctggggcc aagggaccac ggtcaccgtc   360
tcctca                                                            366

SEQ ID NO: 18           moltype = AA  length = 122
FEATURE                 Location/Qualifiers
REGION                  1..122
                        note = synthetic
source                  1..122
                        mol_type = protein
                        organism = synthetic construct
SEQUENCE: 18
QVQLQESGPG LVKPSETLSL TCTVSGGSIS SYYWSWIRQP PGKGLEWIGY IYYSGITHYN   60
PSLKSRVTIS VDTSKIQFSL KLSSVTAADT AVYYCARWGV RRDYYYYGMD VWGQGTTVTV   120
SS                                                                122

SEQ ID NO: 19           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 19
ggtggctcca tcagtagtta ctac                                        24

SEQ ID NO: 20           moltype = AA  length = 8
FEATURE                 Location/Qualifiers
REGION                  1..8
                        note = synthetic
source                  1..8
                        mol_type = protein
                        organism = synthetic construct
SEQUENCE: 20
GGSISSYY                                                          8

SEQ ID NO: 21           moltype = DNA  length = 21
FEATURE                 Location/Qualifiers
misc_feature            1..21
                        note = synthetic
source                  1..21
                        mol_type = other DNA
                        organism = synthetic construct
SEQUENCE: 21
atctattaca gtgggatcac c                                           21

SEQ ID NO: 22           moltype = AA  length = 7
```

-continued

```
FEATURE                 Location/Qualifiers
REGION                  1..7
                        note = synthetic
source                  1..7
                        mol_type = protein
                        organism = synthetic construct
SEQUENCE: 22
IYYSGIT                                                          7

SEQ ID NO: 23           moltype = DNA   length = 48
FEATURE                 Location/Qualifiers
misc_feature            1..48
                        note = synthetic
source                  1..48
                        mol_type = other DNA
                        organism = synthetic construct
SEQUENCE: 23
gcgagatggg gggttcggag ggactactac tactacggta tggacgtc             48

SEQ ID NO: 24           moltype = AA   length = 16
FEATURE                 Location/Qualifiers
REGION                  1..16
                        note = synthetic
source                  1..16
                        mol_type = protein
                        organism = synthetic construct
SEQUENCE: 24
ARWGVRRDYY YYGMDV                                                16

SEQ ID NO: 25           moltype = DNA   length = 360
FEATURE                 Location/Qualifiers
misc_feature            1..360
                        note = synthetic
source                  1..360
                        mol_type = other DNA
                        organism = synthetic construct
SEQUENCE: 25
caggtgcagc tggtggagtc tggggggaggc ttggtcaagc ctggagggtc cctgagactc  60
tcctgtgcag cctctggatt caccttccgt gactactcca tgagctggat ccgccaggct  120
ccagggaagg ggctggagtg ggtttcatac gttactttttt ttaatagtgc catatactac  180
gcagactctg tgaagggccg attcaccatc tccaggggaca acgccaagaa ctcactgtat  240
ctgcaaatga acagcctgag agccgaggac acggccgtat attactgtgc gagagaaaga  300
gagcctattg tggggggctt tgactactgg ggccagggaa ccctggtcac cgtctcctca  360

SEQ ID NO: 26           moltype = AA   length = 120
FEATURE                 Location/Qualifiers
REGION                  1..120
                        note = synthetic
source                  1..120
                        mol_type = protein
                        organism = synthetic construct
SEQUENCE: 26
QVQLVESGGG LVKPGGSLRL SCAASGFTFR DYSMSWIRQA PGKGLEWVSY VTFFNSAIYY  60
ADSVKGRFTI SRDNAKNSLY LQMNSLRAED TAVYYCARER EPIVGGFDYW GQGTLVTVSS  120

SEQ ID NO: 27           moltype = DNA   length = 24
FEATURE                 Location/Qualifiers
misc_feature            1..24
                        note = synthetic
source                  1..24
                        mol_type = other DNA
                        organism = synthetic construct
SEQUENCE: 27
ggattcacct tccgtgacta ctcc                                       24

SEQ ID NO: 28           moltype = AA   length = 8
FEATURE                 Location/Qualifiers
REGION                  1..8
                        note = synthetic
source                  1..8
                        mol_type = protein
                        organism = synthetic construct
SEQUENCE: 28
GFTFRDYS                                                         8

SEQ ID NO: 29           moltype = DNA   length = 24
FEATURE                 Location/Qualifiers
misc_feature            1..24
                        note = synthetic
```

-continued

```
source                  1..24
                        mol_type = other DNA
                        organism = synthetic construct
SEQUENCE: 29
gttacttttt ttaatagtgc cata                                         24

SEQ ID NO: 30           moltype = AA   length = 8
FEATURE                 Location/Qualifiers
REGION                  1..8
                        note = synthetic
source                  1..8
                        mol_type = protein
                        organism = synthetic construct
SEQUENCE: 30
VTFFNSAI                                                             8

SEQ ID NO: 31           moltype = DNA   length = 39
FEATURE                 Location/Qualifiers
misc_feature            1..39
                        note = synthetic
source                  1..39
                        mol_type = other DNA
                        organism = synthetic construct
SEQUENCE: 31
gcgagagaaa gagagcctat tgtgggggc tttgactac                          39

SEQ ID NO: 32           moltype = AA   length = 13
FEATURE                 Location/Qualifiers
REGION                  1..13
                        note = synthetic
source                  1..13
                        mol_type = protein
                        organism = synthetic construct
SEQUENCE: 32
AREREPIVGG FDY                                                      13

SEQ ID NO: 33           moltype = DNA   length = 324
FEATURE                 Location/Qualifiers
misc_feature            1..324
                        note = synthetic
source                  1..324
                        mol_type = other DNA
                        organism = synthetic construct
SEQUENCE: 33
gacatccaga tgacccagtc tccatcctcc ctgtctgcat ctgtaggaga cagagtcacc   60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                         324

SEQ ID NO: 34           moltype = AA   length = 108
FEATURE                 Location/Qualifiers
REGION                  1..108
                        note = synthetic
source                  1..108
                        mol_type = protein
                        organism = synthetic construct
SEQUENCE: 34
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPPITFG QGTRLEIK              108

SEQ ID NO: 35           moltype = DNA   length = 18
FEATURE                 Location/Qualifiers
misc_feature            1..18
                        note = synthetic
source                  1..18
                        mol_type = other DNA
                        organism = synthetic construct
SEQUENCE: 35
cagagcatta gcagctat                                                18

SEQ ID NO: 36           moltype = AA   length = 6
FEATURE                 Location/Qualifiers
REGION                  1..6
                        note = synthetic
source                  1..6
                        mol_type = protein
                        organism = synthetic construct
```

```
SEQUENCE: 36
QSISSY                                                                                   6

SEQ ID NO: 37              moltype =    length =
SEQUENCE: 37
000

SEQ ID NO: 38              moltype =    length =
SEQUENCE: 38
000

SEQ ID NO: 39              moltype = DNA   length = 30
FEATURE                    Location/Qualifiers
misc_feature               1..30
                           note = synthetic
source                     1..30
                           mol_type = other DNA
                           organism = synthetic construct
SEQUENCE: 39
caacagagtt acagtaccccc tccgatcacc                                                         30

SEQ ID NO: 40              moltype = AA   length = 10
FEATURE                    Location/Qualifiers
REGION                     1..10
                           note = synthetic
source                     1..10
                           mol_type = protein
                           organism = synthetic construct
SEQUENCE: 40
QQSYSTPPIT                                                                                10

SEQ ID NO: 41              moltype = DNA   length = 354
FEATURE                    Location/Qualifiers
misc_feature               1..354
                           note = synthetic
source                     1..354
                           mol_type = other DNA
                           organism = synthetic construct
SEQUENCE: 41
gaggtgcagc tggtggagtc tggggggaggc ttggtccagc ctggggggtc cctgagactc        60
tcctgtgcag cctccggatt caccttcagt aggaataata tgcactgggt ccgccaggct        120
ccagggaagg gactggaata tgtttcaggt attagtagta atggggggtcg cacatattat        180
gcagactctg tgaagggcag attcaccatc tccagagaca attccaagaa cacgctgtat        240
cttcaaatgg gcggcctgag agctgcggac atggctgtgt atttctgtac gagagatgac        300
gagctgcttt cctttgacta ctggggccag ggaaccctgg tcactgtctc ctca             354

SEQ ID NO: 42              moltype = AA   length = 118
FEATURE                    Location/Qualifiers
REGION                     1..118
                           note = synthetic
source                     1..118
                           mol_type = protein
                           organism = synthetic construct
SEQUENCE: 42
EVQLVESGGG LVQPGGSLRL SCAASGFTFS RNNMHWVRQA PGKGLEYVSG ISSNGGRTYY        60
ADSVKGRFTI SRDNSKNTLY LQMGGLRAAD MAVYFCTRDD ELLSFDYWGQ GTLVTVSS          118

SEQ ID NO: 43              moltype = DNA   length = 24
FEATURE                    Location/Qualifiers
misc_feature               1..24
                           note = synthetic
source                     1..24
                           mol_type = other DNA
                           organism = synthetic construct
SEQUENCE: 43
ggattcacct tcagtaggaa taat                                                                24

SEQ ID NO: 44              moltype = AA   length = 8
FEATURE                    Location/Qualifiers
REGION                     1..8
                           note = synthetic
source                     1..8
                           mol_type = protein
                           organism = synthetic construct
SEQUENCE: 44
GFTFSRNN                                                                                  8

SEQ ID NO: 45              moltype = DNA   length = 24
FEATURE                    Location/Qualifiers
```

-continued

```
misc_feature          1..24
                      note = synthetic
source                1..24
                      mol_type = other DNA
                      organism = synthetic construct
SEQUENCE: 45
attagtagta atgggggtcg caca                                        24

SEQ ID NO: 46         moltype = AA  length = 8
FEATURE               Location/Qualifiers
REGION                1..8
                      note = synthetic
source                1..8
                      mol_type = protein
                      organism = synthetic construct
SEQUENCE: 46
ISSNGGRT                                                          8

SEQ ID NO: 47         moltype = DNA  length = 33
FEATURE               Location/Qualifiers
misc_feature          1..33
                      note = synthetic
source                1..33
                      mol_type = other DNA
                      organism = synthetic construct
SEQUENCE: 47
acgagagatg acgagctgct ttcctttgac tac                             33

SEQ ID NO: 48         moltype = AA  length = 11
FEATURE               Location/Qualifiers
REGION                1..11
                      note = synthetic
source                1..11
                      mol_type = protein
                      organism = synthetic construct
SEQUENCE: 48
TRDDELLSFD Y                                                      11

SEQ ID NO: 49         moltype = AA  length = 875
FEATURE               Location/Qualifiers
REGION                1..875
                      note = hMUC16 membrane-proximal domain(P13810-P14451).mFc ;
                       Accession# NP_078966
source                1..875
                      mol_type = protein
                      organism = synthetic construct
SEQUENCE: 49
PGSRKFNTTE RVLQGLLRPL FKNTSVGPLY SGCRLTLLRP EKDGEATGVD AICTHRPDPT  60
GPGLDREQLY LELSQLTHSI TELGPYTLDR DSLYVNGFTH RSSVPTTSTG VVSEEPFTLN  120
FTINNLRYMA DMGQPGSLKF NITDNVMQHL LSPLFQRSSL GARYTGCRVI ALRSVKNGAE  180
TRVDLLCTYL QPLSGPGLPI KQVFHELSQQ THGITRLGPY SLDKDSLYLN GYNEPGPDEP  240
PTTPKPATTF LPPLSEATTA MGYHLKTLTL NFTISNLQYS PDMGKGSATF NSTEGVLQHL  300
LRPLFQKSSM GPFYLGCQLI SLRPEKDGAA TGVDTTCTYH PDPVGPGLDI QQLYWELSQL  360
THGVTQLGFY VLDRDSLFIN GYAPQNLSIR GEYQINFHIV NWNLSNPDPT SSEYITLLRD  420
IQDKVTTLYK GSQLHDTFRF CLVTNLTMDS VLVTVKALFS SNLDPSLVEQ VFLDKTLNAS  480
FHWLGSTYQL VDIHVTEMES SVYQPTSSSS TQHFYLNFTI TNLPYSQDKA QPGTTNYQRN  540
KRNIEDALNQ LFRNSSIKSY FSDCQVSTFR SVPNRHHTGV DSLCNFSPLA RRVDRVAIYE  600
EFLRMTRNGT QLQNFTLDRS SVLVDGYSPN RNEPLTGNSD LPEPRGPTIK PCPPCKCPAP  660
NLLGGPSVFI FPPKIKDVLM ISLSPIVTCV VVDVSEDDPD VQISWFVNNV EVHTAQTQTH  720
REDYNSTLRV VSALPIQHQD WMSGKEFKCK VNNKDLPAPI ERTISKPKGS VRAPQVYVLP  780
PPEEEMTKKQ VTLTCMVTDF MPEDIYVEWT NNGKTELNYK NTEPVLDSDG SYFMYSKLRV  840
EKKNWVERNS YSCSVVHEGL HNHHTTKSFS RTPGK                             875

SEQ ID NO: 50         moltype = AA  length = 367
FEATURE               Location/Qualifiers
REGION                1..367
                      note = hCD28 ecto (N19-P152).mFc ; Accession# NP_006130
source                1..367
                      mol_type = protein
                      organism = synthetic construct
SEQUENCE: 50
NKILVKQSPM LVAYDNAVNL SCKYSYNLFS REFRASLHKG LDSAVEVCVV YGNYSQQLQV  60
YSKTGFNCDG KLGNESVTFY LQNLYVNQTD IYFCKIEVMY PPPYLDNEKS NGTIIHVKGK  120
HLCPSPLFPG PSKPEPRGPT IKPCPPCKCP APNLLGGPSV FIFPPKIKDV LMISLSPIVT  180
CVVVDVSEDD PDVQISWFVN NVEVHTAQTQ THREDYNSTL RVVSALPIQH QDWMSGKEFK  240
CKVNNKDLPA PIERTISKPK GSVRAPQVYV LPPPEEEMTK KQVTLTCMVT DPMPEDIYVE  300
WTNNGKTELN YKNTEPVLDS DGSYFMYSKL RVEKKNWVER NSYSCSVVHE GLHNHHTTKS  360
FSRTPGK                                                           367
```

-continued

```
SEQ ID NO: 51              moltype = AA  length = 669
FEATURE                    Location/Qualifiers
REGION                     1..669
                           note = hMUC16 membrane-proximal domain(P13810-P14451).mmH
source                     1..669
                           mol_type = protein
                           organism = synthetic construct
SEQUENCE: 51
GSRKFNTTER VLQGLLRPLF KNTSVGPLYS GCRLTLLRPE KDGEATGVDA ICTHRPDPTG  60
PGLDREQLYL ELSQLTHSIT ELGPYTLDRD SLYVNGFTHR SSVPTTSTGV VSEEPFTLNF  120
TINNLRYMAD MGQPGSLKFN ITDNVMQHLL SPLFQRSSLG ARYTGCRVIA LRSVKNGAET  180
RVDLLCTYLQ PLSGPGLPIK QVFHELSQQT HGITRLGPYS LDKDSLYLNG YNEPGPDEPP  240
TTPKPATTFL PPLSEATTAM GYHLKTLTLN FTISNLQYSP DMGKGSATFN STEGVLQHLL  300
RPLFQKSSMG PFYLGCQLIS LRPEKDGAAT GVDTTCTYHP DPVGPGLDIQ QLYWELSQLT  360
HGVTQLGFYV LDRDSLFING YAPQNLSIRG EYQINFHIVN WNLSNPDPTS SEYITLLRDI  420
QDKVTTLYKG SQLHDTFRFC LVTNLTMDSV LVTVKALFSS NLDPSLVEQV FLDKTLNASF  480
HWLGSTYQLV DIHVTEMESS VYQPTSSSST QHFYLNFTIT NLPYSQDKAQ PGTTNYQRNK  540
RNIEDALNQL FRNSSIKSYF SDCQVSTFRS VPNRHHTGVD SLCNFSPLAR RVDRVAIYEE  600
FLRMTRNGTQ LQNFTLDRSS VLVDGYSPNR NEPLTGNSDL PEQKLISEED LGGEQKLISE  660
EDLHHHHHH                                                         669

SEQ ID NO: 52              moltype = AA  length = 367
FEATURE                    Location/Qualifiers
REGION                     1..367
                           note = hCD28 ecto (N19-P152).mFc
source                     1..367
                           mol_type = protein
                           organism = synthetic construct
SEQUENCE: 52
NKILVKQSPM LVAYDNAVNL SCKYSYNLFS REFRASLHKG LDSAVEVCVV YGNYSQQLQV  60
YSKTGFNCDG KLGNESVTFY LQNLYVNQTD IYFCKIEVMY PPPYLDNEKS NGTIIHVKGK  120
HLCPSPLFPG PSKPEPRGPT IKPCPPCKCP APNLLGGPSV FIFPPPKIKDV LMISLSPIVT  180
CVVVDVSEDD PDVQISWFVN NVEVHTAQTQ THREDYNSTL RVVSALPIQH QDWMSGKEFK  240
CKVNNKDLPA PIERTISKPK GSVRAPQVYV LPPPEEEMTK KQVTLTCMVT DFMPEDIYVE  300
WTNNGKTELN YKNTEPVLDS DGSYFMYSKL RVEKKNWVER NSYSCSVVHE GLHNHHTTKS  360
FSRTPGK                                                           367

SEQ ID NO: 53              moltype = AA  length = 162
FEATURE                    Location/Qualifiers
REGION                     1..162
                           note = hCD28 ecto (N19-P152).mmH
source                     1..162
                           mol_type = protein
                           organism = synthetic construct
SEQUENCE: 53
NKILVKQSPM LVAYDNAVNL SCKYSYNLFS REFRASLHKG LDSAVEVCVV YGNYSQQLQV  60
YSKTGFNCDG KLGNESVTFY LQNLYVNQTD IYFCKIEVMY PPPYLDNEKS NGTIIHVKGK  120
HLCPSPLFPG PSKPEQKLIS EEDLGGEQKL ISEEDLHHHH HH                    162

SEQ ID NO: 54              moltype = AA  length = 159
FEATURE                    Location/Qualifiers
REGION                     1..159
                           note = Mouse CD28 (Accession# NP_031668.3)mCD28
                           ecto(N20-L150).mmH
source                     1..159
                           mol_type = protein
                           organism = synthetic construct
SEQUENCE: 54
NKILVKQSPL LVVDSNEVSL SCRYSYNLLA KEFRASLYKG VNSDVEVCVG NGNFTYQPQF  60
RSNAEFNCDG DFDNETVTFR LWNLHVNHTD IYFCKIEFMY PPPYLDNERS NGTIIHIKEK  120
HLCHTQSSPK LEQKLISEED LGGEQKLISE EDLHHHHHH                        159
```

BISPECIFIC ANTI-MUC16 X ANTI-CD28 ANTIBODIES AND USES THEREOF

CROSS-REFERENCE TO RELATED APPLICATIONS

This application is a continuation of U.S. application Ser. No. 16/719,273, filed Dec. 18, 2019, which claims the benefit under 35 USC § 119(e) of U.S. Provisional Application No. 62/782,142, filed on Dec. 19, 2018, and 62/815, 861, filed on Mar. 8, 2019, each of which is incorporated herein by reference in its entirety for all purposes.

SEQUENCE LISTING

This application incorporates by reference a computer readable Sequence Listing in ST.26 XML format, titled 10493US02-Sequence, created on Aug. 17, 2022, and containing 69,624 bytes.

FIELD OF THE INVENTION

The present invention relates to bispecific antigen-binding molecules that bind CD28 and a target molecule such as MUC16, and methods of use thereof.

BACKGROUND

CD28 is a type I transmembrane protein, which has a single extracellular Ig-V-like domain assembled as a homodimer and which is expressed on the surface of T cells. CD28 is the receptor for the CD80 (B7.1) and CD86 (B7.2) proteins and is activated by CD80 or CD86 expressed on antigen-presenting cells (APCs). The binding of CD28 to CD80 or CD86 provides co-stimulatory signals important for T cell activation and survival. T cell stimulation through CD28, in addition to the T-cell receptor (TCR), provides a potent signal for the production of various interleukins. CD28 also potentiates cellular signals such as pathways controlled by the NFκB transcription factor after TCR activation. The CD28 co-signal is important for effective T-cell activation such as T cell differentiation, proliferation, cytokine release and cell-death.

Anti-CD28 antibodies have been proposed for therapeutic purposes involving the activation of T cells. One particular anti-CD28 antibody, TGN1412 (anti-CD28 superagonist), was used in a clinical trial in 2006. Six healthy volunteers were dosed intravenously with TGN1412 (anti-CD28 super-agonist) at a dose of 0.1 mg/kg. Within two hours, all six patients had significant inflammatory responses (cytokine storm), and all patients were in multi-organ failure within sixteen hours. Subjects were treated with corticosteroids, and cytokine levels returned to normal within 2-3 days. The starting dose of 0.1 mg/kg in a Phase 1 study was based on a 500-fold multiple of the no-observed-adverse-effect-level ("NOAEL") of 50 mg/kg in cynomolgus monkeys (Sunth-aralingam, et al., Cytokine Storm in a Phase 1 Trial of the Anti-CD28 Monoclonal Antibody TGN1412, NEJM 355: 1018-1028 (2006)). Unfortunately, the cytokine storm induced by TGN1412 was not predicted by toxicology studies in cynomolgus macaques or in ex vivo human PBMC studies.

Mucin 16 (MUC16), also known as cancer antigen 125, carcinoma antigen 125, carbohydrate antigen 125, or CA-125, is a highly glycosylated integral membrane glyco-protein. MUC16 comprises three major domains: an extra-cellular N-terminal domain, a large tandem repeat domain interspersed with sea urchin sperm, enterokinase, agrin (SEA) domains and a carboxyl terminal domain that com-prises a segment of the transmembrane region and a short cytoplasmic tail. Proteolytic cleavage results in shedding of the extracellular portion of MUC16 into the bloodstream. MUC16 is overexpressed in cancers including ovarian can-cer, breast cancer, pancreatic cancer, non-small-cell lung cancer, intrahepatic cholangiocarcinoma-mass forming type, adenocarcinoma of the uterine cervix, and adenocarcinoma of the gastric tract, and in diseases and conditions including inflammatory bowel disease, liver cirrhosis, cardiac failure, peritoneal infection, and abdominal surgery. (Haridas, D. et al., 2014, FASEB J., 28:4183-4199). Expression of MUC16 on cancer cells has been shown to protect the cancer cells from the immune system. (Felder, M. et al., 2014, Molecular Cancer, 13:129).

Methods for treating ovarian cancer using antibodies to MUC16 have been investigated. However, the monoclonal antibodies, oregovomab and abgovomab, have had limited success. (Felder, supra, Das, S. and Batra, S. K. 2015, Cancer Res. 75:4660-4674.) Accordingly, there is a need in the art for improved MUC16 antibodies for treating cancer.

Furthermore, bispecific antigen-binding molecules that bind both CD28 and a target antigen, such as MUC16, would be useful in therapeutic settings in which specific targeting to tumor cells and T cell mediated killing of cells that express the target antigen is desired.

BRIEF SUMMARY OF THE INVENTION

In a first aspect, the present invention provides bispecific antigen-binding molecules that bind CD28 and MUC16, also referred to herein as "anti-CD28/anti-MUC16 bispecific molecules." The anti-MUC16 portion of the anti-CD28/anti-MUC16 bispecific molecule is useful for targeting tumor cells that express MUC16 (e.g., ovarian tumor cells), and the anti-CD28 portion of the bispecific molecule is useful for activating T-cells. The simultaneous binding of MUC16 on a tumor cell and CD28 on a T-cell facilitates directed killing (cell lysis) of the targeted tumor cell by the activated T-cell. The anti-CD28/anti-MUC16 bispecific molecules of the invention are therefore useful, inter alia, for treating diseases and disorders related to or caused by MUC16-expressing tumors (e.g., ovarian cancer).

The bispecific antigen-binding molecules according to this aspect of the present invention comprise a first antigen-binding domain that specifically binds human CD28, and a second antigen-binding domain that specifically binds MUC16. The present invention includes anti-CD28/anti-MUC16 bispecific molecules (e.g., bispecific antibodies) wherein each antigen-binding domain comprises a heavy chain variable region (HCVR) paired with a light chain variable region (LCVR). In certain exemplary embodiments of the invention, the anti-CD28 antigen-binding domain and the anti-MUC16 antigen binding domain each comprise different, distinct HCVRs paired with a common LCVR.

The present invention provides anti-CD28/anti-MUC16 bispecific molecules, wherein the first antigen-binding domain that specifically binds CD28 comprises any of the HCVR amino acid sequences as set forth in Table 3. The first antigen-binding domain that specifically binds CD28 may also comprise any of the LCVR amino acid sequences as set forth in Table 3. According to certain embodiments, the first antigen-binding domain that specifically binds CD28 com-prises any of the HCVR/LCVR amino acid sequence pairs as set forth in Table 3. The present invention also provides anti-CD28/anti-MUC16 bispecific molecules, wherein the first antigen-binding domain that specifically binds CD28 comprises any of the heavy chain CDR1-CDR2-CDR3 amino acid sequences as set forth in Table 3, and/or any of the light chain CDR1-CDR2-CDR3 amino acid sequences as set forth in Table 3.

According to certain embodiments, the present invention provides anti-CD28/anti-MUC16 bispecific molecules, wherein the first antigen-binding domain that specifically binds CD28 comprises a heavy chain variable region (HCVR) having an amino acid sequence selected from the group consisting of SEQ ID NOs: 18 and 42 or a substantially similar sequence thereof having at least 90%, at least 95%, at least 98% or at least 99% sequence identity.

The present invention also provides anti-CD28/anti-MUC16 bispecific molecules, wherein the first antigen-binding domain that specifically binds CD28 comprises a light chain variable region (LCVR) having an amino acid sequence selected from the group consisting of SEQ ID NOs: 10 and 34, or a substantially similar sequence thereof having at least 90%, at least 95%, at least 98% or at least 99% sequence identity.

The present invention also provides anti-CD28/anti-MUC16 bispecific molecules, wherein the first antigen-binding domain that specifically binds CD28 comprises a HCVR and LCVR (HCVR/LCVR) amino acid sequence pair selected from the group consisting of SEQ ID NOs: 18/10 and 42/34.

The present invention also provides anti-CD28/anti-MUC16 bispecific molecules, wherein the first antigen-binding domain that specifically binds CD28 comprises a heavy chain CDR3 (HCDR3) domain having an amino acid sequence selected from the group consisting of SEQ ID NOs: 24 and 48, or a substantially similar sequence thereto having at least 90%, at least 95%, at least 98% or at least 99% sequence identity; and a light chain CDR3 (LCDR3) domain having an amino acid sequence selected from the group consisting of SEQ ID NOs: 16 and 40, or a substantially similar sequence thereof having at least 90%, at least 95%, at least 98% or at least 99% sequence identity.

In certain embodiments, the first antigen-binding domain that specifically binds CD28 comprises a HCDR3/LCDR3 amino acid sequence pair selected from the group consisting of SEQ ID NOs: 24/16 and 48/40.

The present invention also provides anti-CD28/anti-MUC16 bispecific antigen-binding molecules, wherein the first antigen-binding domain that specifically binds CD28 comprises a heavy chain CDR1 (HCDR1) domain having an amino acid sequence selected from the group consisting of SEQ ID NOs: 20 and 44, or a substantially similar sequence thereof having at least 90%, at least 95%, at least 98% or at least 99% sequence identity; a heavy chain CDR2 (HCDR2) domain having an amino acid sequence selected from the group consisting of SEQ ID NOs: 22 and 46, or a substantially similar sequence thereof having at least 90%, at least 95%, at least 98% or at least 99% sequence identity; a light chain CDR1 (LCDR1) domain having an amino acid sequence selected from the group consisting of SEQ ID NOs: 12 and 36, or a substantially similar sequence thereof having at least 90%, at least 95%, at least 98% or at least 99% sequence identity; and a light chain CDR2 (LCDR2) domain having an amino acid sequence selected from the group consisting of SEQ ID NOs: 14 and 38, or a substantially similar sequence thereof having at least 90%, at least 95%, at least 98% or at least 99% sequence identity.

Certain non-limiting, exemplary anti-CD28/anti-MUC16 bispecific antigen-binding molecules of the invention include a first antigen-binding domain that specifically binds CD28 comprising HCDR1-HCDR2-HCDR3-LCDR1-LCDR2-LCDR3 domains, respectively, having the amino acid sequence selected from the group consisting of: SEQ ID NOs: 20-22-24-12-14-16 and 44-46-48-36-38-40.

The present invention also provides anti-CD28/anti-MUC16 bispecific molecules, wherein the second antigen-binding domain that specifically binds MUC16 comprises a heavy chain variable region (HCVR) having the amino acid sequence selected from the group consisting SEQ ID NOs: 2 and 26, or a substantially similar sequence thereof having at least 90%, at least 95%, at least 98% or at least 99% sequence identity.

The present invention also provides anti-CD28/anti-MUC16 bispecific molecules, wherein the second antigen-binding domain that specifically binds MUC16 comprises a light chain variable region (LCVR) having the amino acid sequence selected from the group consisting of SEQ ID NOs: 10 and 34, or a substantially similar sequence thereof having at least 90%, at least 95%, at least 98% or at least 99% sequence identity.

The present invention also provides anti-CD28/anti-MUC16 bispecific molecules, wherein the second antigen-binding domain that specifically binds MUC16 comprises a HCVR and LCVR (HCVR/LCVR) amino acid sequence pair selected from the group consisting of SEQ ID NOs: 2/10 and 26/34.

The present invention also provides anti-CD28/anti-MUC16 bispecific molecules, wherein the second antigen-binding domain that specifically binds MUC16 comprises a heavy chain CDR3 (HCDR3) domain having the amino acid sequence selected from the group consisting of SEQ ID NOs: 8 and 32, or a substantially similar sequence thereto having at least 90%, at least 95%, at least 98% or at least 99% sequence identity; and a light chain CDR3 (LCDR3) domain having an amino acid sequence selected from the group consisting of SEQ ID NOs: 16 and 40, or a substantially similar sequence thereof having at least 90%, at least 95%, at least 98% or at least 99% sequence identity.

In certain embodiments, the second antigen-binding domain that specifically binds MUC16 comprises a HCDR3/LCDR3 amino acid sequence pair selected from the group consisting of SEQ ID NOs: 8/16 and 32/40.

The present invention also provides anti-CD28/anti-MUC16 bispecific antigen-binding molecules, wherein the second antigen-binding domain that specifically binds MUC16 comprises a heavy chain CDR1 (HCDR1) domain having the amino acid sequence selected from the group consisting of SEQ ID NOs: 4 and 28, or a substantially similar sequence thereof having at least 90%, at least 95%, at least 98% or at least 99% sequence identity; a heavy chain CDR2 (HCDR2) domain having the amino acid sequence selected from the group consisting of SEQ ID NOs: 6 and 30, or a substantially similar sequence thereof having at least 90%, at least 95%, at least 98% or at least 99% sequence identity; a light chain CDR1 (LCDR1) domain having an amino acid sequence selected from the group consisting of SEQ ID NOs: 12 and 36, or a substantially similar sequence thereof having at least 90%, at least 95%, at least 98% or at least 99% sequence identity; and a light chain CDR2 (LCDR2) domain having an amino acid sequence selected from the group consisting of SEQ ID NOs: 14 and 38, or a substantially similar sequence thereof having at least 90%, at least 95%, at least 98% or at least 99% sequence identity.

Certain non-limiting, exemplary anti-CD28/anti-MUC16 bispecific antigen-binding molecules of the invention include a second antigen-binding domain that specifically binds MUC16 comprising HCDR1-HCDR2-HCDR3-

LCDR1-LCDR2-LCDR3 domains, respectively, having the amino acid sequences selected from the group consisting of: SEQ ID NOs: 4-6-8-12-14-16 and 28-30-32-36-38-40.

In a related embodiment, the invention includes anti-CD28/anti-MUC16 bispecific antigen binding molecules wherein the second antigen-binding domain that specifically binds MUC16 comprises the heavy and light chain CDR domains contained within heavy and light chain variable region (HCVR/LCVR) sequences selected from the group consisting of SEQ ID NOs: 2/10 and 26/34.

In another aspect, the present invention provides nucleic acid molecules encoding any of the HCVR, LCVR or CDR sequences of the anti-CD28/anti-MUC16 bispecific antigen-binding molecules disclosed herein, including nucleic acid molecules comprising the polynucleotide sequences as set forth in Table 2 and/or Table 4 herein, as well as nucleic acid molecules comprising two or more of the polynucleotide sequences as set forth in Table 2 and/or Table 4 in any functional combination or arrangement thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

The present invention includes anti-CD28/anti-MUC16 bispecific antigen-binding molecules wherein any of the aforementioned antigen-binding domains that specifically bind CD28 is combined, connected or otherwise associated with any of the aforementioned antigen binding domains that specifically bind MUC16 to form a bispecific antigen-binding molecule that binds CD28 and MUC16.

The present invention includes anti-CD28/anti-MUC16 bispecific antigen-binding molecules having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising an anti-CD28/anti-MUC16 bispecific antigen-binding molecule as disclosed herein and a pharmaceutically acceptable carrier. In a related aspect, the invention features a composition which is a combination of an anti-CD28/anti-MUC16 bispecific antigen-binding molecule and a second therapeutic agent. In one embodiment, the second therapeutic agent is any agent that is advantageously combined with an anti-CD28/anti-MUC16 bispecific antigen-binding molecule. Exemplary agents that may be advantageously combined with an anti-CD28/anti-MUC16 bispecific antigen-binding molecule are discussed in detail elsewhere herein.

In yet another aspect, the invention provides therapeutic methods for targeting/killing tumor cells expressing MUC16 using an anti-CD28/anti-MUC16 bispecific antigen-binding molecule of the invention, wherein the therapeutic methods comprise administering a therapeutically effective amount of a pharmaceutical composition comprising an anti-CD28/anti-MUC16 bispecific antigen-binding molecule of the invention to a subject in need thereof.

The present invention also includes the use of an anti-CD28/anti-MUC16 bispecific antigen-binding molecule of the invention in the manufacture of a medicament for the treatment of a disease or disorder related to or caused by MUC16 expression.

In yet another aspect, the invention provides therapeutic methods for targeting/killing tumor cells expressing MUC16 using an anti-CD28/anti-MUC16 bispecific antigen-binding molecule of the invention, wherein the anti-CD28/anti-MUC16 bispecific antigen-binding molecule is combined with other anti-tumor bispecific antigen-binding molecules that bind to CD3 (e.g., anti-CD28/anti-MUC16 combined with anti-CD3/anti-MUC16 antibodies).

In still another aspect, the invention provides therapeutic methods for targeting/killing tumor cells expressing MUC16 using an anti-CD28/anti-MUC16 bispecific antigen-binding molecule of the invention, wherein the anti-CD28/anti-MUC16 bispecific antigen-binding molecule is combined with a checkpoint inhibitor targeting, for example, PD-1, PD-L1 or CTLA-4 (e.g., anti-CD28/anti-MUC16 combined with anti-PD-1 antibodies). In certain embodiments, it is envisioned that the anti-CD28/anti-MUC16 antibodies of the invention may be combined with agents that target PD-1, such as Pembrolizumab (Keytruda®), Nivolumab (Opdivo®), or Cemiplimab (Libtayo®). In certain embodiments, it is envisioned that the anti-CD28/anti-MUC16 antibodies of the invention may be combined with agents that target PD-L1, such as Atezolizumab (Tecentriq®), Avelumab (Bavencio®), or Durvalumab (Imfinzi®). In certain embodiments, it is envisioned that the anti-CD28/anti-MUC16 antibodies of the invention may be combined with agents that target CTLA-4, such as Ipilimumab (Yervoy®).

In still another aspect, the invention provides therapeutic methods for targeting/killing tumor cells expressing MUC16 using an anti-CD28/anti-MUC16 bispecific antigen-binding molecule of the invention, wherein the anti-CD28/anti-MUC16 bispecific antigen-binding molecule is combined with other anti-tumor bispecific antigen-binding molecules that binds to CD3 (e.g., anti-CD28/anti-MUC16 combined with anti-CD3/anti-MUC16 bispecific antibodies) and a checkpoint inhibitor targeting PD-1, PDL-1 or CTLA-4 (e.g., anti-CD28/anti-MUC16 combined with anti-PD-1 antibodies).

Other embodiments will become apparent from a review of the ensuing detailed description.

The graph shows tumor growth as the percentage of control calculated as $$\frac{\text{Tumor Volume}}{\text{Tumor Volume of Control}} \times 100$$

Figure 2A:
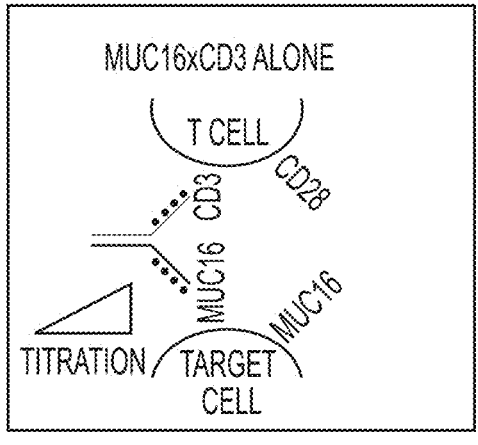
Figure 2A:
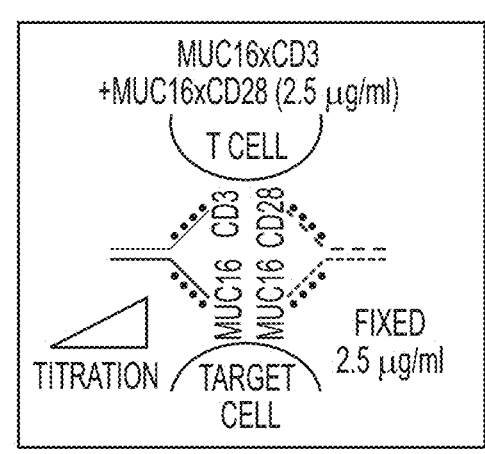
Figure 2B:
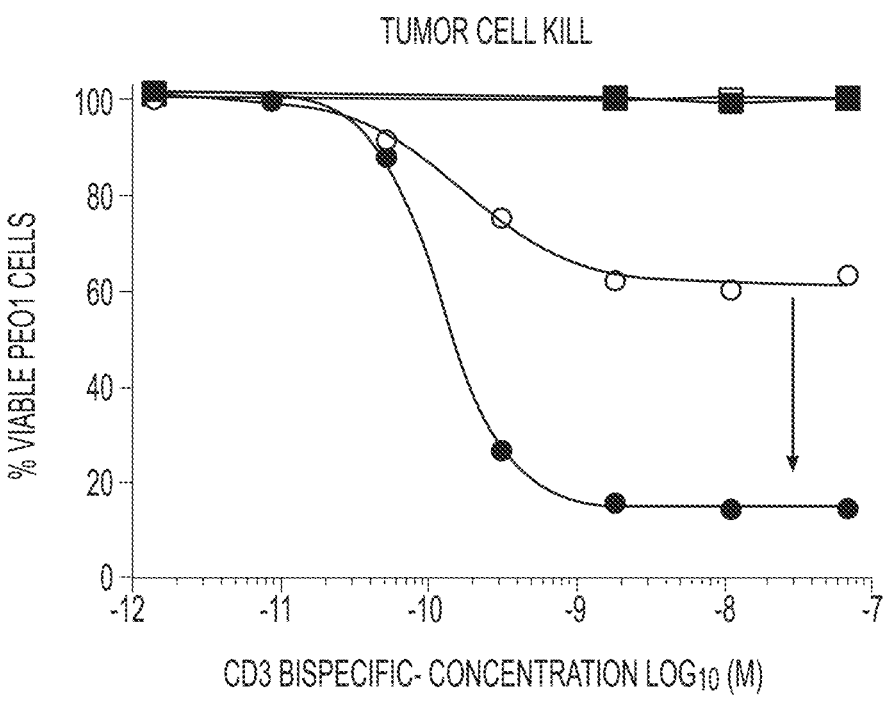
Figure 2C:
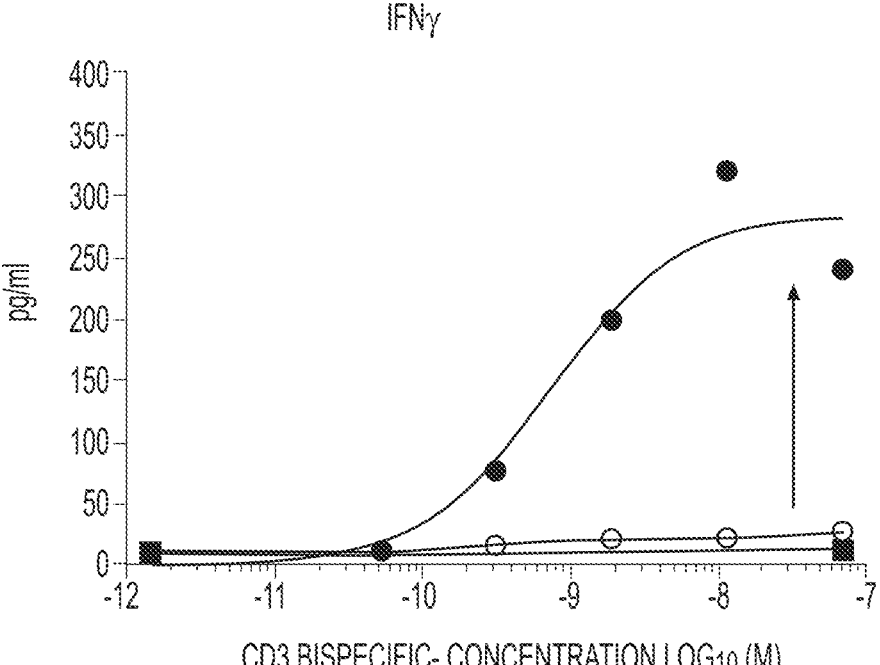
Figure 2D:
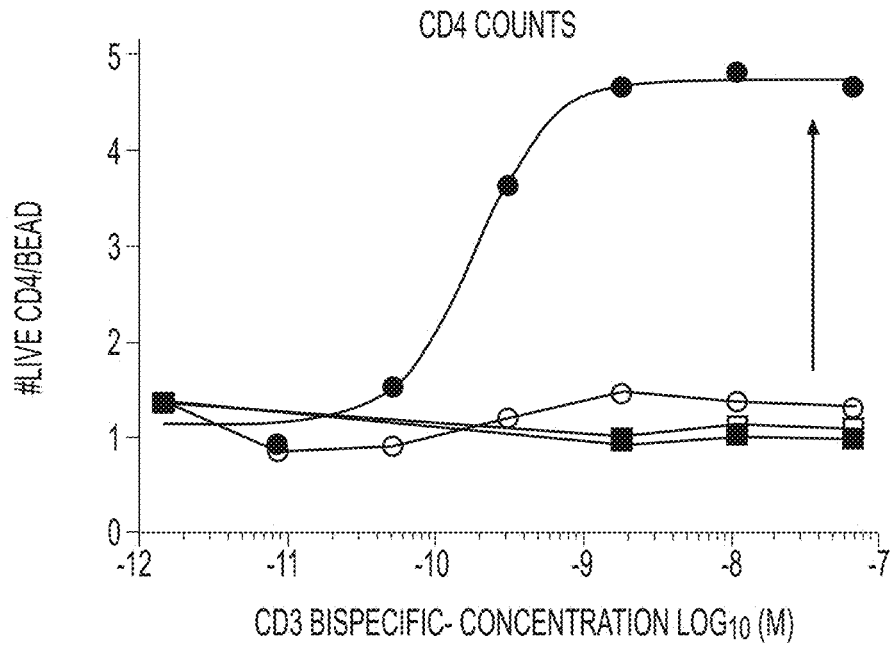
Figure 2D:
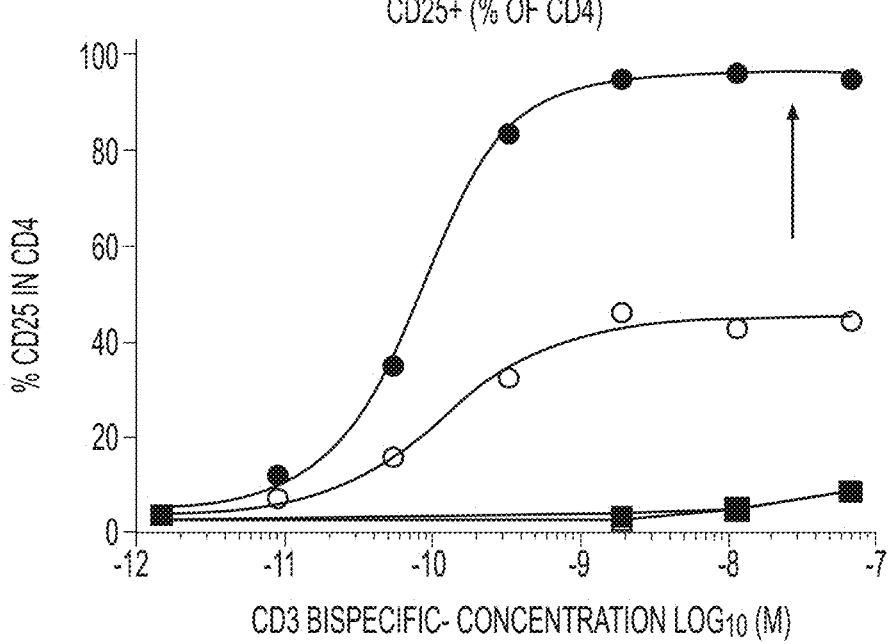
Figure 2E:
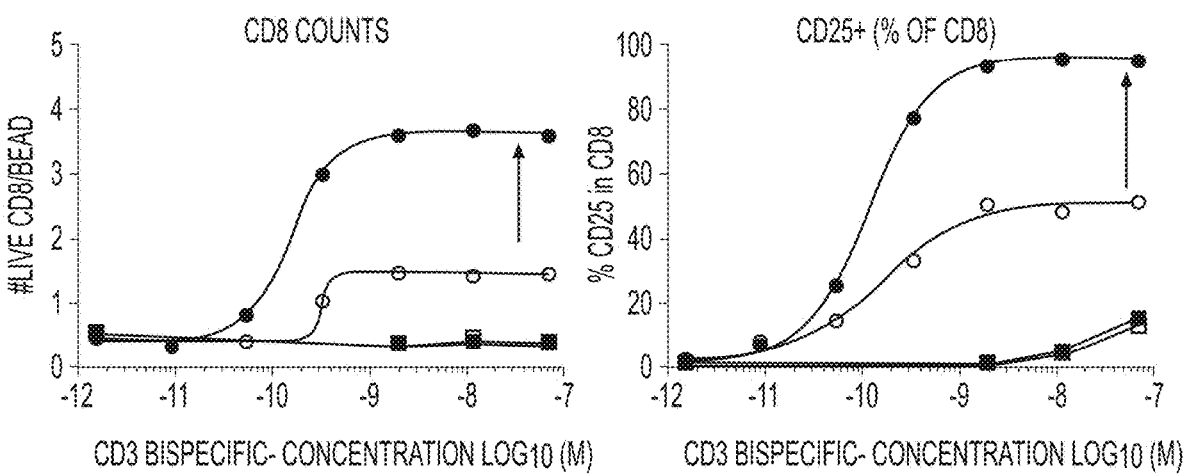
Figure 2F:
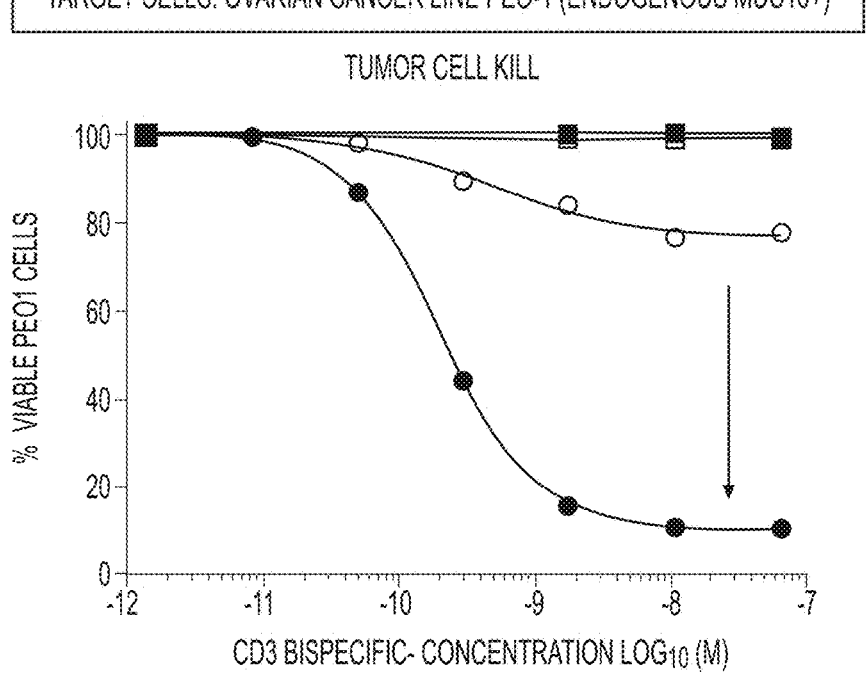
Figure 2G:
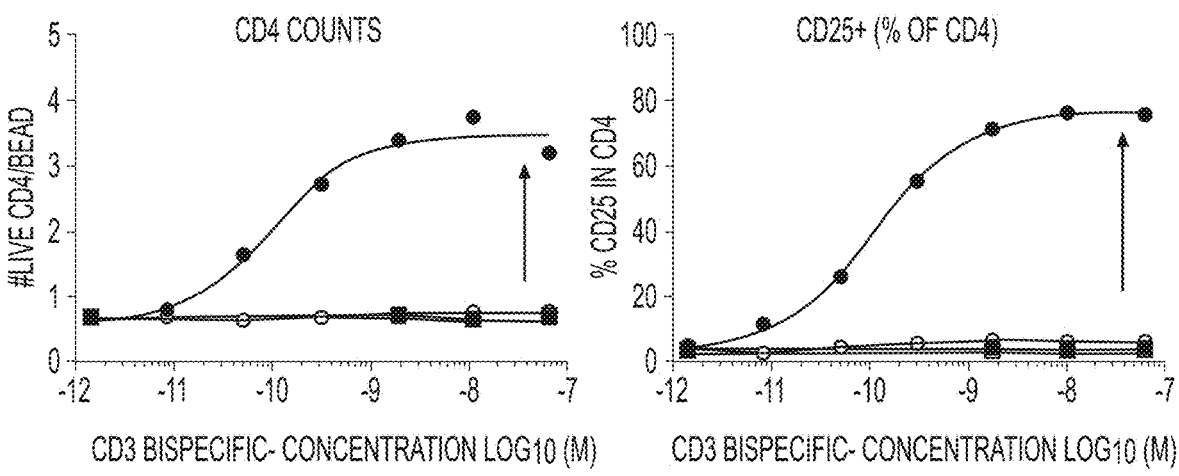
Figure 2H:
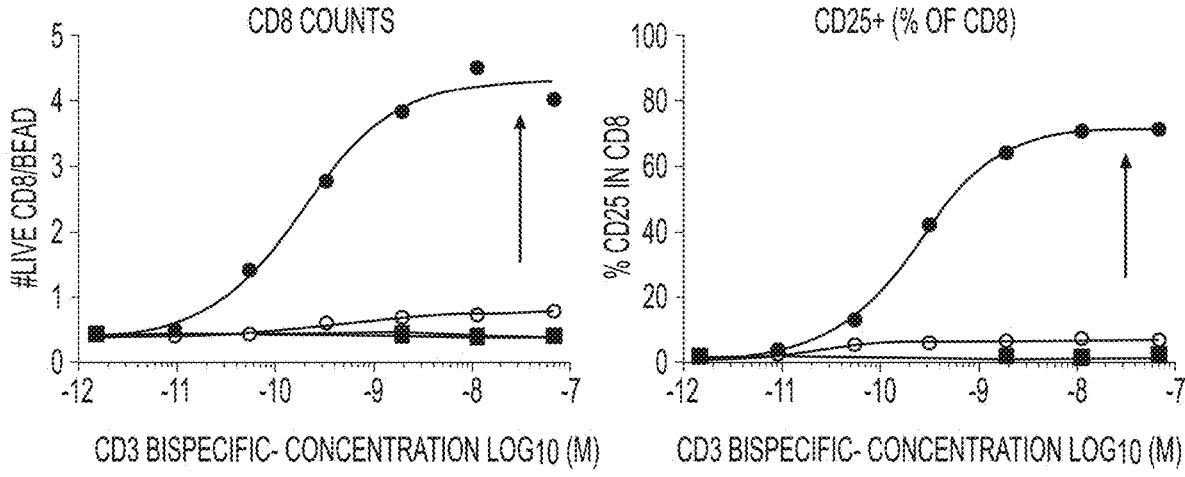

FIGS. 2A to 2I are schematic and graphs showing that the exemplary anti-MUC16×CD28 of the invention potentiate T cell action in the presence of TCR stimulation by anti-MUC16×CD3 and cancer cell lines with endogenous MUC16 (PEO1). FIGS. 2B to 2E are graphs showing the data for human PBMC. FIGS. 2F to 2H are graphs showing the data for cynomolgus monkey PBMC. Human T cells (for FIGS. 2B to 2E) or cynomolgus T cells (for FIGS. 2F to 2H) were cultured with cancer target cells with endogenous MUC16 expression (ovarian cancer line PEO-1) and the indicated bispecific antibodies for 96 hours.

FIG. 2A is a schematic of assay set up.

FIG. 2B is a graph showing the killing of tumor cells. The value on Y axis refers to the percentage of viable PEO1 cell.

FIG. 2C is a graph showing IFNγ release.

FIG. 2D is a graph showing CD4 T cell counts and frequency of CD25⁺ cells, represented as percentage of CD25⁺ cells in CD4 T cells.

FIG. 2E is a graph showing CD8 T cell counts and frequency of CD25⁺ cells, represented as percentage of CD25⁺ cells in CD8 T cells.

FIG. 2F is a graph showing the killing of tumor cells. The value on Y axis refers to the percentage of viable PEO1 cell.

FIG. 2G is a graph showing CD4 T cell counts and frequency of CD25⁺ cells, represented as percentage of CD25⁺ cells in CD4 T cells.

FIG. 2H is a graph showing CD4 T cell counts and CD8 T cell counts and frequency of CD25⁺ cells, represented as percentage of CD25⁺ cells in CD4 T cells and CD8 T cells.

Figure 2I:
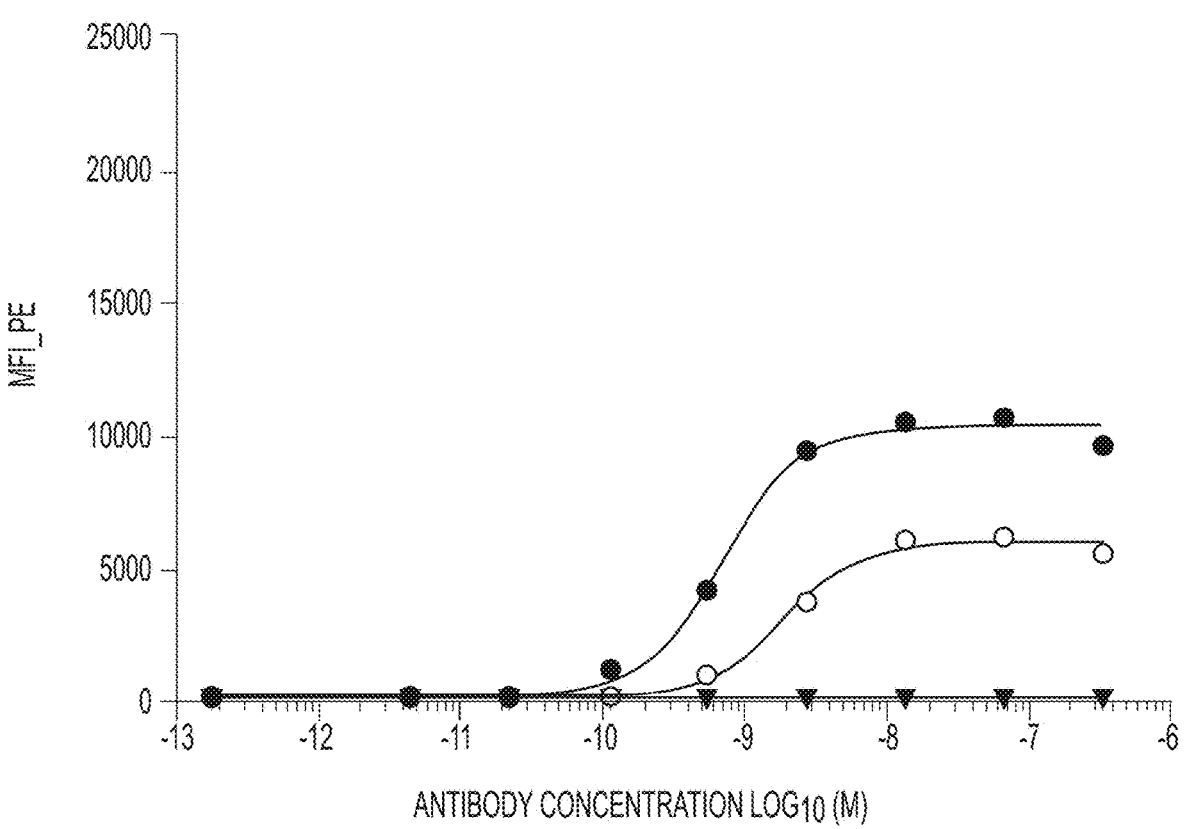

FIG. 2I is a graph showing antibody binding to cellular targets measured by flow cytometry.

Figures 3A, 3B:
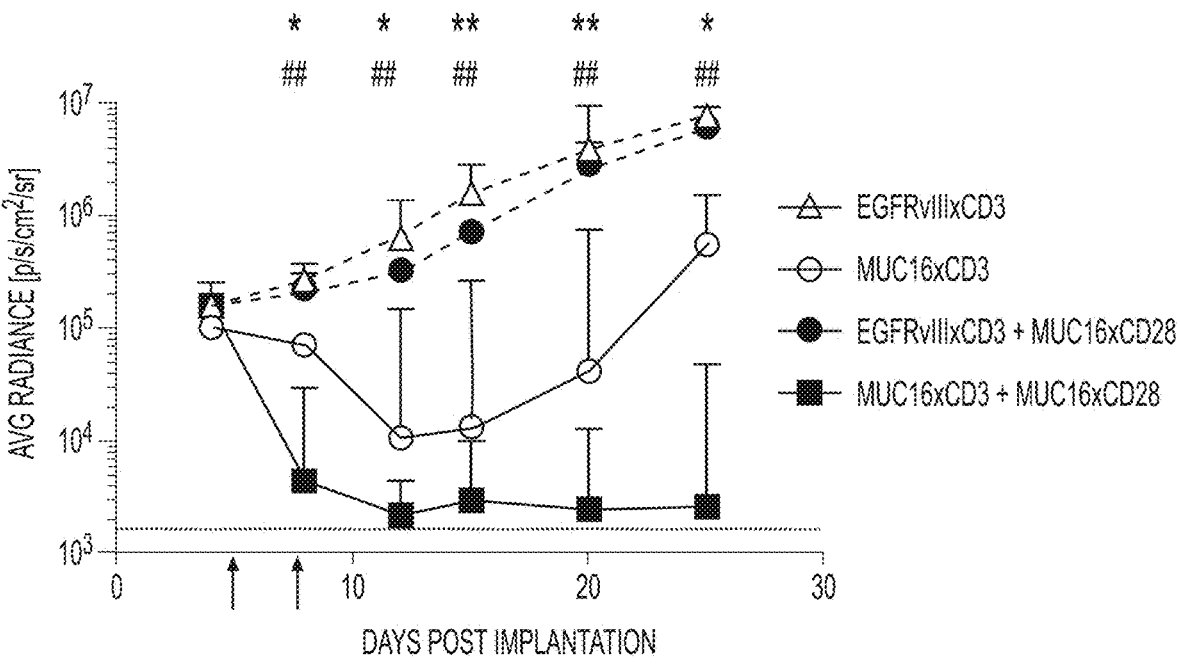
Figure 3C:
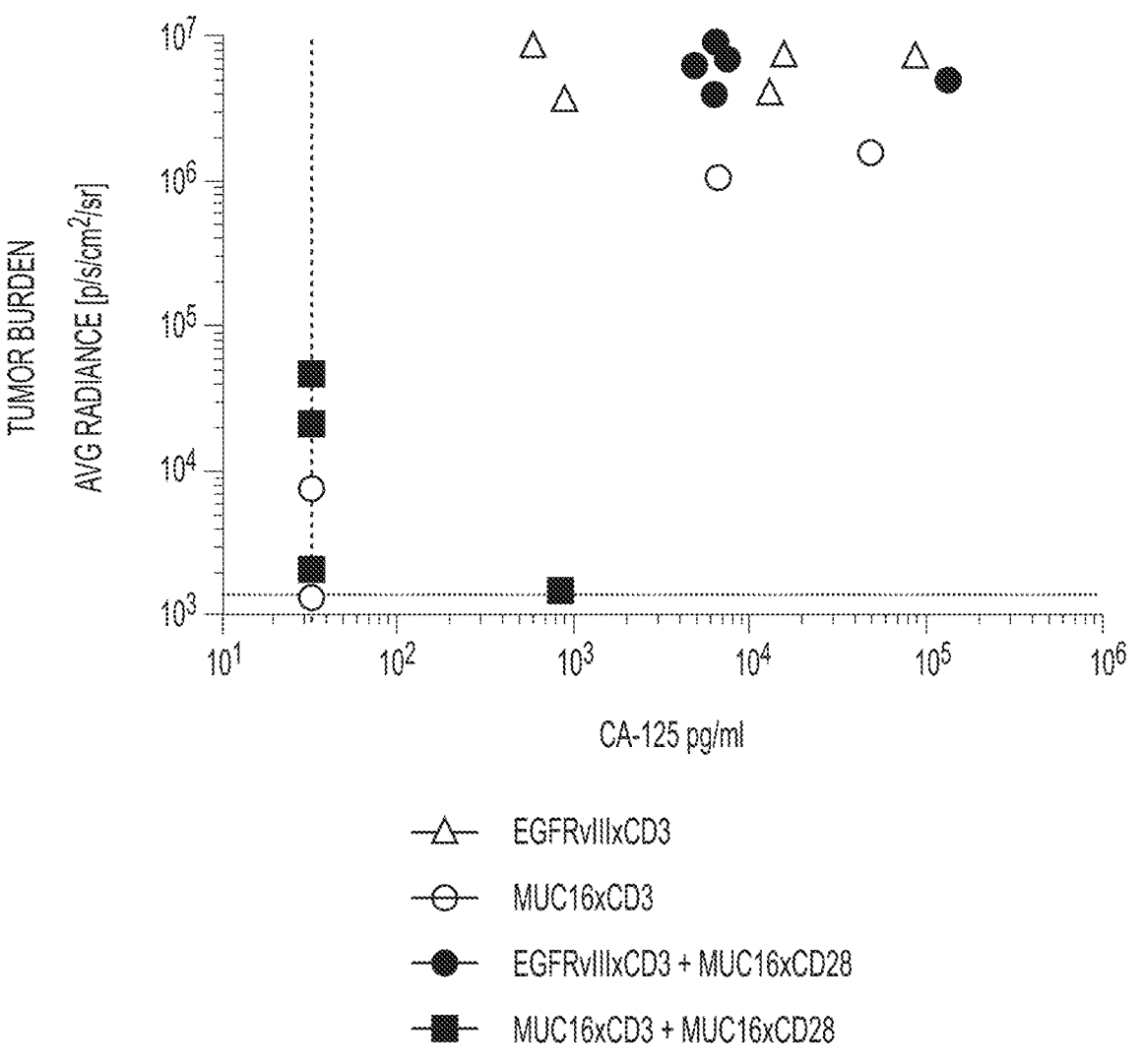

FIGS. 3A-3C are graphs showing that exemplary anti-MUC16xCD28 bispecific antibodies of the present invention enhances anti-tumor immunity by anti-MUC16xCD3 induced T cell activation.

FIG. 3A is a graph showing tumor burden as measured by average radiance (Avg Radiance [p/s/cm²/sr] over time. Values represent the group median plus range. P values were calculated with Mann Whitney test for each time point. *, p<0.05 or , p<0.01 for MUC16xCD3 and EGFRvIIIxCD3 comparison. ##, p<0.01 for MUC16xCD3+MUC16xCD28 and EGFRvIIIxCD3 comparison. Human PBMC engrafted NSG mice were implanted with OVCAR3-Luc by intraperitoneal injection. Mice were dosed with IV on Days 5 and 8 (arrows). Mice received either 2.5 µg MUC16xCD3 or 2.5 µg EGFRvIIIxCD3. Some of the mice were also administered MUC16xCD28 at 100 µg. Tumor burden was assessed by BLI on Days 4, 8, 12, 15, 20 and 25 post tumor implantation by monitoring bioluminescence over time. N=5 mice per group FIG. 3B provides graphs showing serum cytokine levels from blood obtained at the 4 hours after the first dose from the same experiments shown in FIG. 3A**. P values were calculated with one-way ANOVA. ##, p<0.01 or ####, p<0.0001 for MUC16xCD3+MUC16xCD28 and EGFRvIIIxCD3 comparison. @@@, p<0.005 for MUC16xCD3+MUC16xCD28 and MUC16xCD3 comparison. ^, p<0.01, ^^, p<0.005, ^^^^P<0.0001 for MUC16xCD3+MUC16xCD28 and EGFRvIIIxCD3+MUC16xCD28 comparison.

FIG. 3C provides graphs showing tumor burden and correlation to CA-125 levels in serum on day 26. N=5 mice per group from the same experiments shown in FIG. 3A.

Figures 4A, 4B:
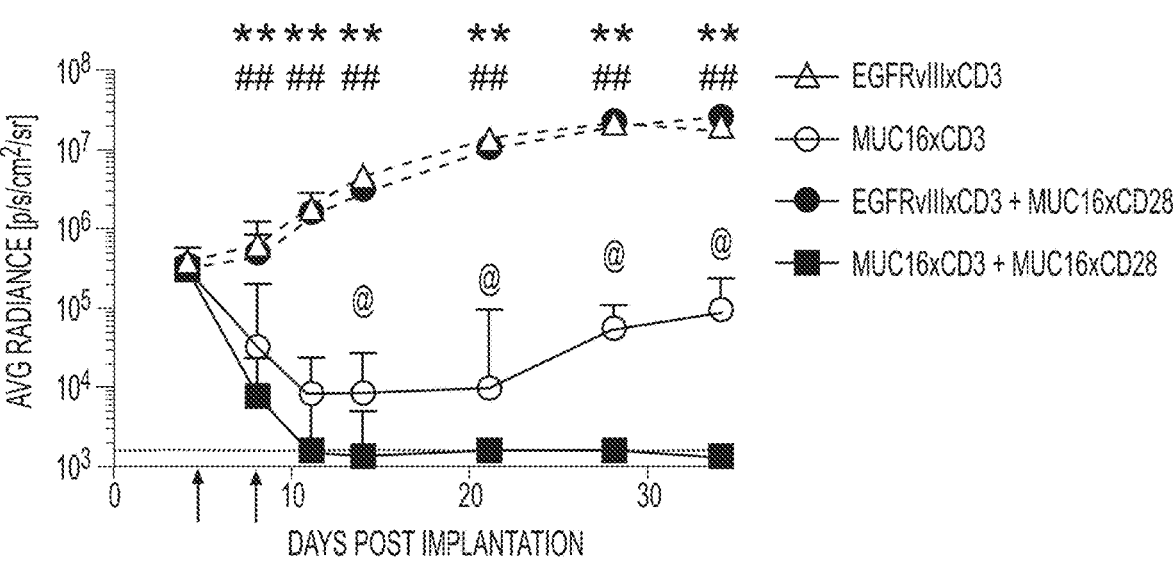

FIG. 4A is a graph showing tumor burden as measured by average radiance (Avg Radiance [p/s/cm²/sr] over time. Values represent the group median plus range. P values were calculated with Mann Whitney test for each time point. **, p<0.01 for MUC16xCD3 and EGFRvIIIxCD3 comparison. ##, p<0.01 for MUC16xCD3+MUC16xCD28 and EGFRvIIIxCD3 comparison. @, p<0.05 for MUC16xCD3+ MUC16xCD28 and MUC16xCD3 comparison. Human PBMC engrafted NSG mice were implanted with OVCAR3-

Luc by intraperitoneal injection. Mice were treated IV with 0.5 mg/kg MUC16xCD3 or 0.5 mg/kg EGFRvIIIxCD3. Some of the mice were also administered MUC16xCD28 at 0.2 mg/kg on Days 5 and 8 (arrows). Tumor burden was assessed by BLI on Days 4, 8, 11, 14, 21, 28 and 34 by monitoring bioluminescence over time. N=5 or 6 mice per group.

FIG. 4B provides graphs showing serum cytokine levels from blood obtained at the 4 hours after the first dose from the same experiments shown in FIG. 4A. P values were calculated with one-way ANOVA. *, p<0.05 for MUC16xCD3 and EGFRvIIIxCD3 comparison ##, p<0.01 or ###, p<0.001 or ####, p<0.0001 for MUC16xCD3+ MUC16xCD28 and EGFRvIIIxCD3 comparison. @, p<0.05 or @@@@, p<0.0001 for MUC16xCD3+MUC16xCD28 and MUC16xCD3 comparison. ^^, p<0.001 or ^^^P<0.001 or ^^^P<0.0001 for MUC16xCD3+MUC16xCD28 and EGFRvIIIxCD3+MUC16xCD28 comparison.

Figure 5:
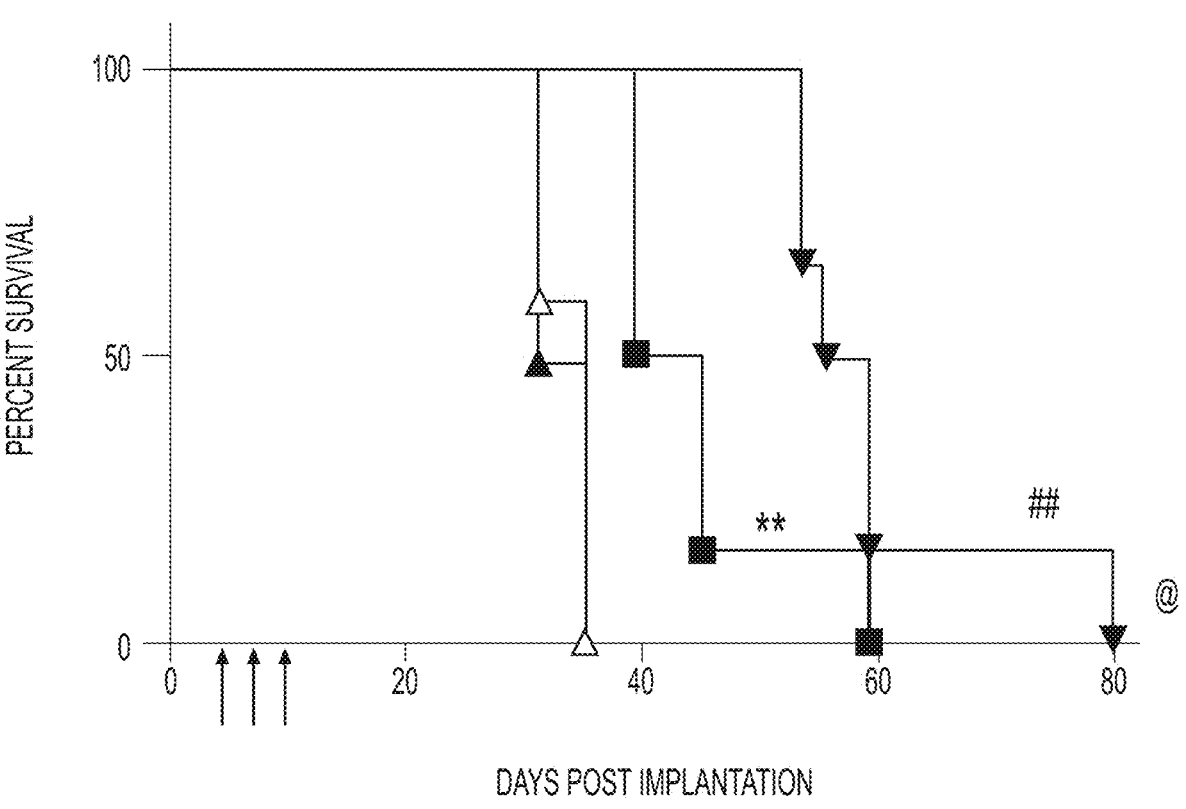

FIG. 5 is a graph showing the survival over time. ID8-VEGF/hMUC16 cells were implanted into the peritoneal cavity of mice humanized for hCD3/hCD28/hMUC16. Mice were treated intravenously with EGFRvIIIxCD3 or MUC16xCD3 at 1 mg/kg or days 3, 6, and 10 after tumor implantation, as indicated by arrows. Some mice were also administered MUC16xCD28 at 1 mg/kg. P values were calculated with Mantel-Cox test for each time point. **, p<0.01 for MUC16xCD3 and EGFRvIIIxCD3 comparison. ##, p<0.01 for MUC16xCD3+MUC16xCD28 and EGFRvIIIxCD3 comparison. @, p<0.05 for MUC16xCD3+ MUC16xCD28 and MUC16xCD3 comparison.

Figure 6A:
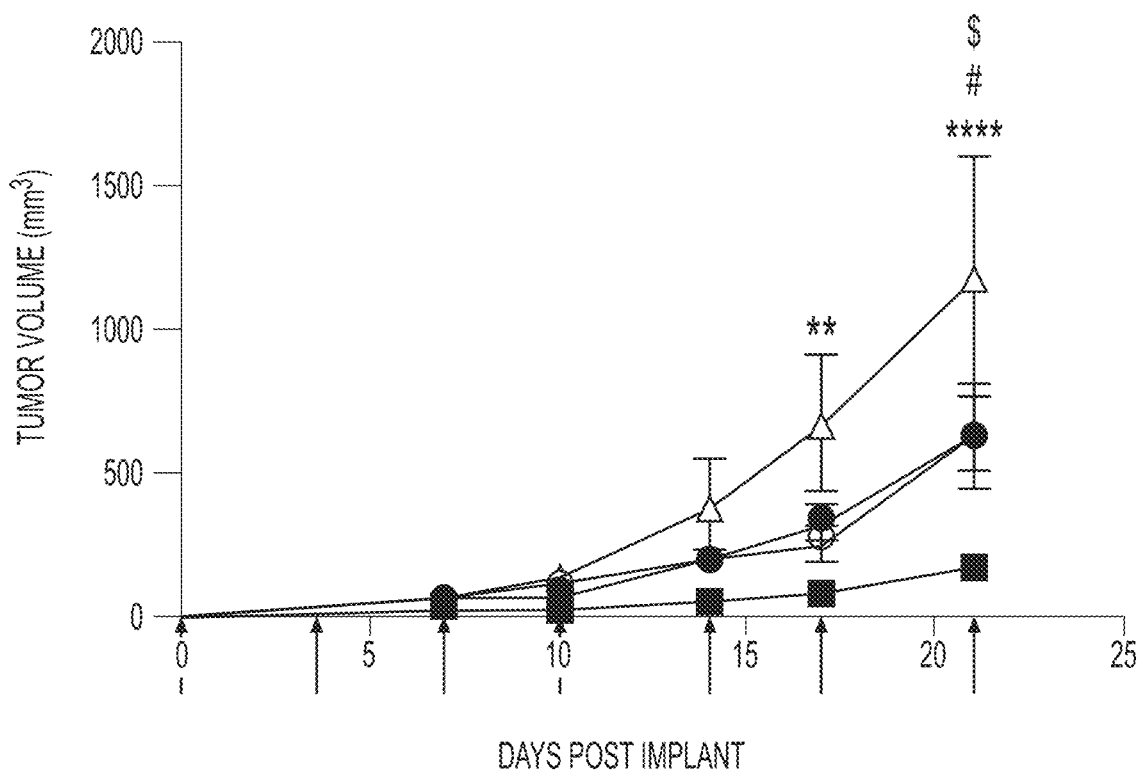

FIG. 6A is a graph showing tumor volume over time. MC38/hMUC16 tumor cells were implanted subcutaneously in hCD3/hMUC16 humanized mice. Mice were treated with anti-MUC16xCD3 at 0.01 mg/kg, exemplary anti-MUC16xmCD28 bispecific antibody of the invention at 0.5 mg/kg as indicated twice per week starting on day 0 (arrows). Tumor volume was monitored by caliper measurement over time. Values shown are the average±SEM. Data are representative of three (3) experiments. N=7 mice per group. P values were calculated with 2 way ANOVA with comparison to isotype control (, p<0.01 and **, P<0.0001 for MUC16xCD3+MUC16xmCD28 and isotype control comparison; #, p<0.05 for MUC16xCD3 and isotype control comparison; $, p<0.05 for MUC16xmCD28 and isotype control comparison).

Figure 6B:
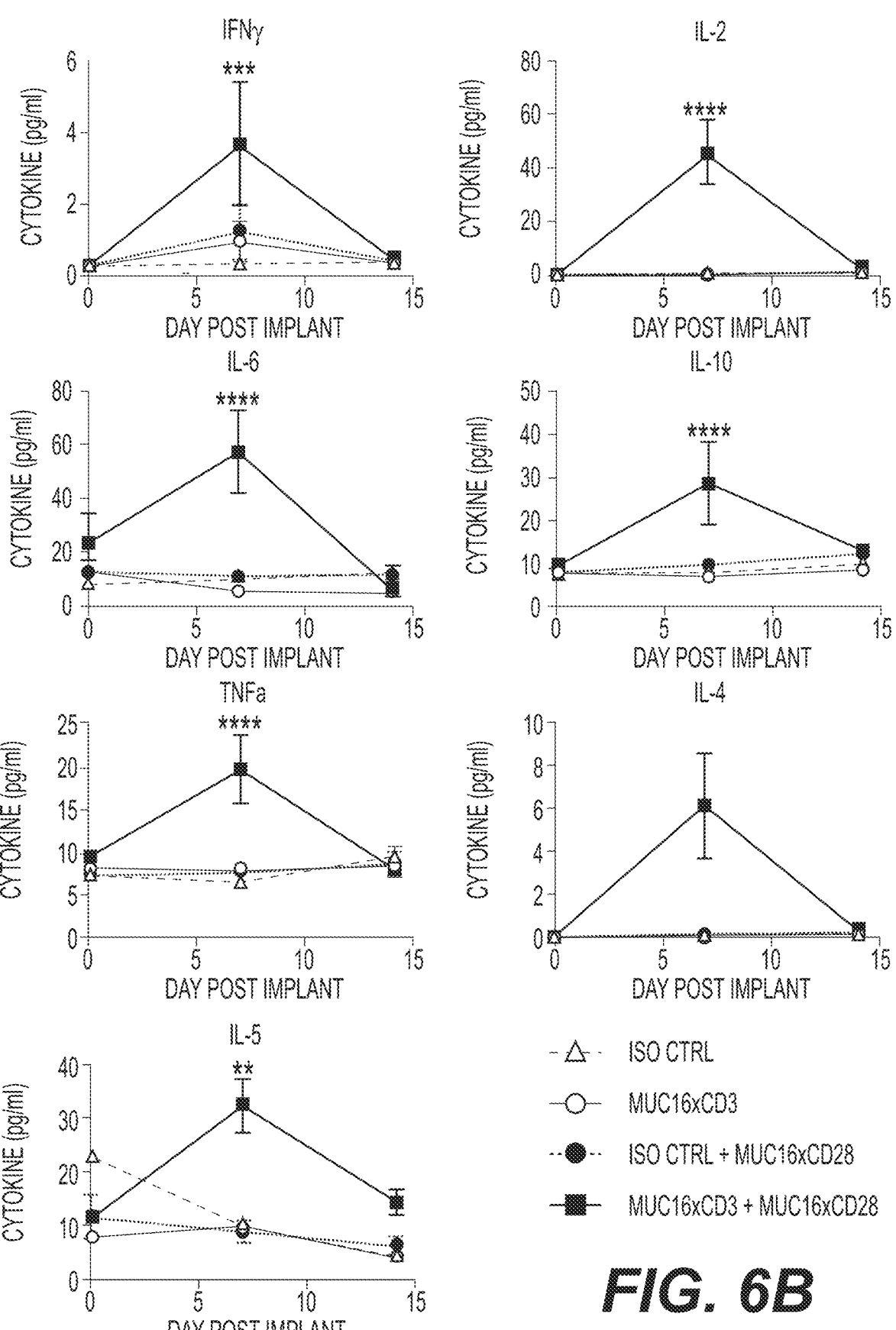

FIG. 6B provides graphs showing serum cytokine levels from blood obtained at the indicated time point from the same experiments shown in FIG. 6A.

FIGS. 6C and 6D are graphs showing cytokine levels. Mice were bled for serum cytokines at 4 hours post dose on day 7. Statistical significance was calculated with 1-way ANOVA in comparison to isotype p<0.01 and **p<0.0001. n=7 mice per group. Data is representative 3 experiments.

Figure 7:
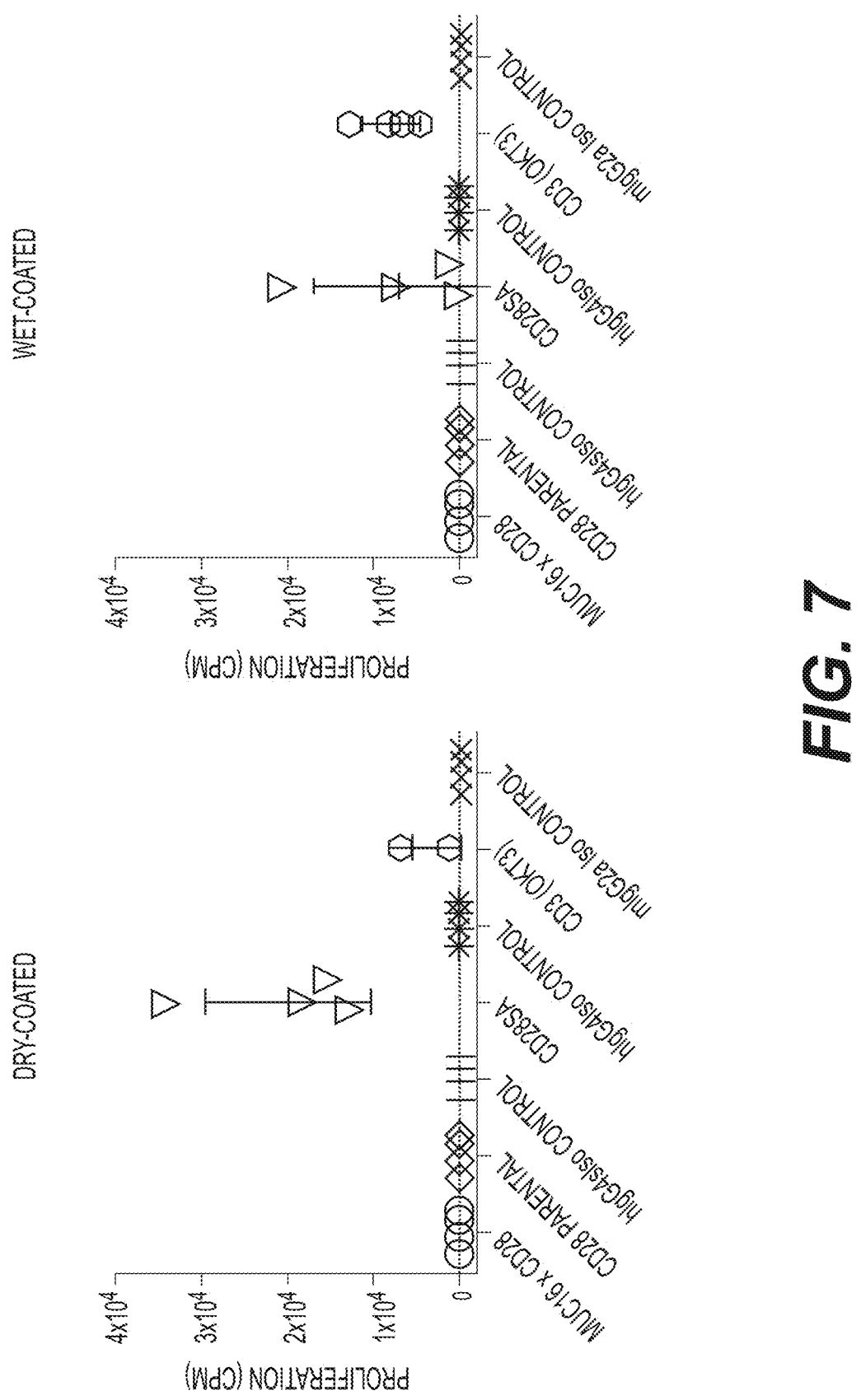

FIG. 7 is a graph showing that anchoring of a MUC16xCD28 to assay plates using dry-coating or wet-coating method does not induce T cell activation in the absence of a CD3 stimulus in contrast to CD28 superagonist.

Figure 8A:
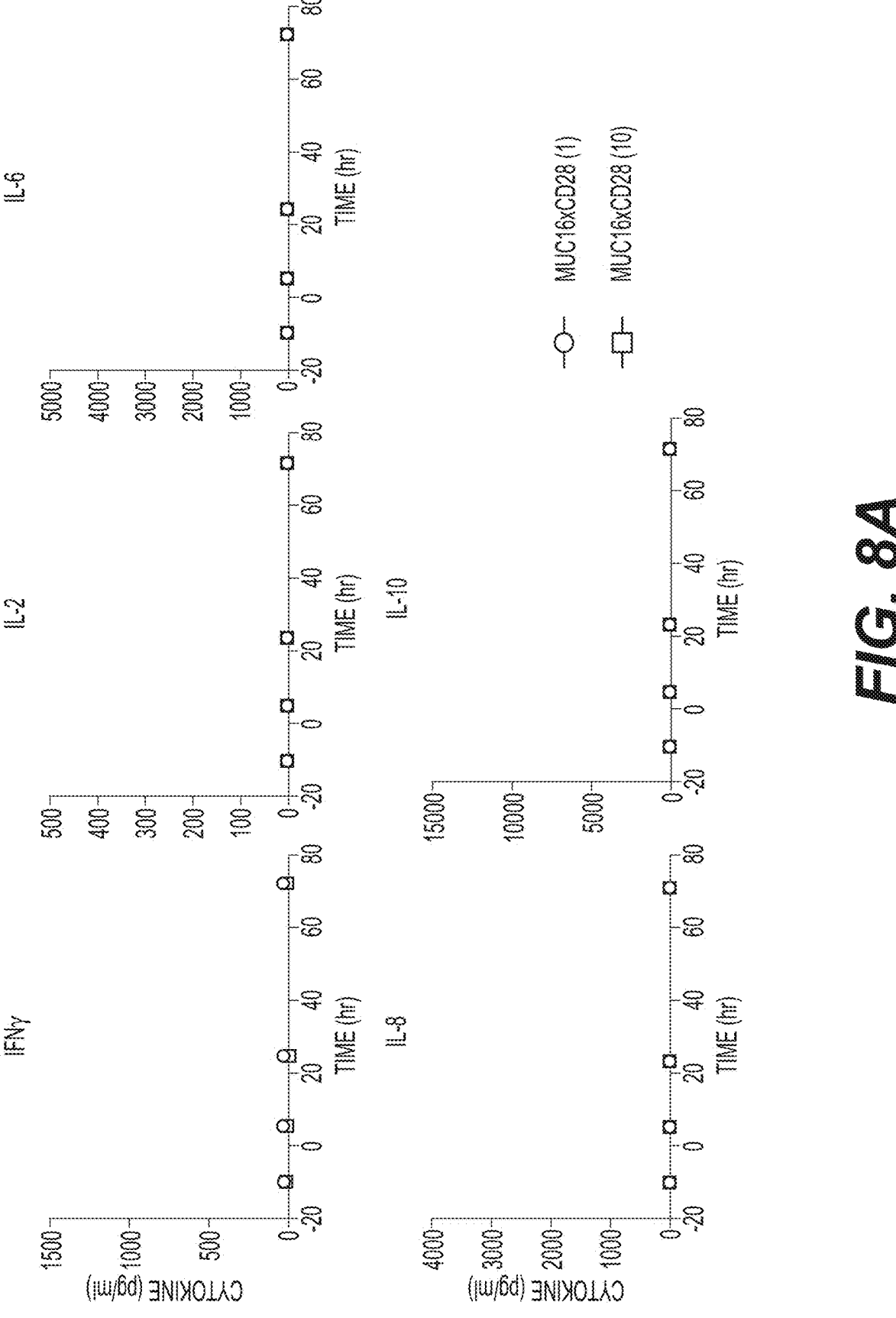
Figure 8B:
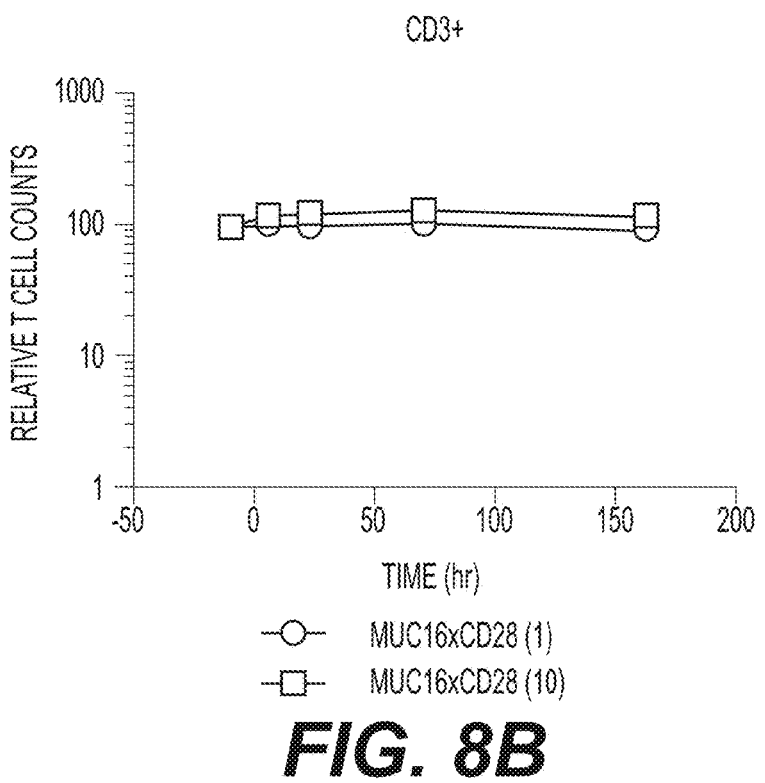
Figure 8C:
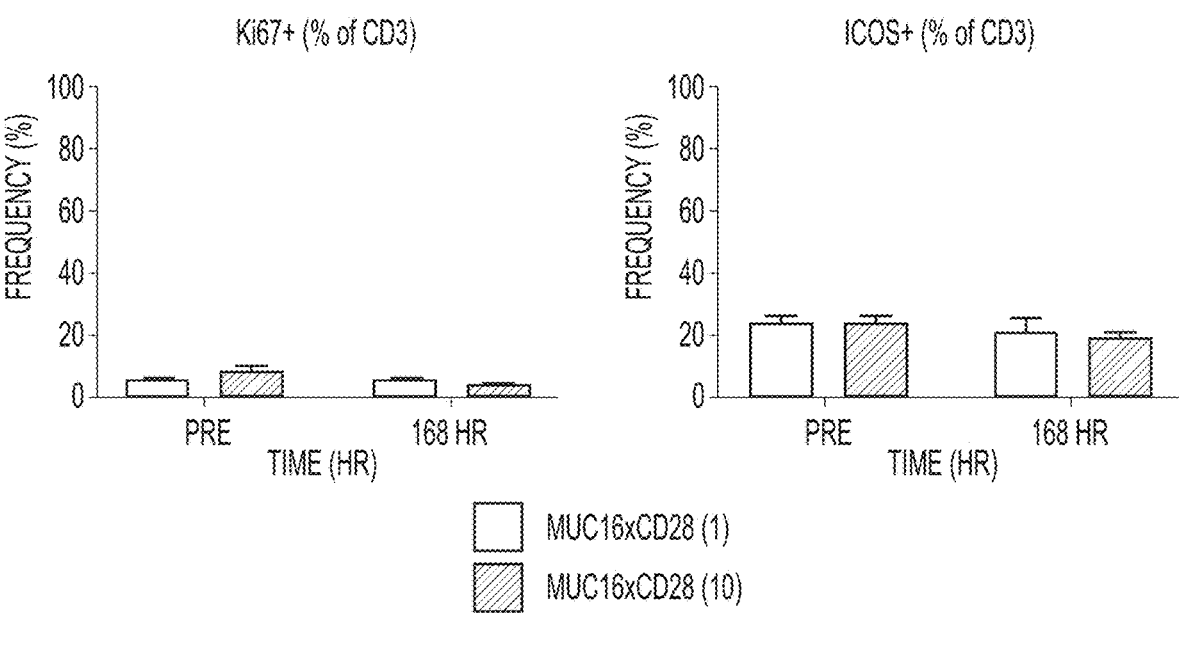

FIGS. 8A to 8C are graphs showing that MUC16xCD28 alone or in combination therapy does not induce systemic T cell activation. Cynomolgus monkeys received a single dose of bispecifics at either 1 or 10 mg/kg (indicated in parenthesis). An additional group received a total of 4 doses indicated as repeat dosing. Blood was collected at the indicated times post dose (hr). FIG. 8A: Serum cytokines, FIG. 8B: Relative T cell counts and FIG. 8C: Frequency of Ki67+ and ICOS+ T cells (% of CD3) are shown. Data represent the average +/−SEM. N=3 animals per group. P values were calculated with 2-way ANOVA with comparison to isotype control. (, p<0.01; *, p<0.001 and ****, p<0.0001).

Figures 9A, 9B:
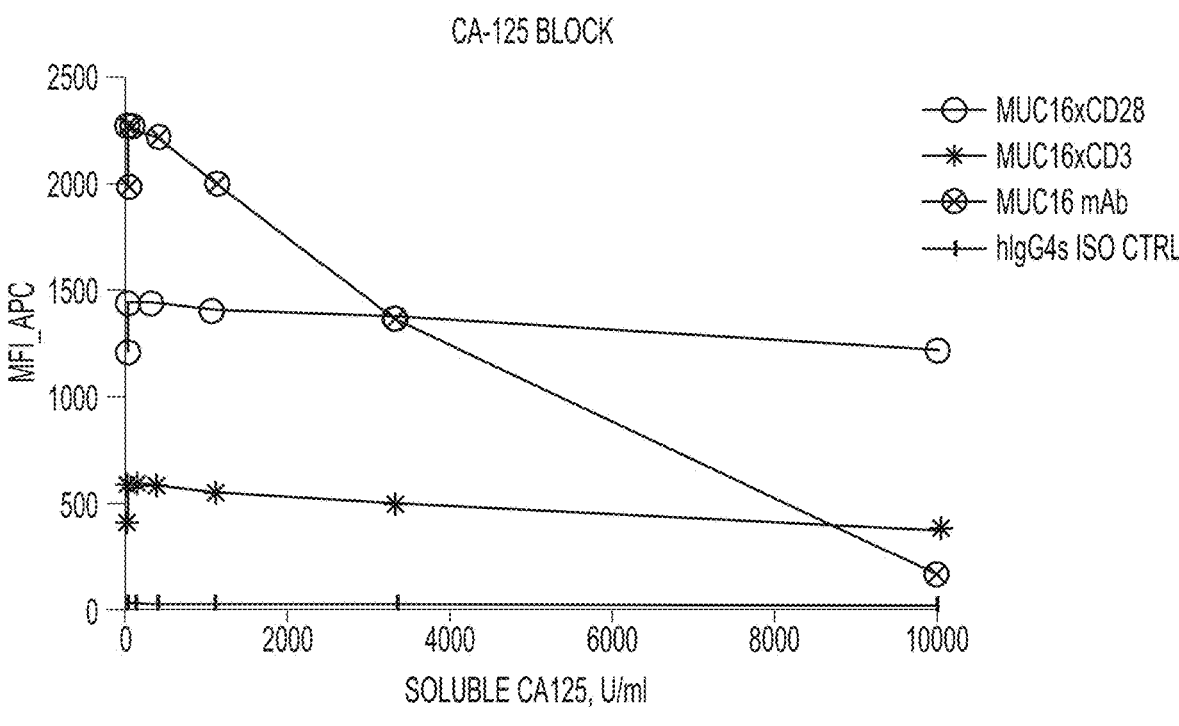

FIGS. 9A and 9B show that MUCxCD28 and MUC16xCD3 bispecific antibodies can bind to MUC-expressing cells in the presence of soluble CA-125. OVCAR-3 cells were incubated in 8 nM of indicated antibodies labeled with Alexa647 in the presence of increasing concentrations of soluble CA-125 (FIG. 9A) or MUC16 nub (FIG. 9B) for 30 minutes at 4° C. in flow cytometry buffer (PBS+1% FBS). After incubation, the cells were washed with flow cytometry buffer and analyzed by flow cytometry.

Figure 10:
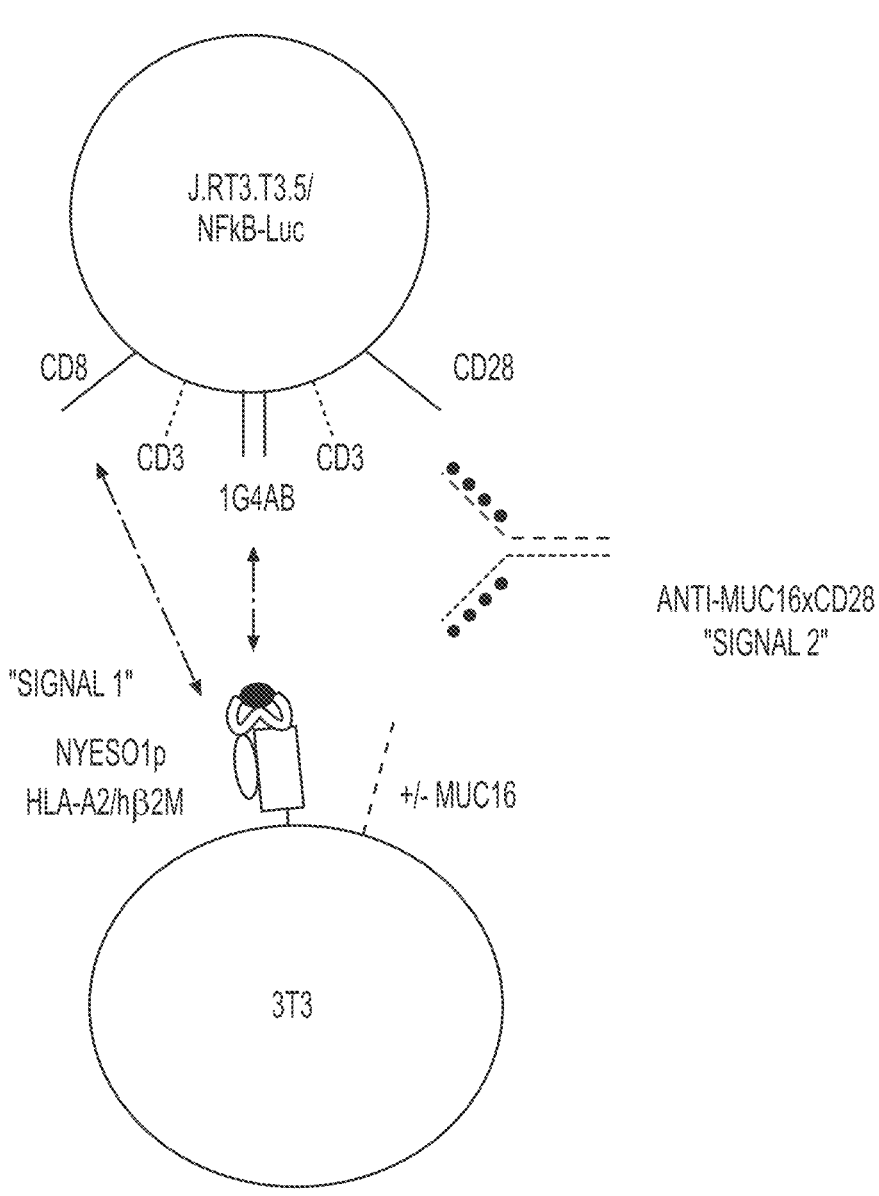

FIG. 10 is a schematic of T Cell/Antigen-presenting Cell-based Reporter Bioassay.

Figures 11A, 11B:
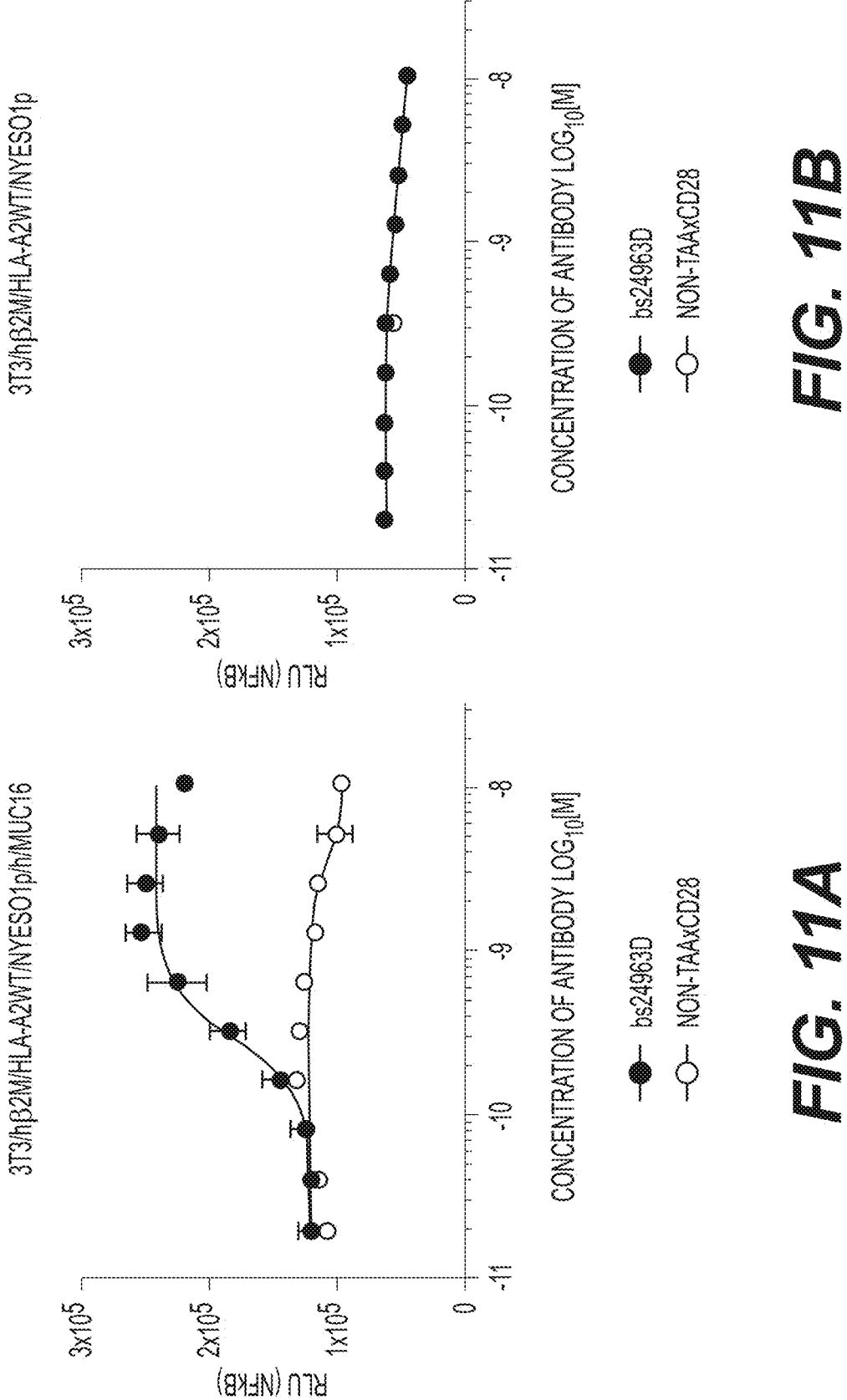

FIGS. 11A and 11B show that bs24963D (also referred to as REGN5668) enhances NF-κB signaling in engineered T cells in the presence of stimulatory antigen-presenting cells expressing MUC16. Briefly, J.RT3.T3.5/NF-κB-Luc/1G4AB/hCD8αβ/hCD28 reporter cells were incubated with bs24963D or CD28 non-bridging control bispecific antibody (non-TAAxCD28) at a range of concentrations (39 pM to 10 nM), including a no antibody control, in the presence of 3T3/hβ2M/HLA-A2/NYESO1p/hMUC16 (FIG. 11A) and 3T3/hβ2M/HLA-A2/NYESO1p cells at a 3.33:1 reporter cell to stimulatory 3T3 cell ratio (FIG. 11B). NF-κB signaling was detected as luciferase activity and measured by the quantification of luminescence signal, reported as relative light units (RLU). Data from an assay performed in duplicate wells are plotted as mean+SD.

Figure 12:
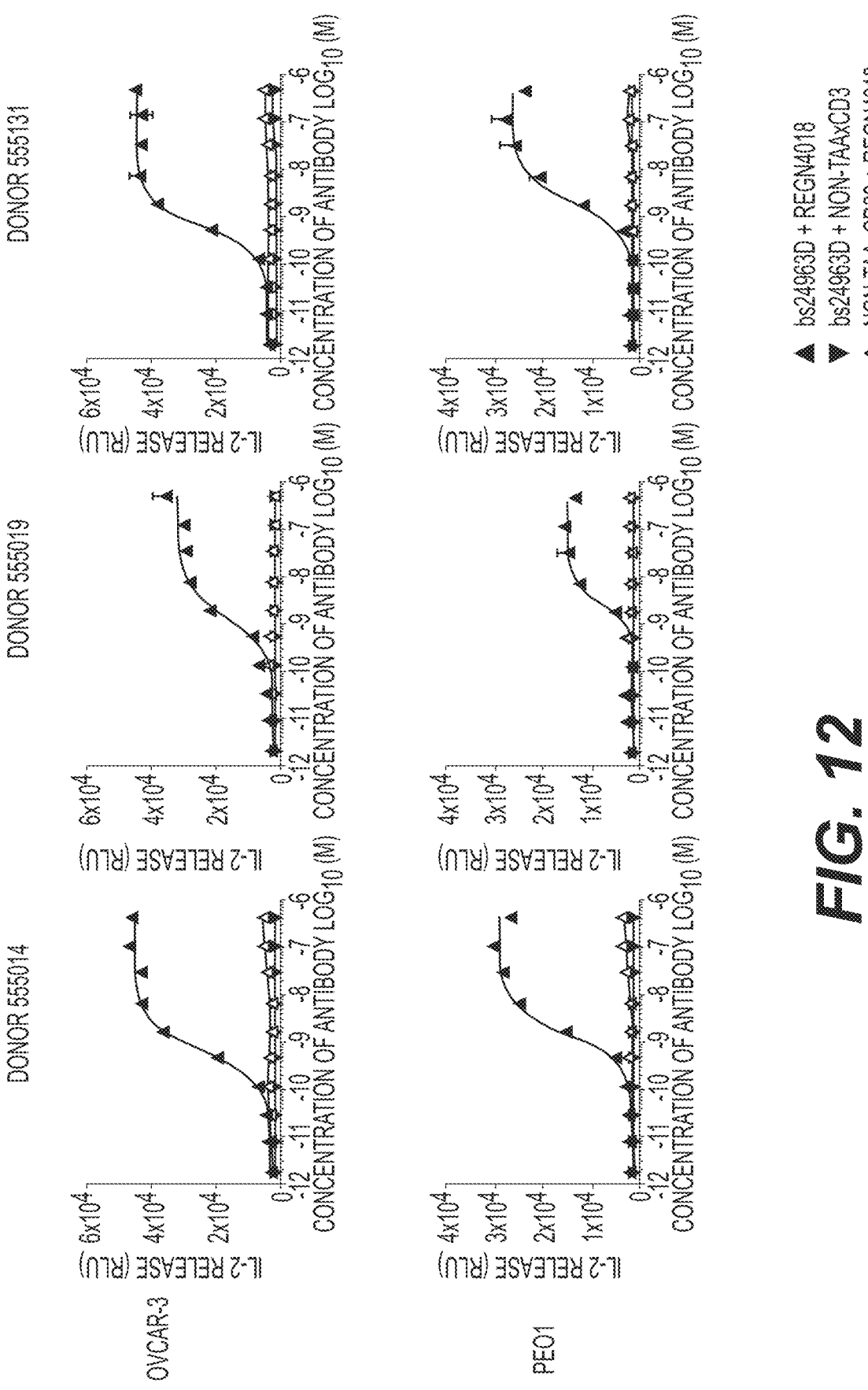

FIG. 12 shows that bs24963D (also referred to as REGN5668) mediates concentration-dependent IL-2 release from human primary T cells in the presence of REGN4018 (See WO2017/053856A1, BSMUC16/CD3-001 which is REGN4018) with OVCAR-3 and PEO1 target cells. Briefly, enriched human primary T cells were incubated with bs24963D or CD28 non-bridging control bispecific antibody (non-TAAxCD28) at a range of concentrations (7.6 pM to 500 nM), including a no antibody control, in the presence of a fixed concentration (5 nM) of either REGN4018 or CD3 non-bridging control bispecific antibody (non-TAAxCD3) and the human ovarian cancer cell lines OVCAR-3 or PEO1 at an effector to target cell ratio of 10:1 or 4:1, respectively. Data are from an assay performed in triplicate wells and are plotted as mean±SD. IL-2 release was measured using a human IL-2 immunoassay according to the manufacturer's protocol.

Figure 13:
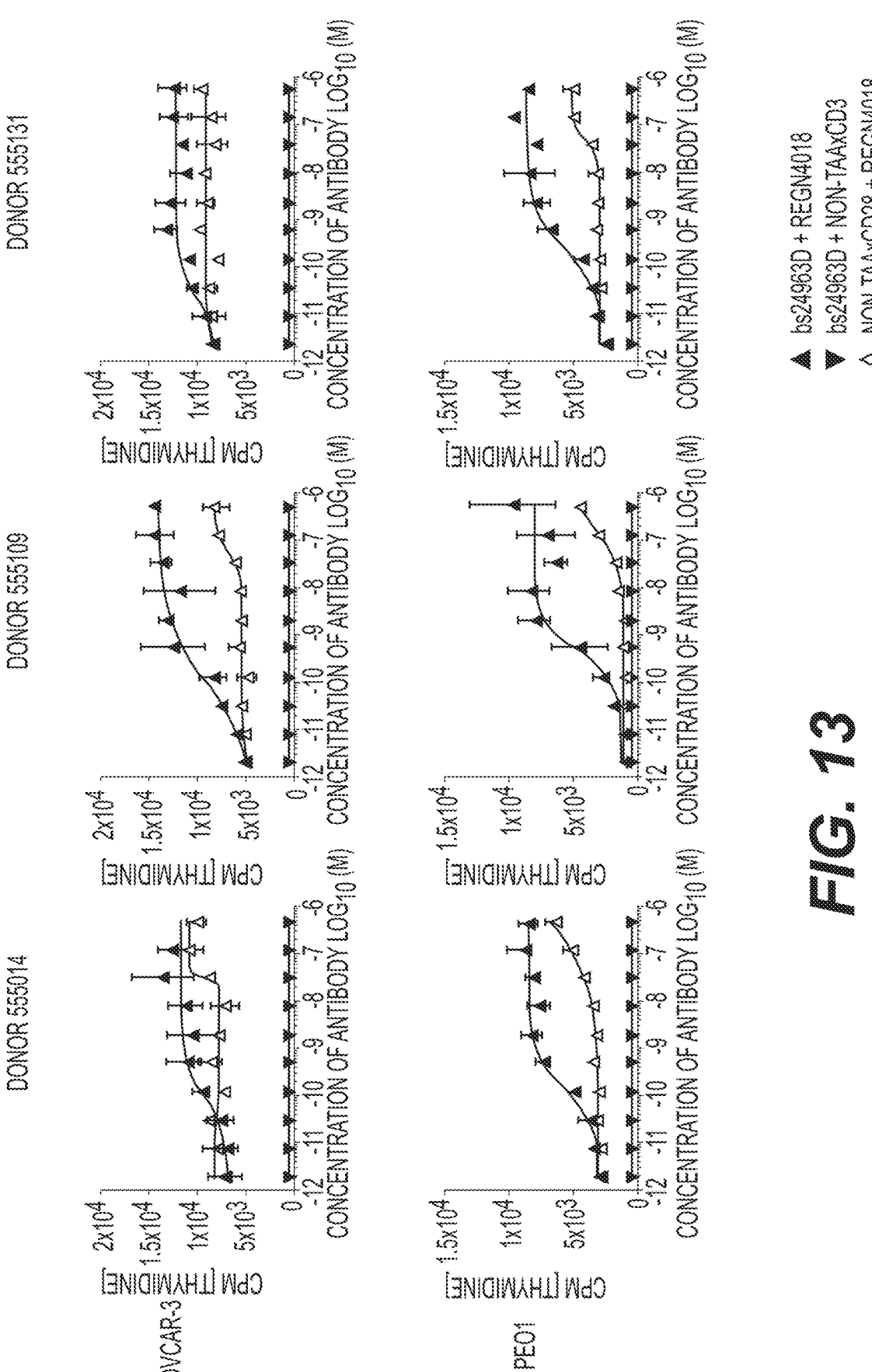

FIG. 13 shows thet bs24963D (also referred to as REGN5668) mediates concentration-dependent enhancement of proliferation of human primary T cells in the presence of REGN4018 with OVCAR-3 and PEO1 target cells. Briefly, enriched human primary T cells were incubated with bs24963D or CD28 non-bridging control bispecific antibody (non-TAAxCD28) at a range of concentrations (7.6 pM to 500 nM), including a no antibody control, in the presence of a fixed concentration (5 nM) of either REGN4018 or CD3 non-bridging control bispecific antibody (non-TAAxCD3) and the human ovarian cancer cell lines OVCAR-3 and PEO1 at an effector to target cell ratio of 10:1 or 4:1, respectively. Data are from an assay performed in triplicate wells and are plotted as mean±SD. T-cell proliferation was measured via detection of tritium decay (from tritiated thymidine incorporated into dividing cells) and reported as CPM.

Figure 14:
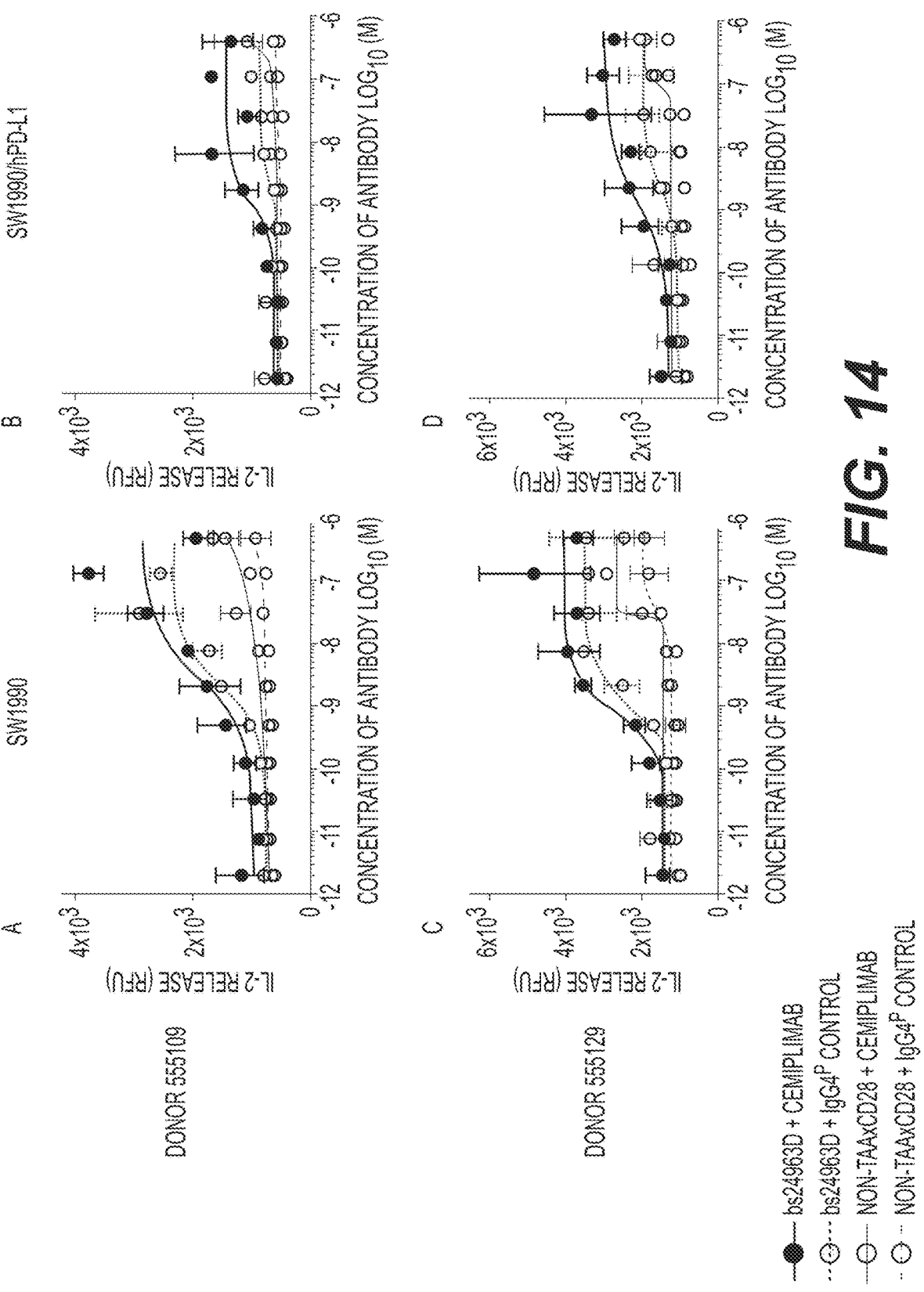

FIG. 14 shows that bs24963D (also referred to as REGN5668) mediates concentration-dependent IL-2 release and the addition of cemiplimab modestly increases IL-2 release from human primary T cells with SW1990 and SW1990/hPD-L1 target cells. Briefly, enriched human primary T cells were incubated with bs24963D or CD28 non-bridging control bispecific antibody (non-TAAxCD28) at a range of concentrations (7.6 pM to 500 nM), including a no antibody control, in the presence of a fixed concentration (20 nM) of either cemiplimab or IgG4P control and the SW1990 and SW1990/hPD-L1 human pancreatic cancer cell lines at an effector to target cell ratio of 2:1. Data are from an assay performed in triplicate wells and are plotted as mean±SD. IL-2 release was measured using a human IL-2 immunoassay according to the manufacturer's protocol. Statistical analyses were performed using a 2-way ANOVA. Differences were considered statistically significant when p<0.05. bs24963D+cemiplimab demonstrated statistically significant increases in IL-2 release compared with REGN5668+IgG4$^P$ control in SW1990/hPD-L1 cells (p<0.0001).

Figure 15:
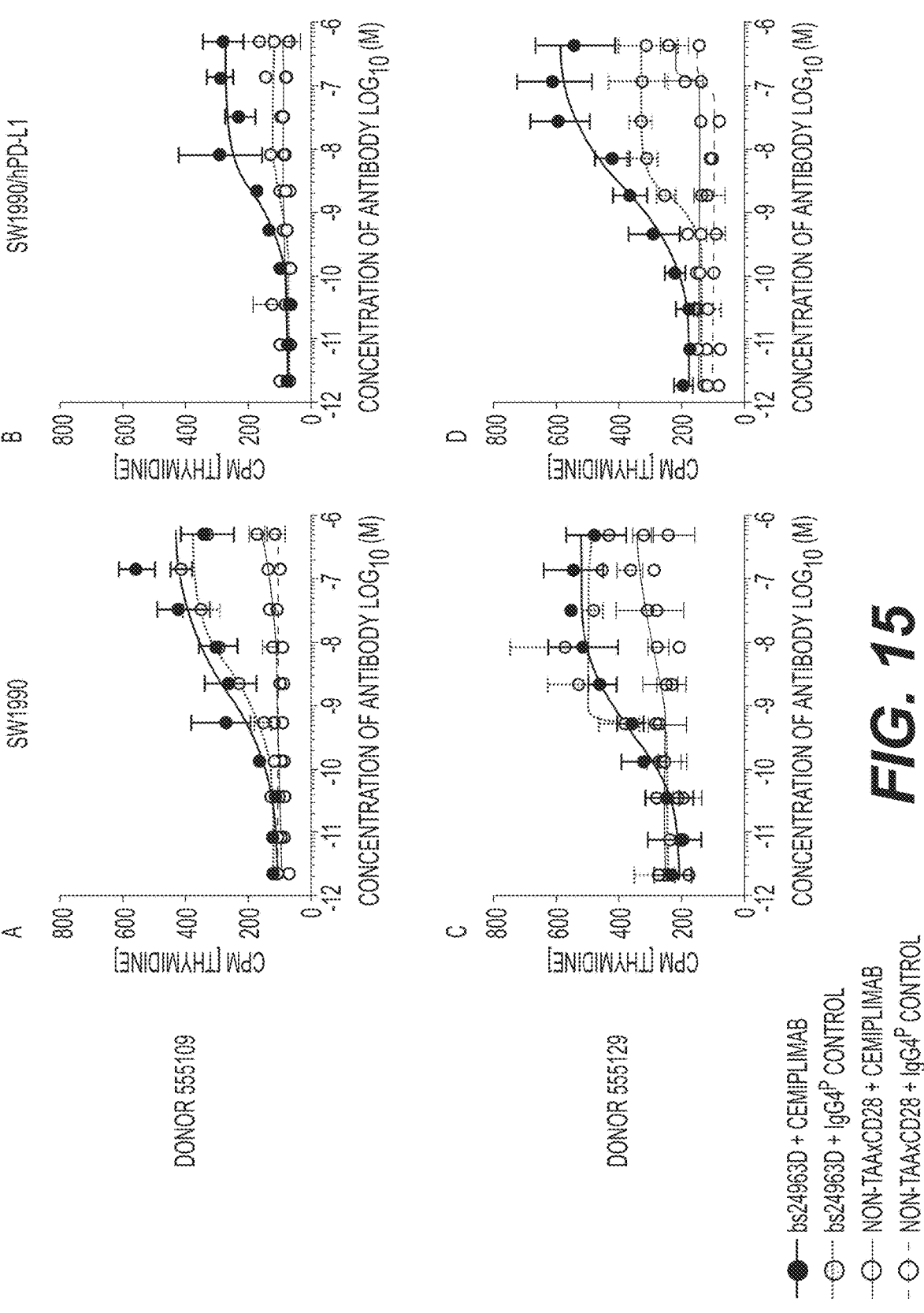

FIG. 15 shows that bs24963D (also referred to as REGN5668) mediates concentration-dependent enhancement of proliferation and the addition of cemiplimab modesty increases proliferation of human primary T cells with SW1990 and SW1990/hPD-L1. Briefly, enriched human primary T cells were incubated with bs24963D or CD28 non-bridging control bispecific antibody (non-TAAxCD28) at a range of concentrations (7.6 pM to 500 nM), including a no antibody control, in the presence of a fixed concentration (20 nM) of either cemiplimab or IgG4P control and the SW1990 and SW1990/hPD-L1 human pancreatic cancer cell lines at an effector to target cell ratio of 2:1. Data are from an assay performed in triplicate wells and are plotted as mean±SD. T-cell proliferation was measured via detection of tritium decay (from tritiated thymidine incorporated into dividing cells) and reported as CPM. Statistical analyses were performed using a 2-way ANOVA. Differences were considered statistically significant when p<0.05. bs24963D+cemiplimab demonstrated statistically significant increases in proliferation compared with bs24963D+IgG4$^P$ control in SW1990/hPD-L1 cells (p<0.0001).

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "CD28," as used herein, refers to an antigen which is expressed on T cells as a costimulatory receptor. Human CD28 comprises the amino acid sequence as set forth in SEQ ID NO: 50, and/or having the amino acid sequence as set forth in NCBI accession No. NP_006130.1. The human CD28 ecto domain (N19-P152) having a mouse Fc is shown in SEQ ID NO: 52. The human CD28 ecto domain (N19-P152) having a myc-myc-his tag is shown in SEQ ID NO: 53. All references to proteins, polypeptides and protein fragments herein are intended to refer to the human version of the respective protein, polypeptide or protein fragment unless explicitly specified as being from a non-human species. Thus, the expression "CD28" means human CD28 unless specified as being from a non-human species, e.g., "mouse CD28," "monkey CD28," etc. Mouse CD28 (Accession number NP_031668.3) ecto domain having a myc-myc-his tag is shown in SEQ ID NO: 54.

As used herein, "an antibody that binds CD28" or an "anti-CD28 antibody" includes antibodies and antigen-binding fragments thereof that specifically recognize a monomeric CD28, as well as antibodies and antigen-binding fragments thereof that specifically recognize a dimeric CD28. The antibodies and antigen-binding fragments of the present invention may bind soluble CD28 and/or cell surface expressed CD28. Soluble CD28 includes natural CD28 proteins as well as recombinant CD28 protein variants such as, e.g., monomeric and dimeric CD28 constructs, that lack a transmembrane domain or are otherwise unassociated with a cell membrane.

As used herein, the expression "cell surface-expressed CD28" means one or more CD28 protein(s) that is/are expressed on the surface of a cell in vitro or in vivo, such that at least a portion of a CD28 protein is exposed to the extracellular side of the cell membrane and is accessible to an antigen-binding portion of an antibody. "Cell surface-expressed CD28" includes CD28 proteins contained within the context of a functional T cell costimulatory receptor in the membrane of a cell. The expression "cell surface-expressed CD28" includes CD28 protein expressed as part of a homodimer on the surface of a cell. A "cell surface-expressed CD28" can comprise or consist of a CD28 protein expressed on the surface of a cell which normally expresses CD28 protein. Alternatively, "cell surface-expressed CD28" can comprise or consist of CD28 protein expressed on the surface of a cell that normally does not express human CD28 on its surface but has been artificially engineered to express CD28 on its surface.

As used herein, the expression "anti-CD28 antibody" includes both monovalent antibodies with a single specificity, as well as bispecific antibodies comprising a first arm that binds CD28 and a second arm that binds a second (target) antigen, wherein the anti-CD28 arm comprises any of the HCVR/LCVR or CDR sequences as set forth in Table 3 herein. Examples of anti-CD28 bispecific antibodies are described elsewhere herein. The term "antigen-binding molecule" includes antibodies and antigen-binding fragments of antibodies, including, e.g., bispecific antibodies.

The term "MUC16," as used herein, refers to the human MUC16 protein unless specified as being from a non-human species (e.g., "mouse MUC16," "monkey MUC16," etc.). The human MUC16 protein has the amino acid sequence shown in SEQ ID NO:49, and/or having the amino acid sequence as set forth in NCBI accession No. NP_078966. The human MUC16 membrane proximal domain (P13810-P14451) having a myc-myc-his tag is shown as SEQ ID NO: 51.

As used herein, "an antibody that binds MUC16" or an "anti-MUC16 antibody" includes antibodies and antigen-binding fragments thereof that may bind soluble MUC16 and/or cell surface expressed MUC16. Soluble MUC16 includes natural MUC16 proteins as well as recombinant MUC16 protein variants such as, e.g., MUC16 constructs, that lack a transmembrane domain or are otherwise unassociated with a cell membrane.

As used herein, the expression "anti-MUC16 antibody" includes both monovalent antibodies with a single specificity, as well as bispecific antibodies comprising a first arm that binds MUC16 and a second arm that binds a second (target) antigen, wherein the anti-MUC16 arm comprises any of the HCVR/LCVR or CDR sequences as set forth in Table 1 herein. Examples of anti-MUC16 bispecific antibodies are described elsewhere herein. The term "antigen-binding molecule" includes antibodies and antigen-binding fragments of antibodies, including, e.g., bispecific antibodies.

The term "antigen-binding molecule" includes antibodies and antigen-binding fragments of antibodies, including, e.g., bispecific antibodies.

The term "antibody", as used herein, means any antigen-binding molecule or molecular complex comprising at least one complementarity determining region (CDR) that specifically binds to or interacts with a particular antigen (e.g., CD28). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, $C_H1$, $C_H2$ and $C_H3$. Each light chain comprises a light chain variable region (abbreviated herein as LCVR or VL) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-CD28 and/or anti-MUC16 antibody (or antigen-binding portion thereof) may be identical to the human germ line sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-CD28 and/or anti-MUC16 antibodies of the invention (monospecific or bispecific) are human antibodies. The term "human antibody", as used herein, is intended to include antibodies having variable and constant regions derived from human germ line immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germ line of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germ line $V_H$ and $V_L$ sequences, may not naturally exist within the human antibody germ line repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, CH2 or CH3 region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention also includes one-arm antibodies that bind CD28 and/or MUC16. As used herein, a "one-arm antibody" means an antigen-binding molecule comprising a single antibody heavy chain and a single antibody light chain. The one-arm antibodies of the present invention may comprise any of the HCVR/LCVR or CDR amino acid sequences as set forth in Table 1 and Table 3.

The anti-CD28 and/or anti-MUC16 antibodies herein, or the antigen-binding domains thereof, may comprise one or more amino acid substitutions, insertions and/or deletions in the framework and/or CDR regions of the heavy and light chain variable domains as compared to the corresponding germline sequences from which the antigen-binding proteins or antigen-binding domains were derived. Such mutations can be readily ascertained by comparing the amino acid sequences disclosed herein to germline sequences available from, for example, public antibody sequence databases. The present invention includes antibodies, and the antigen-binding domains thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments, which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies, or the antigen-binding domains thereof, of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies, or the antigen-binding fragments thereof, that contain one or more germline mutations can be easily tested for one or more desired property such as, improved binding specificity, increased binding affinity, improved or enhanced antagonistic or agonistic biological properties (as the case may be), reduced immunogenicity, etc. Antibodies, or the antigen-binding fragments thereof, obtained in this general manner are encompassed within the present invention.

The present invention also includes anti-CD28 and/or MUC16 antibodies and antigen-binding molecules comprising variants of any of the HCVR, LCVR, and/or CDR amino acid sequences disclosed herein. Exemplary variants included within this aspect of the invention include variants of any of the HCVR, LCVR, and/or CDR amino acid sequences disclosed herein having one or more conservative substitutions. For example, the present invention includes anti-CD28 antibodies and antigen-binding molecules having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 3 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et a/. (1992) Science 256: 1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et a/. (1997) Nucleic Acids Res. 25:3389-402.

Bispecific Antigen-Binding Molecules

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-CD28 and/or anti-MUC16 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

Use of the expression "anti-CD28 antibody" and/or "anti-MUC16 antibody" herein is intended to include both mono-specific anti-CD28 and/or anti-MUC16 antibodies as well as bispecific antibodies comprising a CD28-binding arm or MUC16-binding arm and a second arm that binds a target antigen. Thus, the present invention includes bispecific antibodies wherein one arm of an immunoglobulin binds human CD28 or MUC16, and the other arm of the immunoglobulin is specific for a target antigen. The target antigen that the other arm of the CD28 or MUC16 bispecific antibody binds can be any antigen expressed on or in the vicinity of a cell, tissue, organ, microorganism or virus, against which a targeted immune response is desired. The CD28-binding arm can comprise any of the HCVR/LCVR or CDR amino acid sequences as set forth in Table 3 herein. The MUC16-binding arm can comprise any of the HCVR/LCVR or CDR amino acid sequences as set forth in Table 1 herein. In certain embodiments, the CD28-binding arm binds human CD28 and induces human T cell proliferation.

In the context of bispecific antibodies of the present invention wherein one arm of the antibody binds CD28 and the other arm binds a target antigen, the target antigen can be a tumor-associated antigen, such as MUC16.

According to certain exemplary embodiments, the present invention includes bispecific antigen-binding molecules that specifically bind CD28 and MUC16. Such molecules may be referred to herein as, e.g., "anti-CD28/anti-MUC16," or "anti-CD28xMUC16," or "CD28xMUC16" or "anti-MUC16/anti-CD28," or "anti-MUC16xCD28," or "MUC16xCD28" bispecific molecules, or other similar terminology.

According to certain exemplary embodiments as shown in the Figures, the bispecific antigen-binding molecules (e.g., bispecific antibody) may have an effector arm and a targeting arm. The effector arm may be the first antigen-binding domain (e.g., anti-CD28 antibody) that binds to the antigens on effector cells (e.g., T cells). The targeting arm may be the second antigen binding domain (e.g., anti-MUC16 antibody) that binds to the antigens on target cells (e.g., tumor cells). According to certain exemplary embodiments, the effector arm binds to CD28 and the targeting arm binds to MUC16. The bispecific anti-CD28/MUC16 may provide co-stimulatory signal to effector cells (e.g., T cells). The effector arm has no effect to stimulate T cells without clustering. Upon clustering, the effector arm alone has little effect to stimulate T cells. In combination with the targeting arm, the effector arm stimulates T cells. The tumor targeting arm may have imperfect tumor specificity. The antigen that is the target of the targeting arm (e.g., MUC16) may be expressed on a fraction of tumor cells. The specificity of the tumor targeting arm may be increased by overlapping with combination with anti-CD3 bispecific antigen-binding molecules (e.g., anti-CD3/MUC16 bispecific antibody).

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., CD28), and the second antigen-binding domain specifically binds a second, distinct antigen (e.g., MUC16).

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen binding domain (e.g., a bispecific antibody), the CDRs of the first antigen-binding domain may be designated with the prefix "D" and the CDRs of the second antigen-binding domain may be designated with the prefix "D2". Thus, the CDRs of the first antigen-binding domain may be referred to herein as D1-HCDR1, D1-HCDR2, and D1-HCDR3; and the CDRs of the second antigen-binding domain may be referred to herein as D2-HCDR1, D2-HCDR2, and D2-HCDR3.

The first antigen-binding domain and the second antigen-binding domain may be directly or indirectly connected to one another to form a bispecific antigen-binding molecule of the present invention. Alternatively, the first antigen-binding domain and the second antigen binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of 1 to about 200 amino acids in length containing at least one cysteine residues. In other embodiments, the multimerizing domain is a cysteine residue, or a short cysteine containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (OVO)-Ig, Quadroma, knobs-into-holes, common light chain (e.g., common light chain with knobs-into-holes, etc.), CrossMab, CrossFab, (SEEO)body, leucine zipper, Ouobody, IgG1/IgG2, dual acting Fab (OAF)-IgG, and Mab² bispecific formats (see, e.g., Klein et a/. 2012, mAbs 4:6, 1-11, and references cited therein, for a review of the foregoing formats).

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., LN/FIW or T), 254 (e.g., S or T), and 256 (e.g., S/R/Q/EID or T); or a modification at position 428 and/or 433 (e.g., UR/S/P/Q or K) and/or 434 (e.g., H/F or V); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252,254, and 256 (e.g., 252Y, 254T, and 256E) modification; a 250Q and 428L modification (e.g., T250Q and M428L); and a 307 and/or 308 modification (e.g., 308F or 308P).

The present invention also includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L 18M, N44S, K52N, V57M, and V821 (by IMGT; D356E, L358M, N384S, K392N, V397M, and V4221 by EU) in the case of IgG1 antibodies; N44S, K52N, and V821 (IMGT; N384S, K392N, and V4221 by EU) in the case of IgG2 antibodies; and Q15R, N44S, K52N, V57M, R69K, E79Q, and V821 (by IMGT; Q355R, N384S, K392N, V397M, R409K, E419Q, and V4221 by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 CH2]-[IgG4 $C_H3$]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 $C_H2$]-[IgG1 $C_H3$]. These and other examples of chimeric Fc domains that can be included in any of the antigen-binding molecules of the present invention are described in WO2014/022540 A1, Chimeric Fc domains having these general structural arrangements, and variants thereof, can have altered Fc receptor binding, which in turn affects Fc effector function.

Sequence Variants

The antibodies and bispecific antigen-binding molecules of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germ line sequences available from, for example, public antibody sequence databases. The antigen-binding molecules of the present invention may comprise antigen binding fragments which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germ line sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germ line sequence while certain other residues that differ from the original germ line sequence are maintained or are mutated to the corresponding residue of a different germline sequence. Once obtained, antigen-binding domains that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

The present invention also includes antigen-binding molecules wherein one or both antigen-binding domains comprise variants of any of the HCVR, LCVR, and/or CDR amino acid sequences disclosed herein having one or more conservative substitutions. For example, the present invention includes antigen-binding molecules comprising an antigen-binding domain having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

The present invention also includes antigen-binding molecules comprising an antigen binding domain with an HCVR, LCVR, and/or CDR amino acid sequence that is substantially identical to any of the HCVR, LCVR, and/or CDR amino acid sequences disclosed herein. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

pH-Dependent Binding

The present invention includes anti-CD28/anti-MUC16 bispecific antigen-binding molecules, with pH-dependent binding characteristics. For example, an anti-CD28 antibody of the present invention may exhibit reduced binding to CD28 at acidic pH as compared to neutral pH. Alternatively, anti-MUC16 antibodies of the invention may exhibit enhanced binding to MUC16 at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to CD28 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Antibodies Comprising Fc Variants

According to certain embodiments of the present invention, anti-CD28/anti-MUC16 bispecific antigen binding molecules are provided comprising an Fc domain comprising one or more mutations which enhance or diminish antibody binding to the FcRn receptor, e.g., at acidic pH as compared to neutral pH. For example, the present invention includes antibodies and antigen binding molecules comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-CD28/anti-MUC16 bispecific antigen binding molecules comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies and Antigen-Binding Molecules

The present invention includes antibodies and antigen-binding fragments thereof that bind human CD28 and/or MUC16 with high affinity. The present invention also includes antibodies and antigen binding fragments thereof that bind human CD28 and/or MUC16 with medium or low affinity, depending on the therapeutic context and particular targeting properties that are desired. For example, in the context of a bispecific antigen-binding molecule, wherein one arm binds CD28 and another arm binds a target antigen (e.g., MUC16), it may be desirable for the target antigen-binding arm to bind the target antigen with high affinity while the anti-CD28 arm binds CD28 with only moderate or low affinity. In this manner, preferential targeting of the antigen-binding molecule to cells expressing the target antigen may be achieved while avoiding general/untargeted CD28 binding and the consequent adverse side effects associated therewith.

According to certain embodiments, the present invention includes antibodies and antigen-binding fragments of antibodies that bind human CD28 (e.g., at 37° C.) with a $K_D$ of less than about 165 nM as measured by surface plasmon resonance, e.g., using an assay format as defined in Example 4 herein. In certain embodiments, the antibodies or antigen-binding fragments of the present invention bind CD28 with a Ko of less than about 150 nM, less than about 130 nM, less than about 120 nM, less than about 100 nM, less than about 50 nM, less than about 80 nM, less than about 60 nM, less than about 40 nM, or less than about 30 nM, as measured by surface plasmon resonance, e.g., using an assay format as defined in Example 4 herein, or a substantially similar assay.

The present invention also includes antibodies and antigen-binding fragments thereof that bind CD28 with a dissociative half-life (t½) of greater than about 2.1 minutes as measured by surface plasmon resonance at 37° C., e.g., using an assay format as defined in Example 4 herein, or a substantially similar assay. In certain embodiments, the antibodies or antigen-binding fragments of the present invention bind CD28 with a t ½ of greater than about 5 minutes, greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, or greater than about 1200 minutes, as measured by surface plasmon resonance at 25° C. or 37° C., e.g., using an assay format as defined in Example 4 herein, or a substantially similar assay.

The present invention includes bispecific antigen-binding molecules (e.g., bispecific antibodies) which are capable of simultaneously binding to human CD28 and human MUC16. According to certain embodiments, the bispecific antigen-binding molecules of the invention specifically interact with cells that express CD28 and/or MUC16. The extent to which a bispecific antigen-binding molecule binds cells that express CD28 and/or MUC16 can be assessed by fluorescence activated cell sorting (FACS), as illustrated in Example 5 herein. For example, the present invention includes bispecific antigen-binding molecules which specifically bind human or cynomolgus cells which express CD28 but not MUC16 (e.g., T cells), and human ovarian carcinoma cell lines which express MUC16 but not CD28 (e.g., OVCAR-3, or PEO1). The present invention includes bispecific antigen-binding molecules which bind any of the aforementioned cells and cell lines with an $EC_{50}$ value of from about $9.2 \times 10^{-6}$ to about $2.8 \times 10^{-10}$ M, or less, as determined using a FACS assay as set forth in Example 4 or a substantially similar assay.

The present invention also provides anti-CD28/anti-MUC16 bispecific antigen-binding molecules that induce or increase T cell-mediated killing of tumor cells. For example, the present invention includes anti-CD28xMUC16 antibodies that induce or increase T cell-mediated killing of tumor cells with an $EC_{50}$ of less than about 392 pM, as measured in an in vitro T cell-mediated tumor cell killing assay, e.g., using the assay format as defined in Example 7 herein (e.g., assessing the extent of PEO1 tumor cell killing by human or Cynomolgus PBMCs in the presence of anti-CD28xMUC16 antibodies), or a substantially similar assay. In certain embodiments, the antibodies or antigen-binding fragments of the present invention induce T cell-mediated tumor cell killing (e.g., PBMC mediated killing of PEO1 cells) with an $EC_{50}$ value of less than about 200 pM, less than about 150 pM, less than about 100 pM, less than about 75 pM, less than about 50 pM, less than about 25 pM, less than about 10 pM, less than about 5.0 pM, less than about 4.0 pM, less than about 3.0 pM, less than about 2.5 pM, less than about 2.0 pM, less than about 1.5 pM, or less than about 1.45 pM, as measured by an in vitro T cell mediated tumor cell killing assay, e.g., using the assay format as defined in Example 7 herein, or a substantially similar assay.

The present invention also includes anti-CD28/anti-MUC16 bispecific antigen-binding molecules which bind to CD28-expressing human and/or Cynomolgus T-cells with an $EC_{50}$ value of between 1.0 pM and 10 μM. In certain embodiments, the anti-CD28/anti-MUC16 bispecific antigen-binding molecules bind to CD28-expressing human and/or Cynomolgus T-cells with an $EC_{50}$ value of between 9.2 μM and 120 nM. For example, the present invention includes anti-CD28/anti-MUC16 bispecific antigen-binding molecules which bind to CD28-expressing human T-cells with an $EC_{50}$ value of about 1 pM. about 10 pM, about 100 pM, about 500 pM, about 1 nM, about 2 nM, about 5 nM, about 10 nM, about 20 nM, about 30 nM, about 40 nM, about 50 nM about 60 nM, about 70 nM, about 80 nM, about 90 nM, about 100 nM, about 200 nM, about 300 nM, about 500 nM, about 800 nM, about 1000 nM, about 2 μM, about 4 μM, about 6 μM, about 8 μM, about 10 μM, or more.

The present invention also includes anti-CD28/anti-MUC16 bispecific antigen-binding molecules which exhibit one or more characteristics selected from the group consisting of: (a) activating T-cells, inducing IL-2 release, and CD25+ and PD-1 up-regulation in human PBMCs (see, e.g., Examples 6 and 7 herein); (b) increasing human or cyno-molgus T-cell mediated cytotoxicity on MUC16 expressing cell lines (see, e.g., Example 7 herein); (c) inducing naïve primate T cell-mediated cytotoxicity on MUC16 expressing cell lines (see, e.g., Example 7 herein); (e) depleting tumor cells in mice (e.g., Example 8 herein); (f) enhancing tumor clearance in mice (e.g., Example 8 herein); (g) not inducing systemic T cell activation in cynomolgus monkey.

The present invention includes anti-CD28/anti-MUC16 bispecific antigen-binding molecules which are capable of depleting tumor cells in a subject (see, e.g., Example 9). For example, according to certain embodiments, anti-CD28/anti-MUC16 bispecific antigen-binding molecules are provided, wherein double administrations of the bispecific antigen-binding molecule to a subject (e.g., at a dose of about 5.0 mg/kg, about 2.5 mg/kg, about 1.0 mg/kg about 0.5 mg/kg, about 0.2 mg/kg, about 0.1 mg/kg, about 0.05 mg/kg, about 0.02 mg/kg, about 0.01 mg/kg or less) causes a reduction in the number of tumor cells in the subject. According to certain embodiments, anti-CD28/anti-MUC16 bispecific antigen-binding molecules are provided, wherein double administrations of the bispecific antigen-binding molecule to a subject (e.g., at a dose of about 2500 mg, about 1000 mg, about 500 mg, about 200 mg, about 100 mg, about 50 mg/kg, about 25 mg/kg, or less) causes a reduction in the number of tumor cells in the subject.

Epitope Mapping and Related Technologies

The epitope on CD28 or MUC16 to which the antigen-binding molecules of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a CD28 protein or a MUC16 protein. Alternatively, the epitope may consist of a plurality of non-contiguous amino acids (or amino acid sequences) of CD28 or MUC16. The antibodies of the invention may interact with amino acids contained within a CD28 mono-mer, or may interact with amino acids on two different CD28 chains of a CD28 dimer. The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques that can be used to determine an epitope or binding domain of a particular antibody or antigen-binding domain include, e.g., routine crossblocking assay such as that described in *Antibodies*, Harlow and Lane (Cold Spring Harbor Press, Cold Spring Harb., NY), point mutagenesis (e.g., alanine scanning mutagenesis, arginine scanning mutagenesis, etc.), peptide blots analysis (Reineke, 2004, Methods Mol Biol 248:443-463), protease protection, and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystal structure analysis can also be used to identify the amino acids within a polypeptide with which an antibody interacts.

The present invention further includes anti-CD28 and anti-MUC16 antibodies that bind to the same epitope as any of the specific exemplary antibodies described herein (e.g. antibodies comprising any of the amino acid sequences as set forth in Tables 1 and 3 herein). Likewise, the present invention also includes anti-CD28 and/or anti-MUC16 antibodies that compete for binding to CD28 and/or MUC16 with any of the specific exemplary antibodies described herein (e.g. antibodies comprising any of the amino acid sequences as set forth in Table 1 herein).

The present invention also includes bispecific antigen-binding molecules comprising a first antigen-binding domain that specifically binds human CD28, and a second antigen binding fragment that specifically binds human MUC16, wherein the first antigen-binding domain binds to the same epitope on CD28 as any of the specific exemplary CD28-specific antigen-binding domains described herein, and/or wherein the second antigen-binding domain binds to the same epitope on MUC16 as any of the specific exemplary MUC16-specific antigen-binding domains described herein.

Likewise, the present invention also includes bispecific antigen-binding molecules comprising a first antigen-binding domain that specifically binds human CD28, and a second antigen binding fragment that specifically binds human MUC16, wherein the first antigen-binding domain competes for binding to CD28 with any of the specific exemplary CD28-specific antigen binding domains described herein, and/or wherein the second antigen-binding domain competes for binding to MUC16 with any of the specific exemplary MUC16-specific antigen-binding domains described herein.

One can easily determine whether a particular antigen-binding molecule (e.g., antibody) or antigen-binding domain thereof binds to the same epitope as, or competes for binding with, a reference antigen-binding molecule of the present invention by using routine methods known in the art. For example, to determine if a test antibody binds to the same epitope on CD28 (or MUC16) as a reference bispecific antigen-binding molecule of the present invention, the reference bispecific molecule is first allowed to bind to a CD28 protein (or MUC16 protein). Next, the ability of a test antibody to bind to the CD28 (or MUC16) molecule is assessed. If the test antibody is able to bind to CD28 (or MUC16) following saturation binding with the reference bispecific antigen-binding molecule, it can be concluded that the test antibody binds to a different epitope of CD28 (or MUC16) than the reference bispecific antigen-binding molecule. On the other hand, if the test antibody is not able to bind to the CD28 (or MUC16) molecule following saturation binding with the reference bispecific antigen-binding molecule, then the test antibody may bind to the same epitope of CD28 (or MUC16) as the epitope bound by the reference bispecific antigen-binding molecule of the invention. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a CD28 protein (or MUC16 protein) under saturating conditions followed by assessment of binding of the test antibody to the CD28 (or MUC16) molecule. In a second orientation, the test antibody is allowed to bind to a CD28 (or MUC16) molecule under saturating conditions followed by assessment of binding of the reference antigen-binding molecule to the CD28 (or MUC16) molecule. If, in both orientations, only the first (saturating) antigen-binding molecule is capable of binding to the CD28 (or MUC16) molecule, then it is concluded that the test antibody and the reference antigen-binding molecule compete for binding to CD28 (or MUC16). As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD28 and MUC16), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIM-MUNE™ technology. Using VELOCIMMUNE™ technology (or any other human antibody generating technology), high affinity chimeric antibodies to a particular antigen (e.g., CD28 or MUC16) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. (See, e.g., US 2011/0195454 for a detailed discussion of such engineered mice and the use thereof to produce bispecific antigen-binding molecules).

Bioequivalents

The present invention encompass antigen-binding molecules having amino acid sequences that vary from those of the described antibodies but that retain the ability to bind CD28 and/or MUC16. Such variant molecules comprise one or more additions, deletions, or substitutions of amino acids when compared to parent sequence, but exhibit biological activity that is essentially equivalent to that of the described antigen-binding molecules. Likewise, the antigen binding molecules-encoding DNA sequences of the present invention encompass sequences that comprise one or more additions, deletions, or substitutions of nucleotides when compared to the disclosed sequence, but that encode an antigen binding molecule that is essentially bioequivalent to the described antigen-binding molecules of the invention. Examples of such variant amino acid and DNA sequences are discussed above.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include the exemplary bispecific antigen-binding molecules set forth herein comprising amino acid changes which modify the glycosylation characteristics of the antibodies, e.g., mutations which eliminate or remove glycosylation.

Species Selectivity and Species Cross-Reactivity

The present invention, according to certain embodiments, provides antigen-binding molecules that bind to human CD28 but not to CD28 from other species. The present invention also provides antigen-binding molecules that bind to human MUC16 but not to MUC16 from other species. The present invention also includes antigen-binding molecules that bind to human CD28 and to CD28 from one or more non-human species; and/or antigen-binding molecules that bind to human MUC16 and to MUC16 from one or more non-human species.

According to certain exemplary embodiments of the invention, antigen-binding molecules are provided which bind to human CD28 and/or human MUC16 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee CD28 and or MUC16. For example, in a particular exemplary embodiment of the present invention, bispecific antigen-binding molecules are provided comprising a first antigen-binding domain that binds human CD28 and cynomolgus CD28, and a second antigen-binding domain that specifically binds human MUC16.

Immunoconjugates

The present invention encompasses antigen-binding molecules conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Therapeutic Formulation and Administration

The present invention provides pharmaceutical compositions comprising the antigen binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen-binding molecule administered to a patient may vary depending upon the age and the size of the patient, target disease, conditions, route of administration, and the like. The preferred dose is typically calculated according to body weight or body surface area. When a bispecific antigen-binding molecule of the present invention is used for therapeutic purposes in an adult patient, it may be advantageous to intravenously administer the bispecific antigen-binding molecule of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMA-LOG MIX 75/25™ pen, HUMALOG™ pen, HUMALIN 70/30™ pen (Eli Lilly and Co., Indianapolis, IN), NOVOPEN™ 1, ‖ and Ill (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antigen-Binding Molecules

The present invention includes methods comprising administering to a subject in need thereof a therapeutic composition comprising an anti-CD28 antibody or a bispecific antigen binding molecule that specifically binds CD28 and a target antigen (e.g., MUC16). The therapeutic composition can comprise any of the antibodies or bispecific antigen-binding molecules as disclosed herein and a pharmaceutically acceptable carrier or diluent. As used herein, the expression "a subject in need thereof" means a human or non-human animal that exhibits one or more symptoms or indicia of cancer (e.g., a subject expressing a tumor or suffering from any of the cancers mentioned herein below), or who otherwise would benefit from an inhibition or reduction in MUC16 activity or a depletion of MUC16+ cells.

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the anti-CD28/anti-MUC16 bispecific antigen-binding molecules of the present invention may be used for the treatment, prevention and/or amelioration of any disease or disorder associated with or mediated by MUC16 expression or activity or the proliferation of MUC16+ cells. The mechanism of action by which the therapeutic methods of the invention are achieved include killing of the cells expressing MUC16 in the presence of effector cells, for example, T cells. Cells expressing MUC16 which can be inhibited or killed using the bispecific antigen-binding molecules of the invention include, for example, tumorigenic ovarian cells.

The antigen-binding molecules of the present invention may be used to treat, e.g., primary and/or metastatic tumors arising in the colon, lung, breast, renal cancer, and subtypes of bladder cancer. According to certain exemplary embodiments, the bispecific antigen binding molecules of the present invention are used to treat a ovarian cancer.

The present invention also includes methods for treating residual cancer in a subject. As used herein, the term "residual cancer" means the existence or persistence of one or more cancerous cells in a subject following treatment with an anti-cancer therapy.

According to certain aspects, the present invention provides methods for treating a disease or disorder associated with MUC16 expression (e.g., MUC16 expressing cancer such as ovarian cancer) comprising administering one or more of the bispecific antigen-binding molecules described elsewhere herein to a subject after the subject has been shown to be non-responsive to other types of anti-cancer therapies. For example, the present invention includes methods for treating ovarian cancer comprising administering an anti-CD28/anti-MUC16 bispecific antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received the standard of care for patients suffering from cancer, e.g., ovarian cancer. In other aspects, a bispecific antigen-binding molecule of the invention (an anti-CD28/anti-MUC16 bispecific antigen binding molecule) comprising an IgG4 Fc domain is initially administered to a subject at one or more time points (e.g., to provide robust initial depletion of ovarian cancer cells), followed by administration of an equivalent bispecific antigen-binding molecule comprising a different IgG domain, such as an IgG1 Fc domain, at subsequent time points. It is envisioned that the anti-CD28/anti-MUC16 antibodies of the invention may be used in conjunction with other bispecific antigen binding molecules, such as with an anti-MUC16/anti-CD3 bispecific antibody. It is also envisioned that the bispecific antibodies of the invention will be used in conjunction with checkpoint inhibitors, for example, those that target PD-1 and CTLA-4, and other targets. It may be advantageous to combine two bispecific antibodies that target the same tumor antigen (e.g. MUC16), but with one of the bispecifics targeting the CD3 on T cells and the other bispecific targeting a co-stimulator molecule like CD28. This combination may be used alone to enhance tumor cell killing, or may be used in combination with a checkpoint inhibitor.

Exemplary MUC16 expressing cancers include, but are not limited to ovarian cancer, breast cancer, endometrial cancer, pancreatic cancer, non-small-cell lung cancer, intrahepatic cholangiocarcinoma-mass forming type, adenocarcinoma of the uterine cervix, and adenocarcinoma of the gastric tract.

Combination Therapies and Formulations

The present invention includes compositions and therapeutic formulations comprising any of the exemplary antibodies and bispecific antigen-binding molecules described herein in combination with one or more additional therapeutically active components, and methods of treatment comprising administering such combinations to subjects in need thereof.

Exemplary additional therapeutic agents that may be combined with or administered in combination with an antigen-binding molecule of the present invention include, e.g., chemotherapy, radiation therapy, checkpoint inhibitors that target PD-1 (e.g., an anti-PD-1 antibody such as pembrolizumab, nivolumab, or cemiplimab (see U.S. Pat. No. 9,987,500)), CTLA-4, LAG3, TIM3, and others, costimulatory agonist bivalent antibodies that target molecules such as GITR, OX40, 4-1BB, and others), CD3x bispecific antibodies (See for example WO2017/053856A1, WO2014/047231A1, WO2018/067331A1 and WO2018/058001A1), other antibodies that target MUC16 X CD3 (See for example WO2017/053856A1) and other costimulatory CD28 bispecific antibodies.

Other agents that may be beneficially administered in combination with antibodies of the invention include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions of the present invention (e.g., pharmaceutical compositions comprising an anti-CD28/anti-MUC16 bispecific antigen-binding molecule as disclosed herein) may also be administered as part of a therapeutic regimen comprising one or more therapeutic combinations selected from "ICE": ifosfamide (e.g., Ifex®), carboplatin (e.g., Paraplatin®), etoposide (e.g., Etopophos®, Toposar®, VePesid®, VP-16); "DHAP": dexamethasone (e.g., Decadron®), cytarabine (e.g., Cytosar-U®, cytosine arabinoside, ara-C), cisplatin (e.g., Platinol®-AQ); and "ESHAP": etoposide (e.g., Etopophos®, Toposar®, VePesid®, VP-16), methylprednisolone (e.g., Medrol®), high-dose cytarabine, cisplatin (e.g., Platinol®-AQ).

The present invention also includes therapeutic combinations comprising any of the antigen-binding molecules mentioned herein and an inhibitor of one or more of VEGF, Ang2, DLL4, EGFR, ErbB2, ErbB3, ErbB4, EGFRvIII, cMet, IGF1 R, B-raf, PDGFR-o, PDGFR-I3, FOLH1, PRLR, STEAP1, STEAP2, TMPRSS2, MSLN, CA9, uroplakin, or any of the aforementioned cytokines, wherein the inhibitor is an aptamer, an antisense molecule, a ribozyme, an siRNA, a peptibody, a nanobody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). The antigen-binding molecules of the invention may also be administered and/or co-formulated in combination with antivirals, antibiotics, analgesics, corticosteroids and/or NSAIDs. The antigen-binding molecules of the invention may also be administered as part of a treatment regimen that also includes radiation treatment and/or conventional chemotherapy, or treatment with a biologic, including checkpoint inhibitors or other bispecific antibodies.

The present invention includes compositions and therapeutic formulations comprising any of the antigen-binding molecules described herein in combination with one or more chemotherapeutic agents. Examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The additional therapeutically active component(s) may be administered just prior to, concurrent with, or shortly after the administration of an antigen-binding molecule of the present invention; (for purposes of the present disclosure, such administration regimens are considered the administration of an antigen-binding molecule "in combination with" an additional therapeutically active component).

The present invention includes pharmaceutical compositions in which an antigen binding molecule of the present invention is co-formulated with one or more of the additional therapeutically active component(s) as described elsewhere herein.

Administration Regimens

According to certain embodiments of the present invention, multiple doses of an antigen-binding molecule (e.g., an anti-CD28 antibody or a bispecific antigen-binding molecule that specifically binds MUC16 and CD28) may be administered to a subject over a defined time course. The methods according to this aspect of the invention comprise sequentially administering to a subject multiple doses of an antigen-binding molecule of the invention. As used herein, "sequentially administering" means that each dose of an antigen-binding molecule is administered to the subject at a different point in time, e.g., on different days separated by a predetermined interval (e.g., hours, days, weeks or months). The present invention includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but generally may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of an antigen-binding molecule (e.g., an anti-CD28 antibody or a bispecific antigen-binding molecule that specifically binds MUC16 and CD28). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In one embodiment, the antigen-binding molecule (e.g., a bispecific antigen-binding molecule that specifically binds MUC16 and CD28) is administered to a subject as a weight-based dose. A "weight-based dose" (e.g., a dose in mg/kg) is a dose of the antibody or the antigen-binding fragment thereof or the bispecific antigen-binding molecule that will change depending on the subject's weight.

In another embodiment, an antibody or the antigen-binding fragment thereof or a bispecific antigen-binding molecule is administered to a subject as a fixed dose. A "fixed dose" (e.g., a dose in mg) means that one dose of the antibody or the antigen-binding fragment thereof or the bispecific antigen-binding molecule is used for all subjects regardless of any specific subject-related factors, such as weight. In one particular embodiment, a fixed dose of an antibody or the antigen-binding fragment thereof or a bispecific antigen-binding molecule of the invention is based on a predetermined weight or age.

In general, a suitable dose of the antigen binding molecule the invention can be in the range of about 0.001 to about 200.0 milligram per kilogram body weight of the recipient, generally in the range of about 1 to 50 mg per kilogram body weight. For example, the antibody or the antigen-binding fragment thereof or the bispecific antigen-binding molecule can be administered at about 0.1 mg/kg, about 0.2 mg/kg, about 0.5 mg/kg, about 1 mg/kg, about 1.5 mg/kg, about 2 mg/kg, about 3 mg/kg, about 5 mg/kg, about 10 mg/kg, about 15 mg/kg, about 20 mg/kg, about 25 mg/kg, about 30 mg/kg, about 40 mg/kg, about 50 mg/kg per single dose. Values and ranges intermediate to the recited values are also intended to be part of this invention.

In some embodiments, the antigen binding molecule of the invention is administered as a fixed dose of between about 25 mg to about 2500 mg. In some embodiments, the antigen binding molecule of the invention is administered as a fixed dose of about 25 mg, about 30 mg, about 50 mg, about 75 mg, about 100 mg, about 125 mg, about 150 mg, about 175 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1500 mg, about 2000 mg, or about 2500 mg. Values and ranges intermediate to the recited values are also intended to be part of this invention.

Diagnostic Uses of the Antibodies

The bispecific antibodies of the present invention may also be used to detect and/or measure CD28 or MUC16, or CD28-expressing or MUC16-expressing cells in a sample, e.g., for diagnostic purposes. For example, an anti-CD28 x MUC16 antibody, or fragment thereof, may be used to diagnose a condition or disease characterized by aberrant expression (e.g., over-expression, under-expression, lack of expression, etc.) of CD28 or MUC16. Exemplary diagnostic assays for CD28 or MUC16 may comprise, e.g., contacting a sample, obtained from a patient, with an antibody of the invention, wherein the antibody is labeled with a detectable label or reporter molecule. Alternatively, an unlabeled antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, betagalactosidase, horseradish peroxidase, or luciferase. Specific exemplary assays that can be used to detect or measure CD28 or MUC16 in a sample include enzyme-linked immunosorbent assay (ELISA), radioimmunoassay (RIA), and fluorescence-activated cell sorting (FACS). Samples that can be used in CD28 or MUC16 diagnostic assays according to the present invention include any tissue or fluid sample obtainable from a patient which contains detectable quantities of CD28 or MUC16 protein, or fragments thereof, under normal or pathological conditions. Generally, levels of CD28 or MUC16 in a particular sample obtained from a healthy patient (e.g., a patient not afflicted with a disease or condition associated with abnormal CD28 or MUC16 levels or activity) will be measured to initially establish a baseline, or standard, level of CD28 or MUC16. This baseline level of CD28 or MUC16 can then be compared against the levels of CD28 or MUC16 measured in samples obtained from individuals suspected of having a CD28 or MUC16 related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Background

T cell activation is initiated upon binding of the T Cell Receptor (TCR)/CD3 complex to peptide-MHC complexes ("signal 1"); activation is then enhanced by engagement of a second "co-stimulatory" receptor, such as the CD28 receptor on T cells binding to its cognate ligand(s) on the target cell ("signal 2"). Recently described CD3-based "bispecific antibodies" act by replacing conventional signal 1, linking T cells to tumor cells by binding a tumor-specific antigen (TSA) with one arm of the bispecific, and bridging to TCR/CD3 with the other. Although some of these so-called TSAxCD3 bispecifics have demonstrated promising anti-tumor efficacy in cancer patients, their activity remains to be optimized. As described elsewhere herein, introduced in the present invention is a novel class of bispecific antibodies that mimic signal 2, by bridging a second TSA to the co-stimulatory CD28 receptor on T cells. These bispecific antibodies were termed TSAxCD28 bispecifics. As described herein, one exemplary antibody of the present invention is specific for ovarian cancer antigens (e.g., MUC16). Unlike CD28 superagonists, which broadly activate T cells and resulted in profound toxicity in early clinical trials, these TSAxCD28 bispecifics show limited activity and no toxicity when used alone in genetically-humanized immuno-competent mouse models, or in primates. However, when combined with TSAxCD3 bispecifics, the exemplary antibody of the invention enhanced the artificial synapse between a T cell and its target cell, potentiated T cell activation, and markedly improved anti-tumor activity of CD3-bispecifics in a variety of xenogeneic and syngeneic tumor models. Combining this novel class of CD28-costimulatory bispecific antibodies with the emerging class of TSAxCD3 bispecifics may provide well-tolerated, "off-the-shelf" antibody therapies with potentially enhanced anti-tumor efficacy.

The ability of T cells to recognize and kill their cellular targets—such as virally-infected cells or tumor cells—depends on a coordinated set of interactions. Foremost among these is the recognition and binding of the target cell by the TCR complex (which includes the associated CD3 γ, δ, ε, ζ chains); this interaction has been referred to as "signal 1" for T cell activation. The TCR can recognize viral or tumor peptide presented in the groove of an MHC proteins expressed on the surface of the target cells. This binding is typically of low-affinity; therefore successful triggering of signal 1 requires clustering of many TCR complexes along the interface between a T cell and its target cell, and this interface has been referred to as the immune synapse (J. B. Huppa, M. M. Davis, T-cell-antigen recognition and the immunological synapse. *Nat Rev Immunol* 3, 973-983 (2003)). T cell activation and proliferation are then further promoted by additional interactions with costimulatory receptors such as CD28 ("signal 2") (J. H. Esensten, Y. A. Helou, G. Chopra, A. Weiss, J. A. Bluestone, CD28 Costimulation: From Mechanism to Therapy. *Immunity* 44, 973-988 (2016)). When a T cell recognizes a target cell via the TCR complex, and engages signal 2 via CD28 binding to its cognate ligand(s) (CD80/B7.1 and/or CD86/B7.2) on a professional antigen presenting cell or the target cell, T cell activation is enhanced. As with signal 1, CD28-mediated signal 2 is thought to occur via coclustering at the immune synapse.

Conventional monoclonal antibodies targeted against tumor-specific antigens (TSAs) have been used as anti-tumor therapeutics over the last two decades (G. Salles et al., Rituximab in B-Cell Hematologic Malignancies: A Review of 20 Years of Clinical Experience. *Adv Ther* 34, 2232-2273 (2017); M. V. Mateos et al., Daratumumab plus Bortezomib, Melphalan, and Prednisone for Untreated Myeloma. *N Engl J Med* 378, 518-528 (2018): W. Eiermann, G. International Herceptin Study, Trastuzumab combined with chemotherapy for the treatment of HER2-positive metastatic breast cancer: pivotal trial data. *Ann Oncol* 12 Suppl 1, S57-62 (2001); J. M. Connors et al., Brentuximab Vedotin with Chemotherapy for Stage Ill or IV Hodgkin's Lymphoma. *N Engl J Med* 378, 331-344 (2018); V. Dieras et al., Trastuzumab emtansine versus capecitabine plus lapatinib in patients with previously treated HER2-positive advanced breast cancer (EMILIA): a descriptive analysis of final overall survival results from a randomised, open-label, phase 3 trial. *Lancet Oncol* 18, 732-742 (2017)). However, this class of antibodies had limited ability to induce T cell mediated cytotoxicity, and instead acted by promoting antibody-dependent cellular cytotoxicity (ADCC) and/or complement-dependent cytotoxicity (CDC), or by delivering a toxin to the tumor cells. Recently, a new class of bispecific antibodies (TSAxCD3) has emerged that can efficiently trigger T cell-mediated killing of tumor cells, by linking a T cell to a tumor cell and activating the CD3/TCR complex (usually via the e chain of CD3) via a surrogate mechanism, thus mimicking signal 1. An early version of such a bispecific (one arm binding to CD19 on leukemia cells, while the other binds to CD3) recently received regulatory approval for B cell acute lymphoblastic leukemia (R. Bargou et al., Tumor regression in cancer patients by very low doses of a T cell engaging antibody. *Science* 321, 974-977 (2008); H. Kantarjian et al., Blinatumomab versus Chemotherapy for Advanced Acute Lymphoblastic Leuke-mia. *N Engl J Med* 376, 836-847 (2017)). Recently, more advanced versions of bispecifics have been shown to have good activity against non-Hodgkin's Lymphomas, targeting CD20 on these lymphomas (E. J. Smith et al., A novel, native-format bispecific antibody triggering T-cell killing of B cells is robustly active in mouse tumor models and cynomolgus monkeys. *Sci Rep* 5, 17943 (2015); L. L. Sun et al., Anti-CD20/CD3 T cell-dependent bispecific antibody for the treatment of B cell malignancies. *Sci Transl Med* 7, 287ra270 (2015); M. Bacac et al., CD20-TCB with Obinu-tuzumab Pretreatment as Next-Generation Treatment of Hematologic Malignancies. *Clin Cancer Res* 24, 4785-4797 (2018); R. Bannerji et al., Emerging Clinical Activity of REGN1979, an Anti-CD20 x Anti-CD3 Bispecific Antibody, in Patients with Relapsed/Refractory Follicular Lymphoma (FL), Diffuse Large B-Cell Lymphoma (DLBCL), and Other B-Cell Non-Hodgkin Lymphoma (B-NHL) Subtypes. *American Society of Hematology*, (2018); L. Budde et al., Mosunetuzumab, a Full-Length Bispecific CD20/CD3 Anti-body, Displays Clinical Activity in Relapsed/Refractory B-Cell Non-Hodgkin Lymphoma (NHL): Interim Safety and Efficacy Results from a Phase 1 Study. *American Society of Hematology*, (2018)). However, although TSAxCD3 bispe-cifics are emerging as an important new class of immuno-therapy in hematologic malignancies, cross-study compari-sons (E. A. Zhukovsky, R. J. Morse, M. V. Maus, Bispecific antibodies and CARs: generalized immunotherapeutics har-nessing T cell redirection. *Curr Opin Immunol* 40, 24-35 (2016)) suggest that in some cases they may not be achiev-ing the level of efficacy seen with the personalized chimeric antigen receptor T cell (CAR-T) therapies.

One of the reasons for the strong efficacy of CAR-T therapies is that the chimeric antigen receptor (CAR) is engineered to provide both signal 1 (via a portion of the CD3z cytodomain) and signal 2 (e.g., via a portion of the CD28 cytodomain) upon binding to its target on a tumor cell. Two CAR-T cell therapies have recently received FDA approval for B-cell malignancies, both of which act by binding and targeting the antigen CD19 (S. S. Neelapu et al., Axicabtagene Ciloleucel CAR T-Cell Therapy in Refractory Large B Cell Lymphoma. *N Eng J Med* 377, 2531-2544 (2017); S. J. Schuster et al., Chimeric Antigen Receptor T Cells in Refractory B-Cell Lymphomas. *N Eng J Med* 377, 2545-2554 (2017)). CAR-T cell approaches can be associ-ated with severe adverse effects such as cytokine release syndrome (CRS) and neurotoxicity (S. S. Neelapu et al., Chimeric antigen receptor T-cell therapy—assessment and management of toxicities. *Nat Rev Clin Oncol* 15, 47-62 (2018); J. Gust et al., Endothelial Activation and Blood-Brain Barrier Disruption in Neurotoxicity after Adoptive Immunotherapy with CD19 CAR-T Cells. *Cancer Discov* 7, 1404-1419 (2017); A. Shimabukuro-Vornhagen et al., Cyto-kine release syndrome. *J Immunother Cancer* 6, 56 (2018)); and due to the highly-personalized manufacturing processes and requirement for preconditioning chemotherapeutic regi-mens (S. S. Neelapu et al., Axicabtagene Ciloleucel CAR T-Cell Therapy in Refractory Large B Cell Lymphoma. *N Engl J Med* 377, 2531-2544 (2017); S. J. Schuster et al., Chimeric Antigen Receptor T Cells in Refractory B-Cell Lymphomas. *N Engl J Med* 377, 2545-2554 (2017); P. Salmikangas, N. Kinsella, P. Chamberlain, Chimeric Anti-gen Receptor T-Cells (CART-Cells) for Cancer Immuno-therapy—Moving Target for Industry? *Pharm Res* 35, 152 (2018)), many patients are not deemed suitable candidates.

The advantages of TSAxCD3 bispecifics as relatively well-tolerated and "off-the-shelf" therapeutic solutions for broader patient populations would be enhanced if their anti-tumor activity could be further optimized, especially if this could be done without sacrificing tolerability, or perhaps even increase, specificity for tumor cells as opposed to normal cells. Towards this end, it was hypothesized that pairing TSAxCD3 bispecifics with a novel class of bispe-cifics that independently activates signal 2 could provide potential increased efficacy as well as an opportunity for enhanced specificity. Therefore, a second class of bispecifics were designed. These bispecifics could either engage a second epitope on the same tumor-specific antigen or a second separate tumor antigen, with the co-stimulatory receptor CD28 (TSAxCD28 Bispecifics) expressed on T cells. It was reasoned that combining TSA1xCD3 with a TSA2xCD28 should allow directed and enhanced surrogate activation of T cells by triggering both signal 1 and signal 2, with specificity targeted only against tumor cells expressing both epitopes or both antigens, allowing for greater anti-tumor activity together with an opportunity for increased specificity.

Described herein are the generation and testing of TSAxCD28 co-stimulatory bispecific antibodies targeted to ovarian cancer (MUC16xCD28, which binds MUC16, a large integral membrane glycoprotein expressed at high levels in ceratin cancers (H. Suh, K. Pillai, D. L. Morris, Mucins in pancreatic cancer: biological role, implications in carcinogenesis and applications in diagnosis and therapy. *Am J Cancer Res* 7, 1372-1383 (2017)), and which is cleaved to release the ovarian tumor biomarker CA-125 (I. Mylonas et al., Immunohistochemical expression of the tumour marker CA-125 in normal, hyperplastic and malig-nant endometrial tissue. *Anticancer Res* 23, 1075-1080 (2003)). Toxicology studies in genetically-humanized immunocompetent mice as well as in cynomolgus monkeys demonstrate that these bispecifics exhibit limited activity and no toxicity as single agents. However, these novel co-stimulatory bispecifics can be effectively combined with the emerging class of TSAxCD3 bispecifics to potentiate anti-tumor responses in both xenogenic and syngeneic tumor models. Collectively, these data suggest that combining this novel class of CD28-based bispecifics (TSAxCD28) with the CD3-based bispecifics (TSAxCD3) may provide well-tolerated, "off-the-shelf" biologics solutions with markedly enhanced and synergistic anti-tumor activity.

Example 1. Construction of Anti-MUC16xCD28
Antibodies

Generation of Anti-CD28 Antibodies

Anti-CD28 antibodies were obtained by immunizing a VELOCIMMUNE® mouse (i.e., an engineered mouse com-prising DNA encoding human Immunoglobulin heavy and kappa light chain variable regions) with human CD28 pro-tein fused to the Fc portion of mouse IgG2a, or with cells expressing CD28, or with DNA encoding CD28. The antibody immune response was monitored by a CD28-specific immunoassay. When a desired immune response was achieved splenocytes were harvested and fused with mouse myeloma cells to preserve their viability and form hybridoma cell lines. The hybridoma cell lines were screened and selected to identify cell lines that produce CD28-specific antibodies. Using this technique several anti-CD28 chimeric antibodies (i.e., antibodies possessing human variable domains and mouse constant domains) were obtained. In addition, several fully human anti-CD28 antibodies were isolated directly from antigen-positive B cells without fusion to myeloma cells, as described in US 2007/0280945A1.

Certain biological properties of the exemplary anti-CD28 antibodies generated in accordance with the methods of this Example are described in detail in the Examples set forth below.

Generation of Anti-MUC16 Antibodies

Anti-MUC16 antibodies were obtained by immunizing a genetically modified mouse with a human MUC16 antigen or by immunizing an engineered mouse comprising DNA encoding human immunoglobulin heavy and kappa light chain variable regions with a human MUC16 antigen.

Genetically modified mice were immunized with hMUC16.nub (a truncated format encompassing the last five SEA domains of Mucin-16 (SEQ ID: 49), or immunized with an hMUC16-expressing cell line, such as OVCAR-3 cells. Following immunization, splenocytes were harvested from each mouse and either (1) fused with mouse myeloma cells to preserve their viability and form hybridoma cells and screened for MUC16 specificity, or (2) B-cell sorted (as described in US 2007/0280945A1) using a human MUC16 fragment as the sorting reagent that binds and identifies reactive antibodies (antigen-positive B cells).

Chimeric antibodies to MUC16 were initially isolated having a human variable region and a mouse constant region. The antibodies were characterized and selected for desirable characteristics, including affinity, selectivity, etc. If necessary, mouse constant regions were replaced with a Certain biological properties of the exemplary anti-MUC16 antibodies generated in accordance with the methods of this Example are described in detail in the Examples set forth below.

Generation of Bispecific Antibodies that Bind CD28 and MUC16

Bispecific antibodies comprising an anti-MUC16-specific binding domain and an anti-CD28-specific binding domain were constructed using standard methodologies, wherein the anti-MUC16 antigen binding domain and the anti-CD28 antigen binding domain each comprise different, distinct HCVRs paired with a common LCVR. In some instances the bispecific antibodies were constructed utilizing a heavy chain from an anti-CD28 antibody, a heavy chain from an anti-MUC16 antibody and a common light chain (See Table 5).

The bispecific antibodies created in accordance with the present Example comprise two separate antigen-binding domains (i.e., binding arms). The first antigen-binding domain comprises a heavy chain variable region derived from an anti-CD28 antibody ("CD28-VH"), and the second antigen-binding domain comprises a heavy chain variable region derived from an anti-MUC16 antibody ("MUC16-VH"). Both the anti-MUC16 and the anti-CD28 share a common light chain. The CD28-VH/MUC16-VH pairing creates antigen-binding domains that specifically recognize CD28 on T cells and MUC16 on tumor cells.

Example 2. Heavy and Light Chain Variable
Region Amino Acid and Nucleic Acid Sequences Table 1 sets forth the amino acid sequence identifiers of the heavy and light chain variable regions and CDRs of selected anti-MUC16 antibodies of the invention. The corresponding nucleic acid sequence identifiers are set forth in Table 2.

TABLE 1

| Amino Acid Sequence Identifiers of MUC 16 Antibodies | | | | | | | |
|---|---|---|---|---|---|---|---|
| Antibody | SEQ ID NOs: | | | | | | |
| Designation | HCVR | HCDR1 | HCDR2 | HCDR3 | LCVR | LCDR1 | LCDR2 | LCDR3 |
| mAb8799P2 | 2 | 4 | 6 | 8 | 10 | 12 | 14 | 16 |
| mAb8794P2 | 26 | 28 | 30 | 32 | 34 | 36 | 38 | 40 |

TABLE 2

| Nucleic Acid Sequence Identifiers of MUC16 Antibodies | | | | | | | |
|---|---|---|---|---|---|---|---|
| Antibody | SEQ ID NOs: | | | | | | |
| Designation | HCVR | HCDR1 | HCDR2 | HCDR3 | LCVR | LCDR1 | LCDR2 | LCDR3 |
| mAb8799P2 | 1 | 3 | 5 | 7 | 9 | 11 | 13 | 15 |
| mAb8794P2 | 25 | 27 | 29 | 31 | 33 | 35 | 37 | 39 | desired human constant region, for example wild-type or modified IgG1 or IgG4 constant region, to generate a fully human anti-MUC16 antibody. While the constant region selected may vary according to specific use, high affinity antigen-binding and target specificity characteristics reside in the variable region.

Table 3 sets forth the amino acid sequence identifiers of the heavy and light chain variable regions (HCVR and LCVR), CDRs of selected anti-CD28 antibodies of the invention. The corresponding nucleic acid sequence identifiers are set forth in Table 4.

TABLE 3

| | Amino Acid Sequence Identifiers of CD28 Antibodies | | | | | | |
|---|---|---|---|---|---|---|---|
| Antibody | SEQ ID NOs: | | | | | | |
| Designation | HCVR | HCDR1 | HCDR2 | HCDR3 | LCVR | LCDR1 | LCDR2 | LCDR3 |

| Designation | HCVR | HCDR1 | HCDR2 | HCDR3 | LCVR | LCDR1 | LCDR2 | LCDR3 |
|---|---|---|---|---|---|---|---|---|
| mAb14226P2 | 18 | 20 | 22 | 24 | 10 | 12 | 14 | 16 |
| mAb14216P2 | 42 | 44 | 46 | 48 | 34 | 36 | 38 | 40 |

TABLE 4

| | Nucleic Acid Sequence Identifiers of CD28 Antibody | | | | | | |
|---|---|---|---|---|---|---|---|
| Antibody | SEQ ID NOs: | | | | | | |
| Designation | HCVR | HCDR1 | HCDR2 | HCDR3 | LCVR | LCDR1 | LCDR2 | LCDR3 |

| Designation | HCVR | HCDR1 | HCDR2 | HCDR3 | LCVR | LCDR1 | LCDR2 | LCDR3 |
|---|---|---|---|---|---|---|---|---|
| mAb14226P2 | 17 | 19 | 21 | 23 | 9 | 11 | 13 | 15 |
| mAb14216P2 | 41 | 43 | 45 | 47 | 33 | 35 | 37 | 39 |

A summary of the component parts of the various anti-MUC16xCD3 bispecific antibodies constructed is set forth in Table 5. Tables 6 and 7 list the HCVR, LCVR, CDRs and heavy chain and light chain sequence identifiers of the bispecific antibodies.

TABLE 5

Summary of Component Parts of
Anti-MUC16 × Anti-CD28 Bispecific Antibodies

| Bispecific Antibody Identifier | Anti-MUC16 Antigen-Binding Domain Heavy Chain Variable Region | Anti-CD28 Antigen-Binding Domain Heavy Chain Variable Region | Common Light Chain Variable Region |
|---|---|---|---|
| bs24963D | mAb8799P2 | mAb14226P2 | ULC3-20 |
| bs32897D | mAb8794P2 | mAb14216P2 | ULC1-39 |

Table 6 shows the amino acid sequence identifiers for the bispecific anti-MUC16 x antd-CD28 antibodies exemplified herein. The corresponding nucleic acid sequence identifiers are set forth in Table 7.

TABLE 6

Amino Acid Sequences of Anti-MUC16 × Anti-CD28 Bispecific Antibodies

| Bispecific Antibody | Anti-CD28 First Antigen-Binding Domain (D1) | | | | Anti-MUC16 Second Antigen-Binding Domain (D2) | | | | Common Light Chain Variable Region | | | |
|---|---|---|---|---|---|---|---|---|---|---|---|---|
| Identifier | HCVR | HCDR1 | HCDR2 | HCDR3 | HCVR | HCDR1 | HCDR2 | HCDR3 | LCVR | LCDR1 | LCDR2 | LCDR3 |
| bs24963D | 18 | 20 | 22 | 24 | 2 | 4 | 6 | 8 | 10 | 12 | 14 | 16 |
| bs32897D | 42 | 44 | 46 | 48 | 26 | 28 | 30 | 32 | 34 | 36 | 38 | 40 |

TABLE 7

Nucleic Acid Sequences of Anti-MUC16 × Anti-CD28 Bispecific Antibodies

| Bispecific Antibody | Anti-CD28 First Antigen-Binding Domain (D1) | | | | Anti-MUC16 Second Antigen-Binding Domain (D2) | | | | Common Light Chain Variable Region | | | |
|---|---|---|---|---|---|---|---|---|---|---|---|---|
| Identifier | HCVR | HCDR1 | HCDR2 | HCDR3 | HCVR | HCDR1 | HCDR2 | HCDR3 | LCVR | LCDR1 | LCDR2 | LCDR3 |
| bs24963D | 17 | 19 | 21 | 23 | 1 | 3 | 5 | 7 | 9 | 11 | 13 | 15 |
| bs32897D | 41 | 43 | 45 | 47 | 25 | 27 | 29 | 31 | 33 | 35 | 37 | 39 |

Example 3. CD28 is a Potent Costimulatory Receptor

Figure 1:
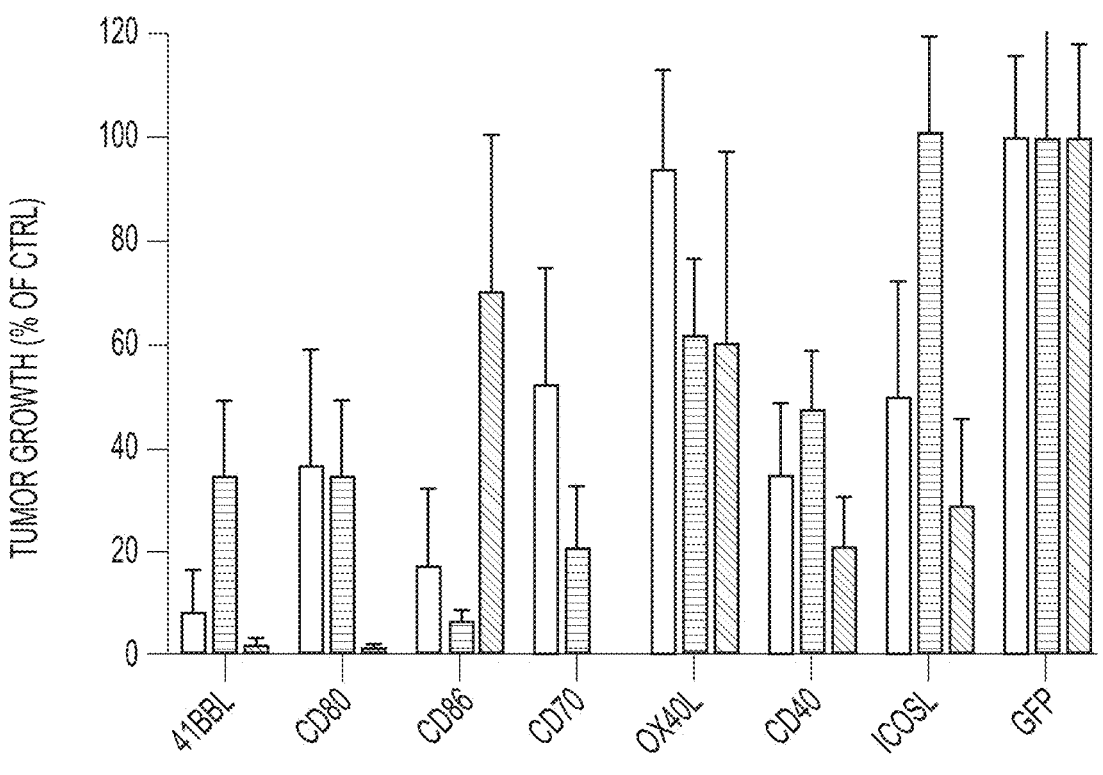
FIG. 1 is a graph showing tumor growth inhibition in engineered cell lines with introduced co-stimulatory ligand expression. Three tumor cell lines, B16F10.9, EL4, and MC38 were engineered to express a co-stimulatory ligand, or GFP, or empty vector as control. Engineered tumor cells were injected into C57BL/6 mice Data represent average±SEM. Data is representative of at least one experiment with five (5) mice per group.
Figure 1:
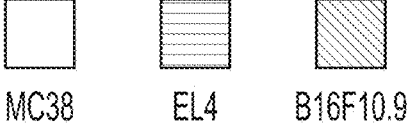

To determine which costimulatory receptors are effective in providing the costimulation signal that is important to T cell activation, a blinded screen of costimulatory pathways conducted by forced expression of costimulatory ligands on a panel of syngeneic tumors (Table 8 and FIG. 1) again established CD28 as one of the most potent costimulatory receptors together with 4-11BB. Table 8 summarizes the number of tumor free mice in the blinded screen. The assays were conducted on three different tumor cell lines which were engineered to express seven different co-stimulatory ligands. The number in each cell represents the number of tumor free mice out of a total of 5 mice.

TABLE 8

Tumor Growth Inhibition in Engineered Cell Lines
with Introduced Co-Stimulator Ligand

| Co-Stim. Ligand | Co-stim. Receptor | Lymphoma (EL4) | Carcinoma (MC38 | Melanoma (B16F10.9) |
|---|---|---|---|---|
| 4-1BBL | 4-BB | 3 | 4 | 1 |
| CD80 (B7.1) | CD28 | 2 | 2 | 2 |
| CD86 (B7.2) | CD28 | 1 | 0 | 2 |
| CD70 | CD27 | 5 | 0 | |
| OX40L | OX40 | 0 | 0 | 2 |
| CD40 | CD40L | 0 | 1 | 0 |
| ICOSL | ICOS | 0 | 0 | 0 |
| Empty Vector | | 0 | 0 | 0 |
| Non-transfected Parental cells | | 0 | 0 | |

Example 4. Surface Plasmon Resonance Derived Binding Affinities and Kinetic Constants of Anti-MUC16xCD28 Bispecific Antibodies In order to determine the binding kinetics of exemplary anti-MUC16xCD28 bispecific monoclonal antibodies of the invention, surface plasmon resonance derived binding affinities and kinetic constants of anti-MUC16xCD28 bispecific antibodies to MUC16 and/or CD28 were determined.

Equilibrium dissociation constants (Ko values) for hMUC16.mmh (SEQ ID NO: 51), hCD28.mmh (SEQ ID NO: 53) and mCD28.mmh (murine CD28.mmh; SEQ ID NO: 54) binding to purified exemplary anti-MUC16xCD28 bispecific monoclonal antibody of the invention were determined using a real-time surface plasmon resonance biosensor using a Biacore T-200 instrument. The CM5 Biacore sensor surface was derivatized by amine coupling with a monoclonal mouse anti-human Fc antibody to capture purified exemplary anti-MUC16xCD28 bispecific antibodies of the invention. Two exemplary bispecific antibodies were tested, bs24963D and REGN4615. REGN4615 is an antibody/scFv which recognizes human MUC16 and murine CD28 and is sometimes referred to as an anti-MUC16xmsCD28 antibody. The MUC16 arm in REGN4615 utilizes the VH and VK-ULC 1-39 sequences as shown above in Table 1 for mAb8794P2. The mCD28 (PV-1) is described in US2004/0116675, with a light chain of SEQ ID NO: 11 (See also FIG. 15A in US2004/0116675) and a heavy chain of SEQ ID NO: 13 (See FIG. 15), which was re-formatted as an scFv for the experiments described herein.

This SPR binding study was performed in a buffer composed of 0.01M HEPES pH 7.4, 0.15M NaCl 0.05% v/v Surfactant P20 at a pH of 7.4(HBS-ET running buffer). Different concentrations of hMUC16 with C-term myc-myc-6xHis tag (hMUC16.mmh), hCD28 with C-term myc-myc-6xHis tag (hCD28.mmh), and mCD28 C-term myc-myc-6xHis tag (mCD28.mmh) were prepared in HBS-ET running buffer, ranging from 3.33 nM to 90 nM (for hMuc16) or 22.2 nM to 600 nM (for hCD28 or mCD28) as serial 3-fold dilutions, for affinity determination over anti-MUC16xCD28 bispecific and anti-MUC16xmCD28 bispecific antibodies.

The MASS-2 high capacity amine sensor surface was first derivatized by amine coupling with a monoclonal mouse anti-human Fc antibody to capture approximately 500-900 RUs anti-MUC16xCD28 or anti-MUC16xmCD28 bispecific monoclonal antibodies. 1 RU (response unit) represents 1 pg of protein per mm$^2$, as defined by the manufacturer. Different concentrations of hMUC16 with C-term myc-myc-6xHis tag (hMUC16.mmh), hCD28 with C-term myc-myc-6xHis tag (hCD28.mmh), and mCD28 C-term myc-myc-6xHis tag (mCD28.mmh) were prepared in HBS-ET running buffer, ranging from 3.33 nM to 90 nM (for hMuc16) or 22.2 nM to 600 nM (for hCD28 or mCD28) as serial 3-fold dilutions and injected over anti-human Fc captured anti-MUC16xCD28 or anti-MUC16xmCD28 bispecific monoclonal antibodies surfaces for 5 minute at a flow rate of 50 µL/minute. The dissociation of bound hMUC16, hCD28, and mCD28 reagents was monitored for 10 minutes in HBS-ET running buffer. Association (ka) and dissociation (k$_d$) rate constants were determined by fitting the real-time binding sensorgrams to a 1:1 binding model with mass transport limitation using Scrubber evaluation software version 2.0c. Binding dissociation equilibrium constants (K$_D$) and dissociative half-lives (t½) were calculated from the kinetic rate constants as:

$$K_D(M) = \frac{kd}{ka}, \text{ and } t^{1/2}(\text{min}) = \frac{\ln(2)}{60 * kd}$$

Binding kinetic parameters for the exemplary bispecific antibodies binding to purified hMUC16, hCD28, mCD28 recombinant proteins at 37° C. are shown below in Tables 9-12.

TABLE 9

| | Biacore Binding Affinities of Anti-MUC16 × CD28 Antibodies to hMUC16 | | | | | | |
|---|---|---|---|---|---|---|---|
| AbPID | mAB Capture (RU) | 90 nM hMUC16.mmh Bind (RU) | Ka (1/Ms) | Kd (1/s) | K$_D$ (M) | T½ (min) |
| bs24963D (Experiment 1) | 987.1 ± 9.9 | 365.0 | 4.41E+05 | 4.12E−04 | 9.33E−10 | 28.0 |
| bs24963D (Experiment 2) | 211.7 ± 1.2 | 120.0 | 2.38E+05 | 2.18E−04 | 9.12E−10 | 53.1 |

TABLE 10

Biacore Binding Affinities of Anti-MUC16 × CD28 Antibodies to hCD28

| AbPID | mAB Capture (RU) | 600 nM hCD28.mmh Bind (RU) | Ka (1/Ms) | Kd (1/s) | $K_D$ (M) | T½ (min) |
|---|---|---|---|---|---|---|
| bs24963D | 985.4 ± 2.7 | 88.9 | 3.27E+04 | 5.38E–03 | 1.65E–07 | 2.1 |

TABLE 11

Biacore Binding Affinities of Anti-MUC16 × msCD28 Antibodies to hMUC16

| AbPID | mAB Capture (RU) | 90 nM hMUC16.mmh Bind (RU) | Ka (1/Ms) | Kd (1/s) | $K_D$ (M) | T½ (min) |
|---|---|---|---|---|---|---|
| REGN4615 | 1041.0 ± 10.0 | 513.3 | 6.29E+05 | 4.72E–04 | 7.49E–10 | 24.5 |

TABLE 12

Biacore Binding Affinities of Anti-MUC16xmsCD28 Antibodies to mCD28

| AbPID | mAB Capture (RU) | 90 nM hMUC16.mmh Bind (RU) | Ka (1/Ms) | Kd (1/s) | $K_D$ (M) | T½ (min) |
|---|---|---|---|---|---|---|
| REGN4615 | 1021.8 ± 4.0 | 25.8 | 2.07E+04 | 7.77E–05 | 3.76E–09 | 148.6 |

Example 5. Binding of Anti-MUC16xCD28 Bispecific Monoclonal Antibodies to T Cells and Target Cells In order to determine the binding of the exemplary bispecific antibodies of the present invention on human and Cynomolgus T cells and target cells, flow cytometric analysis was utilized to determine binding of MUC16xCD28 bispecific antibodies to OVACR-3, PEO1, Negative Control Raji cells, Human and Cynomolgus T cells, followed by detection with a phycoerythrin (PE)-labeled or Alexa-647-labeled anti-human IgG antibody. Briefly, $1 \times 10^5$ cells/well were incubated for 30 minutes at 4° C. with a serial dilution of the exemplary MUC16xCD28 bispecific antibodies or an IgG4 isotype control that binds a human antigen with no cross-reactivity to human or cynomolgus CD28), ranging from 133 nM to 32.6 pM for human and cynomolgus T cells, and ranging from 133 nM to 8.14 pM for Muc16 expressing cells and negative control Raji cells. After incubation, the cells were washed twice with cold PBS containing 1% filtered FBS and a PE-conjugated or Alexa647-conjugated anti-human secondary antibody was added to the MUC16 expressing cells or Human/Cyno T cells, respectively, and incubated for an additional 30 minutes. Live/dead dye was added to Human and Cynomolgus T cells incubations. Wells containing no antibody or secondary only were used as a control.

After incubation with MUC16 expressing cells, cells were washed, re-suspended in 200 μL cold PBS containing 1% filtered FBS and analyzed by flow cytometry on a BD FACS Canto II.

After incubation with Human or Cynomolgus T cells, cells were washed, and stained with a cocktail of anti-CD2, ant-CD16, anti-CD4, and anti-CD8 antibodies in Brilliant Stain Buffer for an extra 20 min incubation at 4° C. After wash, cells were re-suspended in 200 μL cold PBS containing 1% filtered FBS, gated in a Live/CD2+/CD4+/CD16– or Live/CD2+/CD8+/CD16– gate and analyzed by Flow cytometry on a BD FACS LSR-Fortessa-X20.

The binding of the exemplary MUC16xCD28 bispecific antibodies to the surface of Human T cells was tested by flow cytometry. bs24963D bound to CD4+ T cells with an EC50 value of $2.61 \times 10^{-7}$M. It bound to CD8+ T cells with an $EC_{50}$ value of $2.53 \times 10^{-7}$M. bs32897D bound weakly to CD4+ T cells with an $EC_{50}$ value of $9.16 \times 10^{-6}$M. It also bound weakly to CD8+ T cells, with an $EC_{50}$ value of $7.58 \times 10^{-6}$M. The results were summarized in Table 13.

TABLE 13

Binding of the Anti-MUC16 × CD28 to Human T Cells

| Antibody PiD | $EC_{50}$ Human CD4+ T cells FACS [M] | $EC_{50}$ Human CD8+ T cells FACS [M] |
|---|---|---|
| bs24963D | 2.61E–07M | 2.53E–07M |
| bs32897D | 9.16E–06M | 7.58E–06M |
| Isotype Control | No binding | No binding |

The binding of the exemplary MUC16xCD28 bispecific antibodies to the surface of Cynomolgus T cells was tested by flow cytometry. The exemplary bs24963D bound to CD4+ T cells with an $EC_{50}$ value of $2.03 \times 10^{-7}$M. It bound to CD8+ T cells with an $EC_{50}$ value of $1.22 \times 10^{-7}$M. The exemplary bs32897D bound OVCAR-3 and PEO1 cells with $EC_{50}$ values of $2.87 \times^{-10}$M and $5.96 \times 10^{-10}$M, respectively. The exemplary bs24963D did not exhibit any binding to MUC16-negative control RAJI cells. The results were summarized in Table 14.

TABLE 14

| Binding of the Anti-MUC16 x CD28 to Cynomolgus T Cells | | |
|---|---|---|
| Antibody PiD | EC$_{50}$ Cynomolgus CD4+ T cells FACS [M] | EC$_{50}$ Cynomolgus CD8+ T cells FACS [M] |
| bs24963D | 2.03E−07M | 1.22E−07M |
| bs32897D | 5.70E−06M | 3.02E−06M |
| Isotype Control | No binding | No binding |

The binding of the exemplary MUC16xCD28 bispecific antibodies to the surface of cell lines expressing MUC16 was tested by flow cytometry. bs24963D bound to OVCAR-3 and PEO1 cells with EC$_{50}$ values of $6.09 \times 10^{-10}$M and $4.67 \times 10^{-10}$M, respectively. bs32897D did not exhibit any binding to MUC16-negative control RAJI cells. bs24963D bound OVCAR-3 and PEO1 cells with EC$_{50}$ values of $2.87 \times 10^{-10}$M and $5.96 \times 10^{-10}$M, respectively. bs24963D did not exhibit any binding to MUC16-negative control RAJI cells. The isotype control antibody did not exhibit any binding to human or cynomolgus T cells, nor did it bind to cell lines expressing MUC16. The results were summarized in Table 15.

TABLE 15

| Binding of the Anti-MUC16 x CD28 to MUC16 Expressing Cells | | | |
|---|---|---|---|
| Antibody PiD | EC$_{50}$ OVCAR-3 cells FACS [M] | EC$_{50}$ PEO1 cells FACS [M] | EC$_{50}$ Raji cells FACS [M] |
| bs24963D | 6.09E−10M | 4.67E−10M | No binding |
| bs32897D | 2.87E−10M | 5.96E−10M | No binding |
| Isotype Control | No binding | No binding | No binding |

Example 6. Primary Bioassay for MUC16xCD28 Bispecific Antibodies

T-cell activation is achieved by stimulating T-cell receptors (TCR) that recognize specific peptides presented by major histocompatibility complex class I or II (MHCI or MHCII) proteins on antigen-presenting cells (APC) (Goldrath et al., Selecting and maintaining a diverse T-cell repertoire, Nature 402, 255-262 (1999)). An activated TCR in turn initiates a cascade of signaling events, which can be monitored by reporter genes, driven by various transcription factors such as activator-protein 1 (AP-1), Nuclear Factor of Activated T-cells (NFAT) or Nuclear factor kappa-light-chain-enhancer of activated B cells (NFκB). The T-cell response is then further refined via engagement of co-receptors expressed either constitutively or inducible on T-cells such as CD28, CTLA-4 (Cytotoxic T-Lymphocyte-Associated Protein 4), PD-1 (Programmed Cell Death Protein 1), LAG-3 (Lymphocyte-Activation Gene 3) or other molecules (Sharpe et al., The B7-CD28 Superfamily, Nat. Rev. Immunol., 2(2): 116-26 (2002)). The co-stimulatory molecule, CD28, is activated by its endogenous ligands CD80 or CD86 expressed on APCs. CD28 potentiates cellular signals such as pathways controlled by the NFκB transcription factor after TCR activation. The CD28 co-signal is important for effective T-cell activation such as T cell differentiation, proliferation, cytokine release and cell-death (Smeets et al., NFκB activation induced by T cell receptor/CD28 costimulation is mediated by protein kinase C-θ, PNAS, 97(7):3394-3399 (2012).

In order to identify antibodies that enhance T cell activity in the presence of both primary stimulation and MUC16 target expression, exemplary anti-MUC16xCD28 bispecific antibodies of the invention were characterized in cell-based assays using human primary T-Cells. The assays evaluate the anti-MUC16/CD28 bispecific antibody's behavior in the presence and absence of primary stimulation and in the presence and absence of target expression.

IL-2 Functional Assay Using Primary Human CD4$^+$ T-Cells:

A primary CD4$^+$ T-cell/APC functional assay was developed to evaluate the effect of CD28 activation on IL-2 production upon engagement with anti-MUC16 x CD28 bispecific antibodies.

a) Human Primary CD4$^+$ T-Cell Isolation:

Human peripheral blood mononuclear cells (PBMCs) were isolated from a healthy donor leukocyte pack. PBMC isolation was accomplished by density gradient centrifugation using 50 mL SepMate™ tubes following the manufacturer's recommended protocol. Briefly, 15 mL of Ficoll-Paque PLUS was layered into 50 mL SepMate tubes, followed by addition of 30 mL of leukocytes diluted 1:2 with D-PBS. Subsequent steps were followed according to SepMate manufacturer's protocol. CD4$^+$ T-cells were subsequently isolated from PBMC's using human CD4 Microbead kits from Miltenyi Biotec following the manufacturer's instructions. Isolated CD4$^+$ T-cells were frozen in FBS containing 10% DMSO at a concentration of $5 \times 10^6$ cells per vial.

b) IL-2 Release from Primary CD4$^+$ T-Cells Treated with CD28 Antibodies:

In this assay, human primary CD4$^+$ T-cells are activated via crosslinking of CD3 molecules, in complex with T-cell receptors (TCR), using αMuc16 x αCD3 bispecific antibody (REGN4018) incubated with human target cells, OVCAR3 or PEO-1, expressing Muc16 on the cell surface. Binding of the Muc16 arm of REGN4018 to target cells expressing Muc16 drives the clustering of the CD3 molecules and provides the first signal, necessary for T-cell stimulation in absence or to an addition of an allogeneic response. However in this assay, in order to complete T-cell activation and increase levels of IL-2 release, co-stimulation provided by cross-linking CD28 molecules, is necessary. Here, the bispecific CD28 antibodies interact with CD28 on CD4$^+$ T-cells and Muc16 on OVCAR3 or PEO-1 cells and drive the clustering—activation of costimulatory molecule, CD28. The combined TCR and CD28 engagement leads to enhanced IL-2 production, which is released into cell culture media. IL-2 is detected and quantified from the cell supernatant using a homogenous, no wash, AlphaLisa kit from PerkinElmer.

Previously isolated and frozen human CD4$^+$ T-cells from Donor 104 were thawed the day of the assay in stimulation media (X-VIVO 15 cell culture media supplemented with 10% FBS, HEPES, NaPyr, NEAA, and 0.01 mM BME) containing 50 U/ml benzonase nuclease. Cells were centrifuged at 1200 rpm for 10 minutes, resuspended in stimulation media and plated into 96-well round bottom plates at a concentration of $1 \times 10^5$ cells/well. OVCAR3 and PEO-1 cells were treated with Mitomycin C in primary stimulation media using 25 μg/mL of Mitomycin C for OVCAR3 and 10 μg/mL for PEO-1 cells. After incubation for 1 hour at 37° C., 5% CO$_2$, target cells were washed 3 times with washing buffer (PBS+2% FBS) and added to the wells containing CD4$^+$ T-cells at a final concentration of $1 \times 10^4$ OVCAR3 or $2.5 \times 10^4$ PEO-1 cells per well. Subsequently, 1:4 serially diluted CD28 bispecific or control antibodies, ranging from 3 pM to 200 nM, were added to wells in the presence of 5 nM constant of REGN4018 (αMuc16 x αCD3) or a negative control antibody (hIgG4 isotype control=H4sH). The final point of the 10-point dilution contained no CD28 antibody, which is the background signal. After plates were incubated for 72 hours at 37° C., 5% $CO_2$, they were centrifuged to pellet the cells and 20 µL of media supernatant was collected. From this, 5 µL was tested in a human IL-2 AlphaLISA assay according to the manufacturer's protocol. The measurements were acquired on the multi-label plate reader Envision and raw RLU (Relative Light Units) values plotted. All serial dilutions were tested in duplicates.

The $EC_{50}$ values of the antibodies were determined by fitting data to a four-parameter logistic equation over a 10-point dose-response curve using GraphPad Prism™ software. Maximal fold induction is calculated using following equation:

$$\text{Fold induction} = \frac{\text{Highest Mean RLU value within tested dose range}}{\text{Mean IL-2 Values (Background)}}$$

Activation of CD4+ T-cells (as measured by IL-2 release) was enhanced by hMUC16xhCD28 in the presence of primary stimulation (anti-MUC16xCD3) and MUC16 expressed on target cells.

c) Result of IL-2 Functional Assay Using Primary Human $CD4^+$ T-Cells:

The ability of anti-Muc16 x anti-CD28 bispecific antibodies to provide co-stimulation through CD28 on isolated $CD4^+$ T-cells in the absence or presence of a TCR stimulating bispecific antibody (REGN4018=anti-Muc16 x anti-CD3) was assessed in a functional IL-2 release assay using isolated human $CD4^+$ T-cells incubated with target cells expressing endogenously Muc16 (OVAR3 and PEO-1 cells) on the cell surface.

Fold induction values are summarized in Table 16 and 17 for $CD4^+$ T-cells co-incubated with OVCAR3 or PEO-1 cells in addition to either 5 nM constant hIgG4 H4sH isotype control or REGN4018 anti-Muc16 x anti-CD3.

When isolated $CD4^+$ T-cells are incubated with OVCAR3 or PEO-1 target cells in absence of a directed TCR stimulation via REGN4018 using a constant amount of H4sH isotype control, detected IL-2 amounts are similar between CD28 parental antibodies, bispecific anti-Muc16 x anti-CD28 antibodies (bs32897D and bs24963D) and the negative H4sH isotype control antibody. (Table 16)

In contrast, increased IL-2 levels are detected in samples treated with anti-Muc16 x anti-CD3 (REGN4018). Under these conditions, if human $CD4^+$ T-cells were co-incubated with OVCAR3 or PEO-1 cells, both CD28 bispecific antibodies increase IL-2 levels more than their respective parental CD28 antibodies. As expected no minimal IL-2 release is observed with the isotype control. (Table 17)

If OVCAR3 are used as target cells, a similar dose-dependent IL-2 release is measured for both CD28 bispecific antibodies (bs32897D: 5.63x and $EC_{50}$=606 pM) and bs24963D: 5.32x and $EC_{50}$=401 pM). Whereas with PEO-1 cells, a difference in fold induction of IL-2 levels could be observed between both bispecific molecules. Here, bs24963D (10.94x and $EC_{50}$=996 pM) gives rise to higher IL-2 values than bs32897D (5.22x and EC50 could not be determined, because the dose-response curve did not reach saturation).

In absence of TCR stimulation, either through an allogeneic response or driven by anti-MUC16xCD3, no measurable IL-2 release is observed with CD28 antibodies in wells containing constant amounts of isotype control in presence of OVCAR3 or PEO-1 cells (Table 16). Table 16 summarizes the $EC_{50}$ values and fold induction of IL-2 release from $CD4^+$ T-cells co-incubated with OVCAR3 or PEO-1 and 5 nM constant isotype control.

TABLE 16

$EC_{50}$ and fold induction results for IL-2 release from primary human $CD4^+$ T-cells in presence of 5 nM human IgG4 isotype control:

| | OVCAR3 | | PEO-1 | |
| Antibodies | $EC_{50}$ [M] | Fold induction | $EC_{50}$ [M] | Fold induction |
| --- | --- | --- | --- | --- |
| bs32897D | N/C | 1.06 | N/C | 1.12 |
| bs24963D | N/C | 1.33 | N/C | 1.12 |
| Parental 1 hCD28 (for bs32897D) | N/C | 1.10 | N/C | 1.30 |
| Parental 2 hCD28 (for bs24963D) | N/C | 1.12 | N/C | 1.03 |
| H4sH Isotype Control | N/C | 1.12 | N/C | 1.48 |

Table 16. Tabulated $EC_{50}$ values and maximal fold induction of IL-2 release over background signal from $CD4^+$ T-cells co-incubated with OVCAR3 or PEO-1 and 5 nM constant of H4sH isotype control.

N/C=Not Calculated

In contrast, measurable IL-2 levels (RLU) are detected in samples treated with anti-MUC16xCD3. Under these conditions, if human $CD4^+$ T-cells were co-incubated with OVCAR3 or PEO-1 cells, both CD28 bispecific antibodies increase IL-2 levels more than its parental CD28 antibody. As expected no IL-2 release is observed with the isotype control (Table 17). Table 17 summarizes the $EC_{50}$ values and fold induction of IL-2 release from $CD4^+$ T-cells co-incubated with OVCAR3 or PEO-1 and 5 nM constant 5 nM anti-MUC16xCD3.

TABLE 17

$EC_{50}$ and fold induction results for IL-2 release from primary human $CD4^+$ T-cells in presence of 5 nM REGN4018 (anti-Muc16 × anti-CD3):

| | OVCAR3 | | PEO-1 | |
| Antibodies | $EC_{50}$ [M] | Fold induction | $EC_{50}$ [M] | Fold induction |
| --- | --- | --- | --- | --- |
| bs32897D | 6.07E-10 | 5.63 | N/D | 5.22 |
| bs24963D | 4.01E-10 | 5.32 | 9.96E-10 | 10.94 |
| Parental 1 hCD28 (for bs32897D) | N/D | 1.58 | N/D | 1.42 |
| Parental 2 hCD28 (for bs24963D) | N/D | 2.46 | 1.07E-10 | 2.05 |
| H4sH Isotype Control | N/C | 1.09 | N/C | 1.11 |

Table 17. Tabulated $EC_{50}$ values and maximal fold induction of IL-2 release over background signal from $CD4^+$ T-cells co-incubated with OVCAR3 or PEO-1 and 5 nM constant of REGN4018 (anti-Muc16 x anti-CD3). Abbreviations:

N/D=Not Determined, because dose-response curve did not reach saturation or showed bell-shaping; N/C=Not Calculated

Example 7. Anti-MUC16xCD28 Bispecific Antibodies Potentiate T Cell Activation and Cytotoxicity on Ovarian Tumor Cells in the Presence of TCR Stimulation by Anti-MUC16xCD3

To examine if exemplary anti-MUC16xCD28 bispecific antibodies of the invention could enhance anti-MUC16xCD3 mediated T cell activation and cytotoxicity on ovarian tumor cells, FACS was used to examine the viability of tumor cells and phenotype T cells after in vitro co-culture with a dose titration of MUC16xCD3 alone or in combination with MUC16xCD28 (FIG. 2A. Human peripheral blood mononuclear (PBMC) cells containing T cells were co-cultured with PEO-1 ovarian cancer cells expressing endogenous levels of MUC16 (Coscia, F. et al, Nat. Commun. (2016), August 26; 7:12645).

Two FACS based cytotoxicity studies were conducted. In the first study, FACS based cytotoxicity was conducted on MUC16+ cells in the presence of human peripheral blood mononuclear cells (PBMCs) and anti-MUC16xCD3 in the presence or absence of anti-MUC16 x CD28 stimulation (FACS based cytotoxicity on MUC16 cells+human PBMC+/–MUC16xCD28 stimulation (MUC16xCD28 x Muc16xCD3 Matrix set-up)). The second study is otherwise identical to the first study except that Cynomolgus PBMCs are used instead of human PBMCs (FACS based cytotoxicity on MUC16 cells+Cynomolgus PBMC+/–MUC16xCD28 stim (MUC16xCD28 x MUC16xCD3 Matrix set-up)).

Experimental Procedure

In order to monitor the killing of MUC16+ cells in the presence of a combination of an anti-MUC16xCD3 antibody and an exemplary anti-MUC16xCD28 antibody of the invention, cell lines endogenously expressing MUC16 (PEO1, MUC16$^+$) were labeled with 1 µM of Violet Cell Tracker and plated overnight at 37° C. Separately, human PBMCs (New York Blood Center) or cynomolgus monkey PBMCs (Covance, Cranford NJ) were plated in supplemented RPMI media at $1 \times 10^6$ cells/mL and incubated overnight at 37° C. in order to enrich for lymphocytes by depleting adherent macrophages, dendritic cells, and some monocytes. The next day, the target cells were co-incubated with adherent cell-depleted naïve human PBMC (Effector/Target cell 4:1 ratio) and a serial dilution of either anti-MUC16xCD3 or non-targeting CD3-based bispecific (bs17664D), alone or in combination with a fixed concentration (2.5 µg/ml) of an exemplary anti-MUC16xCD28 bispecific for 96 hours at 37° C. Post incubation, the cells were removed from the cell culture plates using Trypsin-EDTA dissociation buffer and analyzed by Flow Cytometry (FACS).

For FACS analysis, cells were stained with a viability far red cell tracker (Invitrogen) and directly conjugated antibodies to CD2, CD4, CD8 and CD25 (BD). Samples were run with calibration beads for cell counting. For the assessment of specificity of killing, target cells were gated as Violet cell tracker positive populations. Percent of live target cells was calculated as follows: percentage of viable cells= (R1/R2)*100, where R1=percentage of live target cells in the presence of antibody, and R2=percentage of live target cells in the absence of test antibody. T cell activation was measured by the percent of activated (CD25$^+$) T cells out of CD2$^+$/CD4$^+$ or CD2$^+$/CD8$^+$ T cells. Upregulation of the PD-1 marker were assessed by incubating cells with directly conjugated antibodies to CD2, CD4, CD8, CD25 and PD-1, and by reporting the percent of PD-1+ T cells out of total T cells (CD2+). T cell count was measured by calculating the number of live CD4$^+$ or CD8$^+$ cells per calibration bead. The levels of cytokines accumulated in the media were analyzed using the BD cytometric Bead Array (CBA) human Th1/Th2/Th17 Cytokine kit, following the manufacturer's protocol.

Results, Summary and Conclusions:

The anti-MUC16xCD3 bispecific antibody was tested for its ability to induce naïve human T cells to kill PEO1 target cells expressing human MUC16 as a single agent, or in the presence of a costimulatory MUC16xCD28 antibody. Anti-MUC16xCD3 bispecific antibody activated and directed human T cells to deplete PEO1 cells. Moreover, MUC16xCD3 alone induced moderate T cell killing of PEO-1 cancer cells, reducing their viability to ~60% in a dose dependent manner (FIG. 2B and Table 18). Target cell killing was observed in the presence of the anti-MUC16xCD3 bispecific antibody and PEO1 cells were killed in a dose-dependent manner with EC$_{50}$s in the picomolar (pM) level (FIG. 2B). Target cell killing was not observed when anti-MUC16xCD3 was not present (FIG. 2B). The observed target-cell lysis was associated with upregulation of CD25+ and PD-1+ cells on CD2+ T cells, again with EC$_{50}$s in the picomolar (pM) level (Table 18).

Anti-MUC16xCD3 induced the release of human cytokines. The cytotoxic activity observed with anti-MUC16xCD3 as a single agent was enhanced in the presence of exemplary anti-MUC16xCD28 costimulatory molecules of the present invention, bs24963D and bs32897D.

It was found that addition of the exemplary anti-MUC16xCD28 of the invention increased the potency and depth of cytotoxicity induced by MUC16xCD3 resulting in further reduction of PEO-1 cancer cell viability to less than 20% (greater than 3-fold increase in T cell killing) (FIG. 2B). Furthermore, exemplary anti-MUC16xCD28 of the invention increased the levels of IFNγ release induced by MUC16xCD3 by over 10-fold (FIG. 2C). MUC16xCD28 and MUC16xCD3 combination expanded CD4 and CD8 T cells and increased the expression level of the activation marker CD25 (FIGS. 2D-E). Notably, MUC16xCD28 in combination with a non-targeting CD3 bispecific did not induce T cell cytotoxicity or activation (FIG. 2B).

In summary, co-stimulation increased T cell activation, PD-1 upregulation, and cytokine release when compared to what was observed with MUC16xCD3 as a single agent. Tables 18 and 19 and FIGS. 2A-2E) summarizes the experimental results using human PBMCs.

TABLE 18

| | Effects of Anti-MUC16 x CD28 on Cytotoxicity of Anti-MUC16 x CD3 to PEO1 Cells in the Presence of Human PBMCs | | | |
| PiD | PEO1 Kill EC$_{50}$ [M] | PEO1 min. % viability | T Cell Activation EC$_{50}$[M] (CD8+/ CD25+) | PD-1 Upregulation max % (CD4+/ PD1+) |
| --- | --- | --- | --- | --- |
| MUC16 × CD3 | 1.27E–10 | 57% | 2.94E–10 | 27.2% |
| MUC16 × CD3 + bs24963D | 1.07E–10 to 5.31E–11 | 9.8% | 1.86E–10 to 3.94E–11 | 65.7% |
| MUC16 × CD3 + bs32897D | 2.6E–10 to 7.40E–11 | 17.7% | 4.82E–10 to 4.42E–11 | 58.4% |

The anti-MUC16xCD3 bispecific antibody was also tested for its ability to induce naïve cynomolgus T cells to kill target cells expressing human MUC16 as a single agent, or in the presence of a costimulatory anti-MUC16xCD28 bispecific antibody. The same assays were performed and similar results were obtained using PBMC from cynomolgus monkeys (FIGS. 2F-H). FIG. 2I shows that the exemplary anti-MUC16xCD28 bispecific antibody of this invention binds to cellular targets as measured by flow cytometry. These results demonstrated that anti-MUC16xCD28 bispecific antibodies of the invention can potently enhance MUC16xCD3 mediated T cell activation not only by way of proliferation and cytokine release but also cytotoxicity. At the selected antibody titration, the anti-MUC16xCD3 bispecific antibody activated human T cells but did not direct T cells to deplete PEO1 cells (Table 19). Co-stimulation with an exemplary anti-MUC16xCD28 antibody of the invention resulted in increased T-cell activation, an enhancement of cytotoxic activity, and upregulation of the PD-1 marker on T cells (Table 19).

TABLE 19

Effects of anti-MUC16 × CD28 on Cytotoxicity
of anti-MUC16 × CD3 to PEO1 Cells
in the Presence of Cynomolgus PBMCs

| PiD | PEO1 Kill EC50 [M] | PEO1 min. % viability | T cell activation EC50[M] (CD8+/ CD25+) | PD-1 upregulation max % (CD4+/ PD1+) |
|---|---|---|---|---|
| MUC16 × CD3 | 2.09E−10 | 69% | 1.59E−10 | 24.4% |
| MUC16 × CD3 + bs24963D | 1.29E−10 to 3.34E−11 | 18.1% | 1.04E−10 to 9.07E11 | 44.3% |
| MUC16 × CD3 + bs32897D | 3.92E−10 to 1.09E−10 | 29.7% | 2.81E−10 to 7.67E−11 | 40.3% |

Example 8. In Vivo Study of Anti-MUC16xCD28 Antibody

Combining tumor antigen targeted anti-CD3xMUC16 and anti-CD28xMUC16 bispecific antibodies enhanced tumor clearance in a mouse model. As shown in details below, OVCAR-3 tumor growth was significantly inhibited in mice administered with anti-CD3xMUC16 and exemplary anti-CD28xMUC16 of the invention compared to mice administered with anti-CD3xMUC16 alone, or control isotype.

To examine if MUC16xCD28 could enhance anti-tumor efficacy of MUC16xCD3 in vivo, two distinct tumor models, a tumor xenogenic ascites model and a tumor syngeneic mouse model, were used as described in details below.

Tumor Xenogenic Ascites Model

In a tumor xenogenic ascites model, high-grade serous carcinoma OVCAR-3 ovarian cancer cells of human origin, expressing endogenous high levels of MUC16, are implanted intraperitoneally in NSG mice pre-engrafted with human PBMC (Crawford A, Haber L, Kelly M P, Vazzana K, Canova L, Ram P, Pawashe A, Finney J, Jalal S, Chiu D, Colleton C A, Garnova E, Makonnen S, Hickey C, Krueger P, Delfino F, Potocky T, Kuhnert J, Godin S, Retter M W, Duramad P, MacDonald D, Olson W C, Fairhurst J, Huang T, Martin J, Lin J C, Smith E, Thurston G, Kirshner J R. A Mucin 16 bispecific T cell-engaging antibody for the treatment of ovarian cancer. Science Translational Medicine 19 Jun. 2019:Vol 11, Issue 497, eaau7534). OVCAR-3 cells were engineered with luciferase reporter to track tumor growth over time using in vivo bioluminescence (BLI)

Experimental Procedure

Experiments were performed as described in (Crawford A, Haber L, Kelly M P, Vazzana K, Canova L, Ram P, Pawashe A, Finney J, Jalal S, Chiu D, Colleton C A, Garnova E, Makonnen S, Hickey C, Krueger P, Delfino F, Potocky T, Kuhnert J, Godin S, Retter M W, Duramad P, MacDonald D, Olson W C, Fairhurst J, Huang T, Martin J, Lin J C, Smith E, Thurston G, Kirshner J R. A Mucin 16 bispecific T cell-engaging antibody for the treatment of ovarian cancer. Science Translational Medicine 19 Jun. 2019:Vol 11, Issue 497, eaau7534). Briefly, mice were injected IP with 150 mg/kg of the luciferase substrate D-luciferin (Perkin Elmer), suspended in PBS. Ten minutes later, BLI imaging of the mice was performed under isoflurane anesthesia using the Xenogen IVIS system (Perkin Elmer). Image acquisition was carried out with the field of view at D, subject height of 1.5 cm, and medium binning level for 0.5-min exposure time. BLI signals were extracted using Living Image software (Xenogen; Alameda, CA). Regions of interest were drawn around each tumor mass and photon intensities were recorded as $p/s/cm^2/sr$ (photons per second per square centimeter per steradian). Mice that did not receive OVCAR-3/Luc cells served as a baseline reading for BLI activity. These baseline mice (N=3) with no tumors were imaged on each day and the lower limit of detection (LOD) was calculated as the average BLI reading across all imaged tumor free mice.

Eight to ten (8-10)-week-old NSG (NOD SCID gamma chain knock-out) mice (Jackson Laboratory, MD) were injected with $5\times10^6$ human PBMCs (ReachBio, Seattle, WA). Ten to fourteen (10-14) days later, mice were bled via the tail vein to determine human T cell engraftment. Within two weeks of PBMCs being transferred, $2\times10^6$ ascites cells from the OVCAR-3/Luc cell line, previously passaged in vivo, were administered intraperitoneally (IP) within two weeks (Day 0). Mice were checked for T cell engraftment by flow cytometry then assigned to groups using BLI to ensure similar tumor burden. Four days post tumor implantation, mice were divided into groups of 5 animals each with a median BLI of $1.49\times10^5$ or $3.03\times10^5$ $p/s/cm^2/sr$ for the two studies. Mice were treated with the indicated bispecific or control antibodies on day 5 and 8. Mice were administered anti-MUC16xCD3 or a CD3-binding control with or without exemplary anti-MUC16xCD28 (bs24963D) of the invention twice via intravenous (IV) injection. Imaging occurred multiple times throughout the study to track tumor growth.

Serum cytokine levels from blood were also obtained at the indicated time point. At the indicated time points, blood was collected by submandibular puncture into microtainer serum tubes (BD 365967). Cytokine levels were analyzed using V-plex Human ProInflammatory-10 Plex kit following the manufacturer's instructions (Meso Scale Diagnostics, Rockville, MA).

All procedures were carried out in accordance with the Guide for the Care and Use of Laboratory Animals of the NIH. The protocol was approved by the Regeneron Pharmaceuticals Institutional Animal Care and Use Committee. A total of 2 studies with 5 mice per group were completed.

Results, Summary and Conclusions

For xenogenic tumor studies, two models were used. For the first xenogenic model, NSG mice were injected intraperitoneally (IP) with OVCAR-3/Luc cells previously passaged in vivo (Day 0) thirteen days after engraftment with human PBMCs. Mice were treated IV on Days 5 and 8. Mice received either 12.5 µg anti-MUC16xCD3 or 12.5 µg CD3- binding control (hIgG4$^{P-PVA}$ isotype). Some of the mice were also administered the exemplary anti-MUC16xCD28 of the invention (bs24963D) at 100 µg. Tumor burden was assessed by BLI on Days 4, 8, 12, 15, 20 and 25 post tumor implantation. Reduced BLI-evident tumors were not observed when the exemplary bs24963D was administered without anti-MUC16xCD3. In contrast, while treatment with 12.5 µg anti-MUC16xCD3 significantly reduced BLI-evident tumors, the exemplary anti-MUC16xCD28 of the invention significantly enhanced the efficacy over anti-MUC16xCD3 alone (Tables 20-22).

Table 20 summarizes the level of bioluminescence on day 4 post tumor implantation in the first OVCAR-3/Luc xenogenic model.

TABLE 20

OVCAR-3/Luc Model. Level of Bioluminescence on Day 4 Post Tumor Implantation

| Antibody (µg) | Avg Radiance [p/s/cm2$^2$/sr] 4 Days Post-Implantation (median ± SEM) |
|---|---|
| CD3-binding control (12.5) | $1.51 \times 10^5 \pm 2.81 \times 10^4$ |
| Anti-MUC16 × CD3 (12.5) | $1.5 \times 10^5 \pm 1.05 \times 10^4$ |
| CD3-binding control (12.5) + anti-MUC16 × CD28 (100) | $1.53 \times 10^5 \pm 2.01 \times 10^4$ |
| Anti-MUC16 × CD3 (12.5) + anti-MUC16 × CD28 (100) | $1.27 \times 10^5 \pm 2.29 \times 10^4$ |

Table 21 summarizes the level of bioluminescence on day 25 post tumor implantation in the first OVCAR-3/Luc xenogenic model.

TABLE 21

OVCAR-3/Luc Model. Level of Bioluminescence on Day 25 Post Tumor Implantation

| Antibody (µg) | Avg Radiance [p/s/cm2$^2$/sr] 25 Days Post-Implantation (median ± SEM) |
|---|---|
| CD3-binding control (12.5) | $7.71 \times 10^6 \pm 1.07 \times 10^6$ |
| Anti-MUC16 × CD3 (12.5) | $7.44 \times 10^3 \pm 3.11 \times 10^3$ |
| CD3-binding control (12.5) ± anti-MUC16 × CD28 (100) | $6.04 \times 10^6 \pm 8.32 \times 10^5$ |
| Anti-MUC16 × CD3 (12.5) ± anti-MUC16 × CD28 (100) | $1.31 \times 10^3 \pm 3.05 \times 10^1$ |

Table 22 summarizes the fold change in BLI between Day 4 and Day 25 post tumor implantation in the first OVCAR-3/Luc xenogenic model.

TABLE 22

OVCAR-3/Luc Model. Fold Change in BLI between Day 4 and Day 25 Post Tumor Implantation

| Antibody (µg) | Fold Change in Avg Radiance [p/s/cm2$^2$/sr] from Day 4 to D25 Post-Implantation (mean ± SD) |
|---|---|
| CD3-binding control (12.5) | 50.72 ± 29.67 |
| Anti-MUC16 × CD3 (12.5) | −0.94 ± 0.05 |
| CD3-binding control (12.5) + anti-MUC16 × CD28 (100) | 35.38 ± 8.18 |
| Anti-MUC16 × CD3 (12.5) + anti-MUC 16xCD28 (100) | −0.99 ± 0.00 |

For the second xenogenic model, NSG mice were injected with OVCAR-3/Luc cells previously passaged in vivo (Day 0) ten days after engraftment with human PBMCs. Mice were treated IV with 0.5 mg/kg anti-MUC16xCD3 or administered 0.5 mg/kg CD3-binding control on Days 5 and 8. Tumor burden was assessed by BLI on Days 4, 8, 11, 14, 21, 28 and 34. Some of the mice were also administered the exemplary anti-MUC16xCD28 of the invention (bs24963D) at 0.2 mg/kg, 1 mg/kg, or 5 mg/kg. The exemplary bs24963D did not decrease tumor burden when administered without anti-MUC16xCD3. In contrast, while treatment with 0.5 mg/kg anti-MUC16xCD3 significantly reduced BLI-evident tumors, the exemplary anti-MUC16xCD28 enhanced the efficacy over anti-MUC16xCD3 alone (Tables 23-25 and FIG. 4A).

Table 23 summarizes the level of bioluminescence on day 4 post tumor implantation in the second OVCAR-3/Luc xenogenic model.

TABLE 23

OVCAR-3/Luc Model. Level of Bioluminescence on Day 4 Post Tumor Implantation

| Antibody (mg/kg) | Avg Radiance [p/s/cm2$^2$/sr] 4 Days Post-Implantation (median ± SEM) |
|---|---|
| CD3-binding control (0.5) | $3.65 \times 10^5 \pm 5.50 \times 10^4$ |
| Anti-MUC16 × CD3 (0.5) | $3.76 \times 10^5 \pm 2.40 \times 10^4$ |
| CD3-binding control (0.5) + anti-MUC16 × CD28 (5) | $2.71 \times 10^5 \pm 2.65 \times 10^4$ |
| Anti-MUC16 × CD3 (0.5) ± anti-MUC16 × CD28 (5) | $3.18 \times 10^5 \pm 4.45 \times 10^4$ |
| Anti-MUC16 × CD3 (0.5) ± anti-MUC16 × CD28 (1) | $3.07 \times 10^5 \pm 4.37 \times 10^4$ |
| Anti-MUC16 × CD3 (0.5) ± anti-MUC16 × CD28 (0.2) | $2.86 \times 10^5 \pm 4.95 \times 10^4$ |

Table 24 summarizes the level of bioluminescence on day 25 post tumor implantation in the second OVCAR-3/Luc xenogenic model

TABLE 24

OVCAR-3/Luc Model. Level of Bioluminescence on Day 34 Post Tumor Implantation

| Antibody (mg/kg) | Avg Radiance [p/s/cm2$^2$/sr] 34 days post-implantation (median ± SEM) |
|---|---|
| CD3-binding control (0.5) | $1.79 \times 10^7 \pm 2. 17 \times 10^6$ |
| Anti-MUC16 × CD3 (0.5) | $9.60 \times 10^4 \pm 4.55 \times 10^4$ |
| Anti-MUC16 × CD3 (0.5) ± anti-MUC16 × CD28 (5) | $2.34 \times 10^7 \pm 1.12 \times 10^6$ |
| Anti-MUC16 × CD3 (0.5) ± anti-MUC16 × CD28 (5) | $2.45 \times 10^3 \pm 4.49 \times 10^3$ |
| Anti-MUC16 × CD3 (0.5) ± anti-MUC16 × CD28 (1) | $1.62 \times 10^3 \pm 2.32 \times 10^3$ |
| Anti-MUC16 × CD3 (0.5) ± anti-MUC16 × CD28 (0.2) | $1.29 \times 10^3 \pm 4.77 \times 10^1$ |

Table 25 summarizes the fold change in BLI between Day 4 and Day 34 post tumor implantation in the second OVCAR-3/Luc xenogenic model.

TABLE 25

OVCAR-3/Luc Model. Fold Change in BLI between Day 4 and Day 34 Post Tumor Implantation

| Antibody (mg/kg) | Fold change in Avg Radiance [p/s/cm2$^2$/sr] from Day 4 to D34 Post-Implantation (mean ± SD) |
|---|---|
| CD3-binding control (0.5) | 51.35 ± 27.59 |
| Anti-MUC16 × CD3 (0.5) | −0.64 ± 0.31 |

TABLE 25-continued

| OVCAR-3/Luc Model. Fold Change in BLI between Day 4 and Day 34 Post Tumor Implantation | |
| --- | --- |
| Antibody (mg/kg) | Fold change in Avg Radiance [p/s/cm2$^2$/sr] from Day 4 to D34 Post-Implantation (mean ± SD) |
| Anti-MUC16 × CD3 (0.5) + anti-MUC16 × CD28 (5) | 64.62 ± 36.38 |
| Anti-MUC16 × CD3 (0.5) + anti-MUC16 × CD28 (5) | −0.97 ± 0.04 |
| Anti-MUC16 × CD3 (0.5) + anti-MUC16 × CD28 (1) | −0.99 ± 0.02 |
| Anti-MUC16 × CD3 (0.5) + anti-MUC16 × CD28 (0.2) | −1.00 ± 0.00 |

Other results of the second xenogenic model using different dosages are shown in FIG. 3A. Mice treated with MUC16xCD3 at 2.5 μg on day 5 and 8 post tumor implant had significantly reduced tumor burden compared to mice treated with a CD3-binding control antibody (EG-FRvIIIxCD3) but did not completely clear OVCAR-3/Luc tumor cells (FIG. 3A). Combining MUC16xCD3 at 2.5 μg with MUC16xCD28 at 100 μg further inhibited tumor growth with more durable rejection of tumor cells over time (FIG. 3A). In the same experiment, the serum cytokine levels were also obtained. FIG. 3B shows the cytokine levels (pg/ml) in mice treated with different antibodies and/or antibodies combinations. FIG. 3C shows tumor burden and correlation to CA-125 levels in serum on day 26.

To test the ability of CD28- and CD3-bispecifics to promote tumor killing in vivo, the well-established xenogenic intraperitoneal ovarian OVCAR-3 tumor model was used. In this model, tumor cells are introduced into immunodeficient mice that are reconstituted with human PBMCs. Like other ovarian cancer cell lines, the OVCAR-3 cells express MUC16. Prior to implantation the OVCAR-3 cells were engineered with a luciferase reporter to allow in vivo tracking of tumor growth over time using bioluminescence (BLI). Implanted OVCAR-3 tumors grew unabated in mice treated with EGFRvIIIxCD3 bispecific, a control CD3-bispecific that did not bind to these cells, and in mice treated only with the MUC16xCD28 bispecific (FIG. 3A). Although the MUC16xCD3 bispecific alone demonstrated significant anti-tumor activity it did not completely clear the OVCAR-3 tumors (FIG. 3A) whereas the addition of the MUC16xCD28 bispecific to the MUC16xCD3 bispecific enhanced the in vivo anti-tumor effect (FIG. 3A) over MUC16xCD3 alone. Consistent with enhanced anti-tumor activity, the combination of both bispecifics also increased the secretion of circulating cytokines (FIG. 3B).

The MUC16-bispecifics bind to the remaining "nub" of MUC16 (the cell surface remnant after cleavage and release of CA-125) on the ovarian cancer cell surface after proteolytic cleavage has released the prognostic ovarian cancer biomarker CA-125 (I. Mylonas et al., Immunohistochemical expression of the tumour marker CA-125 in normal, hyperplastic and malignant endometrial tissue. *Anticancer Res* 23, 1075-1080 (2003)), but does not bind soluble CA-125 (FIGS. 9A and 9B). To determine whether the MUC16xCD28 bispecific perturbed the ability to use CA-125 as a biomarker for ovarian tumor burden, CA-125 levels in the mice were measured. CA-125 levels correlated with tumor burden regardless of treatment. The lowest CA-125 levels were seen in the mice treated with the combination of bispecifics (FIG. 3C) as previously demonstrated for MUC16xCD3 bispecific.

Syngeneic Mouse Model

Experimental Procedure

Syngeneic studies were carried out in mice genetically modified to express human CD3 and a portion of human MUC16 for the MC38 studies using VelociGene® technology, as described previously (Valenzuela et al., (2003) Nat. Biotechnol. June; 21(6):652-9), (Crawford A, Haber L, Kelly M P, Vazzana K, Canova L, Ram P, Pawashe A, Finney J, Jalal S, Chiu D, Colleton C A, Garnova E, Makonnen S, Hickey C, Krueger P, Delfino F, Potocky T, Kuhnert J, Godin S, Retter M W, Duramad P, MacDonald D, Olson W C, Fairhurst J, Huang T, Martin J, Lin J C, Smith E, Thurston G, Kirshner J R. A Mucin 16 bispecific T cell-engaging antibody for the treatment of ovarian cancer. Science Translational Medicine 19 Jun. 2019:Vol 11, Issue 497, eaau7534). Mice expressing human CD3, human CD28 and a portion of human MUC16 were used for the ID8-VEGF studies. For the humanization of CD3, a targeting vector was engineered that replaced the extracellular portions of the mouse CD3 genes (γδε) with the corresponding human region of the genes. For the humanization of CD28, a targeting vector was engineered that replaced the extracellular portions of the mouse CD28 gene with the corresponding human region of the gene. For MUC16, the SEA repeats 13-17 of the mouse was replaced with the human SEA repeats 12-16. For each humanized mouse, correct gene targeting in F1H4 (C57BL/6×129 hybrid) embryonic stem (ES) cell clones was identified by a loss of allele assay as described previously (Poueymirou et al (2007), Nat. Biotechnol. January; 25(1):91-9). Targeted ES cells were injected into 8-cell stage Swiss Webster embryos to produce fully F0 generation heterozygous mice for breeding with C57BL/6N mice (Taconic, Rensselaer, NY) to homozygosity. Mice expressing the human extracellular portion of CD3 (γδε), the human extracellular portion of CD28, and a portion of human MUC16 were then bred to homozygosity (referred to as hCD3/hMuc16 or hCD3/hCD28/hMUC16 humanized mice).

To examine efficacy in an immune-competent model, a knock-in mouse was generated. The T cells of this mouse express human CD3 and in place of murine MUC16, a chimeric molecule is expressed that contains a portion of human MUC16 where the exemplary bispecific antibody of the invention binds. Accordingly, the anti-MUC16xCD3 molecule can be used in this study. To investigate whether addition of a targeting CD28 bispecific molecule can enhance efficacy in these mice, a surrogate bispecific antibody was also generated. The surrogate antibody recognized human MUC16 but murine CD28 to examine the effects of CD28 costimulation and is sometimes referred to as anti-MUC16xmCD28. For the syngeneic tumor model, the MC38 cell line engineered to express a portion of human MUC16 was used. Mice were implanted with the MC38/huMUC16 cells subcutaneously (SC) and treated with 0.01 mg/kg of anti-MUC16xCD3 on day of implantation, twice per week until day 21. Treatment with 0.01 mg/kg anti-MUC16xCD3 resulted in significant anti-tumor efficacy and addition of MUC16xmCD28 enhanced this effect. (See FIGS. 6A, 6B, 6C and 6D). Implantation and measurement of syngeneic tumors Mice expressing human CD3 and a human-murine chimera of MUC16 in the corresponding mouse loci were implanted with 1×10$^6$ MC38/huMUC16 cells subcutaneously. Mice were administered anti-MUC16xCD3 or a isotype control intraperitoneally (IP) with or without a surrogate bispecific antibody recognizing human MUC16 and mouse CD28, twice per week throughout study until day 21. Treatment began on the day of implantation. Tumor growth was measured with calipers twice per week. Mice were sacrificed 50 days after tumor implantation.

Calculation of Syngeneic Tumor Growth and Inhibition

In order to determine tumor volume by external caliper, the greatest longitudinal diameter (length) and the greatest transverse diameter (width) were determined. Tumor volume based on caliper measurements were calculated by the formula: Volume=(length×width$^2$)/2. Tumor growth was monitored over time using caliper measurements of X and Y diameter. Mice were euthanized when tumor size was greater than 2000 mm$^3$. Statistical significance was determined using an unpaired nonparametric Mann-Whitney t-test.

Results

The tumor sizes in MC38/huMUC16 model under different treatments were summarized in Table 26.

TABLE 26

| MC38/huMUC16 Model. Tumor Size (mm$^3$) at Day 21 | |
| --- | --- |
| Antibody (µg) | Tumor Size (mm$^3$) (mean ± SEM) |
| Isotype control (0.5) | 1191 ± 424 |
| Anti-MUC16 × CD3 (0.01) | 639.5 ± 186.8 |
| Anti-MUC16 × mCD28 (0.5) | 648.5 ± 129.7 |
| Anti-MUC16 × CD3 (0.01) + anti-MUC16 × mCD28 (0.5) | 167.3 ± 71.9 |

It was tested if exemplary anti-MUC16xCD28 bispecific antibodies of the invention could enhance anti-tumor efficacy of MUC16xCD3 in a syngeneic mouse model in mice with a fully intact immune system. Mice were genetically engineered to express human CD3 and human MUC16 in place of the mouse genes using Velocigene technology (Crawford A, Haber L, Kelly M P, Vazzana K, Canova L, Ram P, Pawashe A, Finney J, Jalal S, Chiu D, Colleton C A, Garnova E, Makonnen S, Hickey C, Krueger P, Delfino F, Potocky T, Kuhnert J, Godin S, Retter M W, Duramad P, MacDonald D, Olson W C, Fairhurst J, Huang T, Martin J, Lin J C, Smith E, Thurston G, Kirshner J R. A Mucin 16 bispecific T cell-engaging antibody for the treatment of ovarian cancer. Science Translational Medicine 19 Jun. 2019:Vol 11, Issue 497, eaau7534). MC38 colon carcinoma cell line was engineered to express human MUC16 (pLVX.EF1a.MUC16, MC38/hMUC16) and implanted subcutaneously. Mice were dosed by intraperitoneal injection 2× per week starting on the day of implant (day 0) with isotype control (Iso Ctrl), 0.01 mg/kg of MUC16xCD3, 0.5 mg/kg of MUC16xmCD28 or combination. Tumor growth was monitored over time (FIG. 6A). MUC16xCD3 or MUC16xCD28 monotherapy significantly inhibited tumor growth. Tumor growth was further significantly inhibited by MUC16xCD3 and MUC16xCD28 combination treatment (Table 26). In the same experiment, the serum cytokine levels were also obtained. FIG. 6B shows the cytokine levels in mice treated with different antibodies and/or antibodies combinations.

Appropriate humanized mice MC38/hMUC16 received implanted tumor cells, and were treated with control, the individual CD3- or CD28-bispecifics, or the combinations (FIGS. 6A, 6C, and 6D). In the MUC16 tumor model, the combination of CD3- and CD28-bispecifics provided the best anti-tumor responses (FIG. 6A), as was also noted in assays of cytokine production (FIGS. 6C and 6D).

To investigate whether addition of a targeting of the MUC16xCD28 lead can enhance efficacy in a syngeneic model, mice expressing human CD3 and in place of murine MUC16, human CD28 in place of murine CD28 and a chimeric molecule that contains a portion of human MUC16 where the exemplary bispecific antibody of the invention binds were used. The ID8-VEGF cell line was engineered to express human MUC16 (ID8-VEGF/hMUC16) and implanted intra-peritoneally. Mice were dosed on days 3, 6, and 10 after tumor implantation with 1 mg/kg EGFRvIIIxCD3 or MUC16xCD3 alone or in combination with MUC16xCD28. Tumor growth was monitored using weight gain (FIG. 5). Tumor growth was inhibited by MUC16xCD3 and the combination with MUC16xCD28 further delayed tumor growth.

Notably, unlike the previous in vitro and in vivo analyses in which the CD28-bispecifics had very limited single-agent activity (see above), the CD28-bispecifics in this syngeneic MC38/MUC16 model had more notable activity as single agents. This suggested that "signal 1" was already being activated to some degree in these MC38 models. Consistent with this, it has been previously shown that MC38 tumor cells express high levels of re-activated endogenous retroviral proteins such as p15E, and that C57BL6 mice can generate endogenous T cells that recognize and respond to this neo-epitope (J. C. Yang, D. Perry-Lalley, The envelope protein of an endogenous murine retrovirus is a tumor-associated T-cell antigen for multiple murine tumors. *J Immunother* 23, 177-183 (2000); H. J. Zeh, 3rd, D. Perry-Lalley, M. E. Dudley, S. A. Rosenberg, J. C. Yang, High avidity CTLs for two self-antigens demonstrate superior in vitro and in vivo antitumor efficacy. *J Immunol* 162, 989-994 (1999)). Indeed, it was confirmed that in the MC38 models of this invention, intratrumoral T cells responsive to this p15E neo-antigen could easily be detected (data not shown). Thus, CD28-bispecifics in this MUC16 syngeneic tumor model can boost endogenous TCR/CD3-dependent T cell responses, which can then further be enhanced by providing additional "signal 1" activation via a CD3-bispecific.

It has long been appreciated that T cell activation via the TCR complex ("signal 1") can be markedly enhanced by co-stimulatory signals such as those mediated when the CD28 receptor on T cells engages its ligands (CD80/B7.1 and CD86/B7.2) on target cells ("signal 2") (J. H. Esensten, Y. A. Helou, G. Chopra, A. Weiss, J. A. Bluestone, CD28 Costimulation:From Mechanism to Therapy. *Immunity* 44, 973-988 (2016)). In agreement with our data, the potential for CD28-costimulation to enhance the anti-tumor activity of T cells was first demonstrated by studies in which B7 ligands were over-expressed on tumor cells (R. H. Schwartz, Costimulation of T lymphocytes: the role of CD28, CTLA-4, and B7/BB1 in interleukin-2 production and immunotherapy. Cell 71, 1065-1068 (1992); L. Chen et al., Costimulation of antitumor immunity by the B7 counterreceptor for the T lymphocyte molecules CD28 and CTLA-4. *Cell* 71, 1093-1102 (1992)), which showed improved T cell rejection of such B7-expressing tumors. This potential inspired efforts to evaluate CD28-activating antibodies in human trials. Tragically, the 2006 trial of such an antibody (TGN1412) resulted in life-threatening complications in all six human volunteers (G. Suntharalingam et al., Cytokine storm in a phase 1 trial of the anti-CD28 monoclonal antibody TGN1412. *N Engl J Med* 355, 1018-1028 (2006)), due to multi-organ failure resulting from massive cytokine release syndrome (CRS). This catastrophe led to cessation of any further testing of CD28-activating antibodies in humans.

CD28-bispecific antibodies which would not directly activate CD28, unless clustered on tumor cell surfaces, offered the possibility of promoting co-stimulation only at the tumor site, without the systemic toxicity of conventional CD28-activating antibodies. Initial versions of such CD28-bispecifics were proposed and evaluated in the 1990's (C. Renner et al., Cure of xenografted human tumors by bispecific monoclonal antibodies and human T cells. *Science* 264, 833-835 (1994); G. Jung et al., Local immunotherapy of glioma patients with a combination of 2 bispecific antibody fragments and resting autologous lymphocytes: evidence for in situ t-cell activation and therapeutic efficacy. *Int J Cancer* 91, 225-230 (2001); M. Brandl, L. Grosse-Hovest, E. Holler, H. J. Kolb, G. Jung, Bispecific antibody fragments with CD20 X CD28 specificity allow effective autologous and allogeneic T-cell activation against malignant cells in peripheral blood and bone marrow cultures from patients with B-cell lineage leukemia and lymphoma. *Exp Hematol* 27, 1264-1270 (1999)); however, the early technology available at the time required chemical cross-linking or hybrid/hybridoma fusions to create the proposed biotherapeutics, and resulted in suboptimal reagents which had profound activity on their own independent of their clustering on tumor cells (reminiscent of conventional CD28-antibodies, presumably due to non-specific aggregation of these bispecifics). Moreover, these early approaches also required pre-activation of T cells in vitro, in order to observe any antitumor activity in vivo. Together, the catastrophic clinical results with the TGN1412 CD28-activating antibody, as well as the limitations of these early CD28-bispecific approaches, dissuaded further exploration of these approaches.

Described herein is a novel class of CD28 costimulatory bispecific antibodies that can markedly and safely promote anti-tumor activity by providing a co-stimulatory "signal 2". These CD28-bispecifics have limited activity on their own (in the absence of "signal 1"), but can markedly enhance anti-tumor activity in the setting of "signal 1", as can be provided by pairing these CD28-bispecifics with the emerging class of CD3-bispecifics (or if these CD28-bispecifics are used in settings where there are already endogenous populations of tumor-specific T cells). The generation, testing and success of this new CD28-bispecific approach was dependent on (1) the utilization of a novel bispecific platform that was initially developed to produce CD3-bispecifics and which was recently validated both technologically (E. J. Smith et al., A novel, native-format bispecific antibody triggering T-cell killing of B cells is robustly active in mouse tumor models and cynomolgus monkeys. *Sci Rep* 5, 17943 (2015)) and clinically (A. Crawford et al., REGN4018, a novel MUC16xCD3 bispecific T-cell engager for the treatment of ovarian cancer. *Proceedings of the American Association for Cancer Research Annual Meeting* 2018, (2018)) (Clinicaltrials.gov: NCT02290951, Clinicaltrials.gov: NCT03564340) for these CD3-bispecifics, and which was then adapted so as to efficiently produce CD28-bispecifics that display minimal activity in the absence of a specific "signal 1"; (2) the development of multiple xenogenic and syngeneic genetically-humanized (D. M. Valenzuela et al., High-throughput engineering of the mouse genome coupled with high-resolution expression analysis. *Nat Biotechnol* 21, 652-659 (2003); W. T. Poueymirou et al., F0 generation mice fully derived from gene-targeted embryonic stem cells allowing immediate phenotypic analyses. *Nat Biotechnol* 25, 91-99 (2007)) animal tumor models to assess these CD28-bispecifics on their own and in combination with CD3-bispecifics; and (3) together with a much deeper knowledge of the cytokine release syndrome and its clinical development (A. Shimabukuro-Vornhagen et al., Cytokine release syndrome. *J Immunother Cancer* 6, 56 (2018); D. W. Lee et al., Current concepts in the diagnosis and management of cytokine release syndrome. *Blood* 124, 188-195 (2014); C. L. Bonifant, H. J. Jackson, R. J. Brentjens, K. J. Curran, Toxicity and management in CAR T-cell therapy. *Mol Ther Oncolytics* 3, 16011 (2016)) the validation of a monkey model in which any potential toxicity of these CD28-bispecifics could be compared to that of conventional CD28-activating antibodies.

Described herein are the generation and testing of TSAxCD28 co-stimulatory bispecific antibodies targeted against a TSAs for ovarian cancer (MUC16xCD28). It was shown showed that, in the absence of "signal 1", these CD28-bispecifics have minimal activity, in vitro or in vivo. However, these CD28-bispecifics can be paired with CD3-bispecifics to form artificial "immune synapses" containing the tumor antigens as well as the TCR and CD28 complexes. Moreover, when paired with appropriate CD3-bispecifics in vitro, these CD28-bispecifics can efficiently and specifically promote T cell activation and tumor cell killing in an antigen-dependent manner. Furthermore, these CD28-bispecifics also efficiently enhance the anti-tumor activity of CD3-bispecifics in vivo, in a tumor antigen-specific manner, in xenogenic and syngeneic tumor models; in such models, the CD28-bispecifics have minimal single-agent activity unless tumor-specific T cells are already present, and in such settings they appear to enhance this specific activity in a tumor-antigen-dependent manner. In addition, TSAxCD28 and TSAxCD3 combination therapy significantly drives expansion of an intratumoral activated/memory T cell phenotype in vivo. Finally, toxicology studies in genetically-humanized immunocompetent mice, as well as in cynomolgus monkeys, demonstrate that these bispecifics exhibit limited activity and no toxicity as single agents, as directly compared to conventional CD28-activating antibodies.

Often, the characterization of human-specific clinical candidates in the field of immunooncology is limited to testing in xenogenic tumor models with engrafted human immune cells. Although these xenogenic models (such as the OVCAR3 model utilized) can be very useful, they have limitations. The mice used in such xenogenic models do not express the human tumor target in their normal tissues, thereby precluding assessment of the test agent in the setting of normal tissue expression of the target. Indeed, if a target is normally also expressed at high levels in normal tissues, this could limit anti-tumor efficacy by diverting the test agent from the tumor, and could result in toxicity on these normal tissues—none of this could be assessed in a xenogenic model. An additional limitation could involve the activity of the engrafted human peripheral blood mononuclear cells (PBMCs) transferred to an immunodeficient mouse, which could differ from that of normal host T cells found in a immune-competent system. To overcome these limitations and provide better models for testing human-specific clinical candidates, created double and triple genetically-humanized mice were created. In these models, the tumor antigens were genetically humanized to allow for their normal expression in appropriate host tissues (for MUC16), and the CD3 and/or CD28 components were genetically-humanized to allow immunocompetent host cells to respond to the human-specific clinical candidates. In these genetically-humanized immunocompetent syngeneic animal models, it was found that just as in the xenogenic animal models the CD28-bispecifics for the MUC16 tumor target enhanced the anti-tumor activity of their appropriate CD3-bispecifics. The similar enhancement of anti-tumor efficacy by the different TSAxCD28 bispecifics (e.g., MUC16 and PSMA (data not shown)) across multiple pre-clinical models suggests that this therapeutic modality is robust and not limited to a specific tumor model, and could have broader utility as a novel combination target class for immunotherapy. Overall, the findings highlight that TSAxCD28 bispecifics can synergize with TSAxCD3 bispecifics and may provide a biologic solution that could markedly enhance the efficacy of the well-studied TSAxCD3 bispecifics, in a reasonably safe and well-tolerated manner, justifying testing in human trials.

TSAxCD3 bispecifics represent a promising emerging class of immunotherapy, but further optimization of anti-tumor activity will surely be necessary in many cases. Just as CAR-T approaches have employed chimeric receptors that artificially activate both "signal 1" and "signal 2" so as to improve their anti-tumor activity (E. A. Zhukovsky, R. J. Morse, M. V. Maus, Bispecific antibodies and CARs: generalized immunotherapeutics harnessing T cell redirection. *Curr Opin Immunol* 40, 24-35 (2016); S. L. Maude et al., Tisagenlecleucel in Children and Young Adults with B-Cell Lymphoblastic Leukemia. *N Engl J Med* 378, 439-448 (2018)), it is shown now the potential benefit of combining CD3-specifics (which provide "signal 1") with CD28-bispecifics (which provide "signal 2") to enhance anti-tumor activity. In addition to the practical benefits that such an approach might have over CAR-T therapies—in that it does not require a laborious cell therapy preparation that must be individually customized for each patient, nor does it require that patients be preemptively "lymphodepleted" via toxic chemotherapy so that they can accept this cell therapy often associated with adverse effects (A. Shimabukuro-Vornhagen et al., Cytokine release syndrome. *J Immunother Cancer* 6, 56 (2018); C. H. June, R. S. O'Connor, O. U. Kawalekar, S. Ghassemi, M. C. Milone, CAR T cell immunotherapy for human cancer. *Science* 359, 1361-1365 (2018))—the bispecific approach according to the invention offers the potential for increased efficacy as well as increased safety and specificity of action. That is, it is possible to take advantage of "combinatorial targeting", by pairing a CD3-bispecific for one antigen with a CD28-bispecific specific for a second antigen—increased efficacy will only occur on tumor cells expressing both antigens—thus focusing T cell killing only to tumor cells expressing both antigens, while limiting "off target toxicity" in normal tissues expressing only one of the antigens. Collectively, the data presented herein demonstrate that combining CD28-based bispecifics with CD3-based bispecifics may provide well-tolerated, "off-the-shelf" biologics solutions with markedly enhanced and synergistic anti-tumor activity. Initial testing of this possibility in human trials will occur this year.

Example 9. MUC16xCD28 Alone or in Combination Therapy does not Induce Systemic T Cell Activation in Comparison to CD28 Superagonist in Cynomolgus Monkeys Exemplary MUC16xCD28 antibodies of the invention potentiate MUC16xCD3 activation of T cells from cynomolgus monkeys (FIGS. 2F-2H). To determine the safety and tolerability of exemplary anti-MUC16xCD28 bispecific antibodies of the invention alone or in combination with anti-MUC16xCD3, a single dose toxicity study was performed in cynomolgus monkeys. Female or male cynomolgus monkeys were assigned to treatment groups as indicated in Table 27.

The cynomolgus monkey study was conducted in accordance with IACUC guidelines. Male cynomolgus monkeys (3 animals/group) received a single dose of each test article via intravenous infusion for approximately 30 minutes (combination treatment was administered as separate infusion for total of 1 hour). Assessment of toxicity was based on clinical observations, qualitative food consumption, body weight, neurological examinations, vital signs (body temperature, heart rate, pulse oximetry, and respiration rate), and clinical and anatomic pathology. Blood and tissue samples were collected for cytokine analysis, immunophenotyping analysis, histopathology and toxicokinetic evaluation. CRP levels were analyzed on a Roche Modular P 800 system. Cytokines were measured by Meso Scale Diagnostics (MSD, Rockville, MD). For peripheral blood flow cytometry, blood was collected into potassium EDTA tubes, lysed, stained with anti-CD3, anti-Ki67 and anti-ICOS (BD Biosciences) and analyzed with FACS Canto II.

Animals received a single dose of each test article via intravenous infusion for approximately 30 minutes (combination treatment was administered as separate infusion for total of 1 hour). Assessment of toxicity was based on clinical observations, qualitative food consumption, body weight, neurological examinations, vital signs (body temperature, heart rate, pulse oximetry, and respiration rate), and clinical and anatomic pathology. Blood samples were collected for cytokine analysis, FACS immunophenotyping analysis, and toxicokinetic evaluation. No significant cytokine release, T cell marginalization or T cell activation marker upregulation were observed following single dose administration of exemplary anti-MUC16xCD28 of the invention at 1 or 10 mg/kg, MUC16xCD3 at 1 or 10 mg/kg or combination treatments. Table 27 summarizes different readouts including absolute T cell numbers, T cell activation marker (ki67), CRP and serum cytokine levels from blood obtained at the indicated time point from individual animals. Further, these findings were validated using dry- and wet-coated human T cell proliferation assays, which demonstrated that anchoring MUC16xCD28 to assay plates using a dry-coating or a wet-coating method does not induce T cell activation in the absence of CD3 stimulus in contrast to a CD28 superagonist antibody (FIG. 7). Indeed, it was found that exemplary anti-MUC16xCD28 bispecific antibodies of the invention as well as the parent bivalent CD28 antibodies failed to induce human T cell proliferation in comparison to the CD28 superagonist antibody. Overall, the exploratory single-dose toxicology study in monkeys and in vitro human T cell-based assays suggest that exemplary anti-MUC16xCD28 antibodies of the invention are safe and well tolerated.

TABLE 27

| Molecule | Description | Dose (mg/kg) | Animal # | Day 1 - Clinical Obs. | Any Obs. Days 2-4 | (E3/µL) Pretest | (E3/µL) 5 hr | T-cells Ki67 + (E3/µL) test | T-cells Ki67 + (E3/µL) 72 hr | CRP (mg/dL) 24 hr | IL-6 | IL-8 | IL-10 | IFN-g | TNF-a | IL-2 | IL-4 |
|---|---|---|---|---|---|---|---|---|---|---|---|---|---|---|---|---|---|
| REGN4018 | anti-Muc16 × CD3 (hIgG4) | 1 | 1501 | — | — | 2.28 | 1.67 | 0.11 | 0.10 | 13.8 | 10 | 2 | 3 | BLQ | BLQ | 7 | BLQ |
| | | | 1502 | — | — | 3.12 | 1.71 | 0.25 | 0.29 | 7.9 | 24 | 2 | 4 | BLQ | 4 | BLQ | BLQ |
| | | | 1503 | — | — | 3.84 | 1.58 | 0.21 | 0.17 | 6 | 5 | 2 | BLQ | BLQ | BLQ | 3 | BLQ |
| bs24963D | anti-Muc16 × CD28 (hIgG4) | 1 | 2501 | — | — | 3.07 | 2.40 | 0.13 | 0.20 | 0.4 | 3 | 3 | BLQ | BLQ | 4 | 3 | BLQ |
| | | | 2502 | — | — | 1.97 | 2.73 | 0.10 | 0.15 | 0.1 | 4 | 3 | 3 | BLQ | 4 | 4 | BLQ |
| | | | 2503 | — | — | 1.64 | 3.05 | 0.10 | 0.19 | 0.2 | 7 | 3 | 4 | 46 | 6 | 4 | BLQ |
| REGN4018 + bs24963D | anti-Muc16 × CD3 + anti-Muc16 × CD28 | 1 + 1 | 3501 | — | — | 2.89 | 1.98 | 0.19 | 0.10 | 13.3 | 24 | 3 | 4 | 47 | 4 | 13 | BLQ |
| | | | 3502 | — | — | 1.62 | 1.18 | 0.10 | 0.06 | 13.3 | 22 | 3 | BLQ | 80 | 5 | 7 | BLQ |
| | | | 3503 | — | — | 1.80 | 1.37 | 0.10 | 0.09 | 9.8 | 7 | BLQ | BLQ | BLQ | 4 | 9 | BLQ |
| REGN4018 | anti-Muc16 × CD3 (hIgG4) | 10 | 4501 | — | — | 2.48 | 0.89 | 0.13 | 0.12 | 14.2 | 11 | 4 | 4 | 28 | 4 | 3 | BLQ |
| | | | 4502 | — | — | 1.16 | 0.52 | 0.10 | 0.12 | 7.6 | 7 | 4 | 4 | 31 | BLQ | 6 | BLQ |
| | | | 4503 | — | — | 3.75 | 1.01 | 0.23 | 0.21 | 2.5 | 5 | 4 | 4 | 38 | 4 | 4 | BLQ |
| bs24963D | anti-Muc16 × CD28 (hIgG4) | 10 | 9501 | — | — | 1.86 | 2.91 | 0.09 | 0.17 | 0.1 | 4 | 4 | 4 | BLQ | 5 | 3 | BLQ |
| | | | 9502 | — | — | 0.57 | 0.96 | 0.04 | 0.07 | 0.2 | 9 | 4 | 4 | BLQ | BLQ | 4 | BLQ |
| | | | 9503 | — | — | 1.49 | 2.98 | 0.18 | 0.19 | 0.5 | 7 | 4 | 5 | BLQ | 4 | 3 | BLQ |
| REGN4018 + bs24963D | anti-Muc16 × CD3 + anti-Muc16 × CD28 | 10 + 10 | 6501 | — | — | 3.58 | 0.75 | 0.21 | 0.09 | 14.3 | 31 | 5 | 3 | BLQ | BLQ | 7 | BLQ |
| | | | 6502 | — | — | 3.98 | 1.29 | 0.31 | 0.29 | 14.6 | 73 | 5 | 3 | BLQ | BLQ | 38 | BLQ |
| | | | 6503 | — | — | 2.01 | 0.79 | 0.17 | 0.10 | 5.3 | 7 | 3 | 3 | BLQ | 4 | BLQ | BLQ |
| REGN4018 + bs24963D | anti-Muc16 × CD3 + anti-Muc16 × CD28 | 1 + 10 | 5501 | — | — | 1.70 | 1.37 | 0.14 | 0.23 | 14.2 | 6 | 4 | 4 | 36 | BLQ | 6 | BLQ |
| | | | 5502 | — | — | 3.11 | 3.24 | 0.18 | 0.17 | 5.5 | 7 | 5 | 4 | BLQ | BLQ | 4 | BLQ |
| | | | 5503 | — | — | 2.38 | 1.85 | 0.20 | 0.19 | 6.2 | 31 | 4 | 4 | BLQ | BLQ | 2 | BLQ |
| REGN4018 + bs24963D | anti-Muc16 × CD3 + anti-Muc16 × CD28 | 1 + 1, repeat dosing | 8501 | — | — | 3.36 | 1.04 | 0.26 | 0.05 | 14.4 | 12 | 4 | 4 | BLQ | 3 | 11 | BLQ |
| | | | 8502 | — | — | 2.49 | 2.09 | 0.14 | 0.06 | 11.7 | 9 | 4 | 5 | BLQ | 5 | 7 | BLQ |
| | | | 8503 | — | — | 5.93 | 4.73 | 0.31 | 0.15 | 14.6 | 25 | 4 | 4 | BLQ | 4 | 4 | BLQ |

BLQ: Below the Limit of Quantification
LLOQ (Lower Limit of Quantification):
IFN-g = 37 pg/ml;
TNF-a = 3 pg/ml;
IL-2 = 2.4 pg/ml;
IL-6 = 2 pg/ml;
IL-8 = 1.7 pg/mL;
IL-4 = 1.8 pg/mL;
IL-10 = 3 pg/ml Blood samples were collected for cytokine and flow cytometry immunophenotyping analysis. While CD28-SA administered to monkeys induced significant cytokine release, lymphocyte margination and T cell activation, it was notable that no cytokine release, T cell margination or T cell activation was observed following administration of MUC16xCD28 (FIGS. 8A-8C and Table 27). Overall, these preliminary observations suggest that TSAxCD28 bispecifics are well-tolerated in primates, and do not induce cytokine release and T cell activation as is seen with CD28-SA (data not shown). It should be noted that previous studies with CD28-SA in monkeys failed to predict the profound cyto-kine release and T cell activation seen in humans (Tegenaro A G, www.circare.org/foia5/tgn1412investigator bro-chure.pdf), and this was attributed to lower CD28 expression in monkeys (D. Eastwood et al., Monoclonal antibody TGN1412 trial failure explained by species differences in CD28 expression on CD4+ effector memory T-cells. *Br J Pharmacol* 161, 512-526 (2010)). Although tolerability studies in cynomolgus monkeys might not be predictive of CRS in humans, the strong signals noted with CD28-SA in monkeys suggest that this was missed by Tegenaro et al. simply because they did not examine the appropriate early timepoints when these responses can be robustly observed.

Example 10: Binding of Bs24963D(MUC16 X CD28 Ab, Also Referred to as REGN5668) and REGN4018 (MUC16 X CD3) to Cell Lines Expressing Human or Cynomolgus Monkey MUC16, to Primary Cells from Human or Cynomolgus Monkey PBMC, and a T-Cell Line Materials and Methods—Summary of Experimental Procedures Flow cytometric analysis was utilized to determine binding of bs24963D to human ovarian cancer cell lines (OVCAR-3 and PEO1) endogenously expressing human MUC16, and of bs24963Dand REGN4018 to mouse ID8 cells engineered to express human or cynomolgus MUC16, to 3T3 cells engineered to express human MUC16, to human and cynomolgus monkey T cells, and to the engineered reporter T-cell line.

Briefly, $1\times10^5$ cells/well were incubated for 30 minutes at 4° C. with a serial dilution of antibodies including bs24963D, REGN4018, and control antibodies (IgG4$^{P-PVA}$ non-binding control mAb, CD28 non-bridging control bispecific antibody, or parental CD28 or CD3 controls).

Antibody dilutions ranged from 12.2 pM to 200 nM for human and cynomolgus monkey primary T cells and engineered reporter T cells, whereas 8.1 pM to 133 nM was chosen for MUC16$^+$ target cells.

After incubation, cells were washed twice with cold PBS containing 1% filtered FBS, followed by detection with a phycoerythrin (PE)-labeled anti-human IgG (MUC16$^+$ cells) or Alexa647-labeled anti-human IgG (CD28$^+$ cells).

Near-infrared (IR) reactive LIVE/DEAD dye was added to human and cynomolgus monkey T cells. Wells containing no antibody or secondary antibody only were used as a control.

After incubation with MUC16$^+$ cells or the J.RT3.T3.5/NF-κB-Luc/1G4AB/hCD8ap/hCD28 cell line, cells were washed, re-suspended in 200 μL FACS buffer (cold PBS containing 1% filtered FBS and 1 mM EDTA) and analyzed by flow cytometry on a BD FACS Canto II.

After incubation with human or cynomolgus monkey T cells, cells were washed and stained with a cocktail of anti-CD2, anti-CD16, anti-CD4, and anti-CD8 in FACS buffer for 20 minutes at 4° C. After wash, cells were re-suspended in FACS buffer, and gated on Live/CD2$^+$/CD4$^+$/CD16$^-$ or Live/CD2$^+$/CD8$^+$/CD16$^-$ and analyzed by flow cytometry on a BD LSRFortessa X-20.

For EC$_{50}$ determinations, measured MFI values were analyzed using a four-parameter logistic equation over an 9-point response curve using GraphPad Prism. The fold increase in maximum MFI was determined by taking the ratio of the highest MFI detected to the MFI of wells containing secondary antibody only.

Flow cytometry was also used to determine binding of bs24963D and a commercial anti-PD-L1 antibody to MUC16$^+$ human pancreatic cancer cells, SW1990 and SW1990/hPD-L1 cells. Briefly, $2\times10^5$ cells were incubated with 5 μL (66.7 nM) bs24963D, anti-PD-L1 (2.5 μL), or non-binding control antibody conjugated with AlexaFluor647 (bs24963D) or APC (anti-PD-L1) and incubated on ice for 30 minutes. Cells were washed once with stain buffer, centrifuged, and washed with D-PBS. Cells were stained with 100 μL of 1:1000 dilution of LIVE/DEAD Fixable violet viability dye and incubated for 15 minutes at room temperature. Cells were washed 3 times in staining buffer and resuspended in 100 μL 1:1 staining buffer and cytofix solution and analyzed by flow cytometry using the Cytoflex cytometer. Fold binding over viability was calculated by dividing MFI of antibody of interest over the MFI of viability alone.

Materials and Methods

NF-κB Luciferase Reporter Bioassay

The ability of bs24963D to enhance TCR-mediated signaling was assessed in an engineered T cell/antigen-presenting cell-based reporter assay as shown in FIG. 10. TCRs recognize specific MHC/peptide complexes and activate T cells via numerous transcription factors such as activator protein 1 (AP-1), nuclear factor of activated T cells (NFAT), or nuclear factor kappa-light-chain-enhancer of activated B cells (NF-κB) (Goldrath, 1999; Nature 402:255-62) (Shapiro, 1998; J. Immunology; 161(12):6455-8). The T-cell response is further refined via engagement of co-stimulatory receptors, such as CD28, which is in turn activated by its endogenous ligands, CD80 or CD86, and subsequently potentiates cellular signals, such as pathways controlled by the NF-κB transcription factor, after TCR activation.

In this assay, engineered T cells are directly activated via the 1G4 TCR (IG4AB), which recognizes the NY-ESO-1 157-165 peptide (NYESO1p) in complex with the human MHC class I molecule, HLA-A2, and hβ2M displayed on engineered antigen-presenting 3T3 cells (Robbins, 2008; J. of Immunology; 180(9): 6116-31). TCR activation leads to the production of luciferase, which is driven by the NF-κB transcription factor in the engineered reporter T cells. CD8 facilitates the TCR/MHC interaction and promotes T-cell activation by recruiting the lymphocyte-specific protein tyrosine kinase (Lck) to the TCR/CD3 complex, thereby enhancing TCR signaling through the phosphorylation of intracellular immunoreceptor tyrosine-based activation motifs (ITAMs) (Cole, 2012; Immunology; 137(2):139-48) (Guirado, 2002; Biochem. Biophys. Res. Comm. 291(3): 574-81).

Two-fold serial dilutions of bs24963D, non-bridging control (non-TAAxCD28 bispecific antibody), or a non-binding control (39 pM to 10 nM) were added in duplicate to $5\times10^4$ engineered reporter T cells (J.RT3.T3.5/NF-κB-Luc/1G4AB/hCD8αβ/hCD28) per well in the presence of 1.5× $10^4$ antigen-presenting cells that were either MUC16$^-$ (3T3/hβ2M/HLA-A2/NYESO1p) or MUC16$^+$ (3T3/hβ2M/HLA-A2/NYESO1p/hMUC16). The antibody dilutions and bioassay were performed in complete media (RPMI supplemented with 10% FBS, and a cocktail of penicillin, streptomycin, and L-glutamine). Wells containing no antibody were included as additional controls and used to calculate the fold increase of the activity and EC$_{50}$ values. Plates were incubated at 37° C. and 5% $CO_2$ for 5 hours and then ONE-Glo luciferase substrate (100 μL) was added to each well. The luciferase activity was recorded as a luminescence signal using the ENVISION plate reader expressed as relative light units (RLU). Detected RLU values were analyzed by a 4-parameter logistic equation over a 10-point response curve using GraphPad Prism.

Maximum activation signal was determined as the mean maximum RLU response detected within the tested antibody concentration range. The fold increase in activity was calculated as the ratio of the highest mean RLU value recorded within the tested antibody concentration range over the mean RLU value recorded in the absence of the antibody. T-Cell Activation Assays for T-Cell Proliferation and IL-2 Release The capacity of bs24963D to mediate IL-2 release and T-cell proliferation in the presence of a constant concentration of REGN4018 (assessed in human ovarian cancer cell lines OVCAR-3 and PEO1) or in the presence of a constant concentration of cemiplimab (assessed in human pancreatic cancer cell lines [SW1990 and SW1990/hPD-L1]) was determined using T-cell activation assays with enriched human primary T cells from 3 or 2 donors, respectively.

Human Primary T Cell Isolation

Human PBMC were isolated from 4 healthy donor leukocyte packs. For donors 555014 and 555109, PBMC were isolated from peripheral blood using density gradient centrifugation. Briefly, 15 mL of Ficoll Plaque Plus was added to 50 mL conical tubes and subsequently 30 mL of blood diluted 1:1 with PBS containing 2% FBS was layered on top. After a 30-minute centrifugation at 400×g, with the brake off, the mononuclear cell layer was transferred to a fresh tube, diluted 5× with PBS containing 2% FBS and centrifuged for 8 minutes at 300×g. For donors 555131 and 555129, PBMC were isolated from peripheral blood from a healthy donor using EasySep Direct Human PBMC Isolation Kit from Stem Cell Technologies and following the manufacturers protocol. Isolated PBMC were frozen in FBS containing 10% DMSO. For CD3$^+$ T-cell isolation, frozen vials of PBMC were thawed in a 37° C. water bath and diluted in stimulation media (X-VIVO 15 cell culture media supplemented with 10% FBS, HEPES, NaPyr, NEAA, and 0.01 mM β-mercaptoethanol [BME]) containing 50 U/mL Benzonase® Nuclease. Cells were centrifuged at 1200 rpm for 10 minutes, resuspended in EasySep buffer and isolated using StemCell Technologies EasySep T-Cell Isolation kit following the manufacturer's protocol.

T-Cell Activation Assay with Human OVCAR-3, PEO1, SW1990, SW1990/hPD-L1 Cells and Human Primary T Cells CD3$^+$ T cells, resuspended in stimulation media (X-VIVO 15 cell culture media supplemented with 10% FBS, HEPES, NaPyr, NEAA, and 0.01 mM BME), were plated out into 96-well round bottom plates at a concentration of 1×10$^5$ cells/well. OVCAR-3, PEO1, SW1990, or SW1990/hPD-L1 cells were treated with 25 μg/mL (OVCAR-3), 10 μg/mL (PEO1), or 30 μg/mL (SW1990 and SW1990/hPD-L1) mitomycin C to arrest proliferation. After incubation for 1 hour at 37° C., 5% CO$_2$, mitomycin C-treated cells were washed 3 times with D-PBS containing 2% FBS, followed by a final resuspension in stimulation media. OVCAR-3, PEO1, SW1990, and SW1990/hPD-L1 cells were added to wells containing CD3$^+$ T cells at a final concentration of 1×10$^4$, 2.5×10$^4$ cells, or 5×10$^4$ cells respectively for OVCAR-3, PEO1, and both SW1990 cells. A constant concentration of REGN4018 or CD3 non-bridging control bispecific antibody (5 nM), or cemiplimab or non-binding IgG4$^P$ control (20 nM), was added to wells containing OVCAR-3, PEO1, SW1990, or SW1990/hPD-L1 cells. Subsequently, bs24963D, non-TAAxCD28 control, or non-binding control, antibodies were titrated from 7.6 pM to 500 nM in a 1:4 dilution series and added to wells. The final point of the 10-point concentration curve contained no antibody and was used to calculate the fold increase of activity. After incubating plates for 72 (OVCAR-3 and PEO1) or 96 (SW1990 and SW1990/hPD-L1) hours at 37° C., 5% CO$_2$, 50 μL of media supernatant was collected to measure IL-2 release in advance of treatment with [Methyl-$^3$H]-Thymidine to quantify proliferation.

For IL-2 release, 5 μL (for assays using OVCAR-3 and PEO1 cells) or 20 μL (for assays using SW1990 and SW1990/hPD-L1 cells) of supernatant was tested using the human IL-2 AlphaLISA kit according the manufacturer's protocol. The IL-2 measurements were acquired on Perkin Elmer's multilabel plate reader Envision and reported as Relative Fluorescence Units (RFU).

For proliferation assays, 50 μL of [Methyl-$^3$H]-Thymidine diluted to 2 mCi/mL in stimulation media was added to wells and the plates were incubated for either 6 hours (for assays using OVCAR-3 and PEO1 cells) or 16 hours (for assays using SW1990 and SW1990/hPD-L1 cells). [Methyl-$^3$H]-Thymidine will be incorporated at higher amounts in dividing cells. After the incubation, cells were harvested onto filter plates and prepared for the measurement on the Microplate Scintillation & Luminescence Counter Top-Count NXT instrument.

All serial dilutions were tested in triplicate for IL-2 release and proliferation. The EC$_{50}$ values for the antibodies were determined from a 4-parameter logistic equation over a 10-point dose-response curve using GraphPad Prism™ software. Maximal levels of IL-2 release and proliferation are given as the mean maximal response detected within the tested dose range. Fold increase of maximum IL-2 release or T-cell proliferation mediated by bs24963D was calculated relative to the maximum IL-2 release or proliferation mediated by no antibody.

The ability of bs24963D to activate T cells was evaluated in an assay in which stimulatory antigen-presenting cells provide signal 1. This assay used J.RT3.T3.5 reporter T cells engineered to express human CD8, human CD28, a literature-described TCR (1G4) that recognizes an NY-ESO-1 peptide (NYESO1p) in complex with HLA-A2, and an NF-κB-Luciferase reporter. The stimulatory antigen-presenting cells providing signal 1 were 3T3 cells engineered to express HLA-A2, hβ2M, and NYESO1p with or without human MUC16 (hMUC16). A CD28 non-bridging control bispecific antibody (non-TAAxCD28) and a non-binding control mAb (IgG4$^{P-PVA}$) were tested in parallel with bs24963D. NF-κB signaling was measured using a luminescent reagent to detect luciferase reporter activity. Results are summarized in Table 28.

In this test system, bs24963D mediated a concentration-dependent increase in NF-κB signaling in the reporter T cells in the presence of the MUC16$^+$ antigen presenting cells; no activity was seen using cells lacking MUC16 expression (FIGS. 11A and 11B). No increase in NF-κB signaling was observed with the CD28 non-bridging control bispecific antibody.

TABLE 28

Summary of bs24963D-Mediated NF-KB-Luciferase Activation

| | Antigen Presenting Cells (+/−MUC16) | | | | | |
| | 3T3/hβ2M/HLA-A2/NYESO1p/hMUC16 | | | 3T3/hβ2M/HLA-A2/NYESO1p | | |
| Antibody | EC$_{50}$ (M) | Max RLU $^a$ | Fold Increase | EC$_{50}$ (M) | Max RLU $^a$ | Fold Increase |
|---|---|---|---|---|---|---|
| bs24963D | 2.88 × 10$^{-10}$ | 254,300 | 2.11 | ND | 65,920 | 1.00 |
| Non-TAAxCD28 | ND | 133,220 | 1.24 | ND | 64,740 | 1.02 |

$^a$ The maximum RLU is the highest mean RLU value observed within the tested antibody concentration range (39 pM to 10 nM).
$^b$ Fold increase of maximum RLU mediated by bs24963D or non-TAAxCD28 was calculated relative to the maximum RLU mediated by no antibody.
Abbreviations: ND, not determined because a concentration-dependent increase in luciferase activity was not observed Example 11. Assessment of Bs24963D (Anti-MUC16 X Anti-CD28)-Mediated IL-2 Release and Proliferation of Human Primary T Cells in the Presence or Absence of REGN4018 (Anti-MUC16 X Anti-CD3) or Cemiplimab (a PD-1 Antagonist Antibody)

The ability of bs24963D to activate human primary T cells, as determined by IL-2 release and T-cell proliferation, was evaluated in the presence of 2 different MUC16⁺ human ovarian cancer cell lines (OVCAR-3 and PEO1). As these cells do not provide sufficient signal 1 from an allogeneic response, a fixed concentration of REGN4018 (a MUC16 X CD3 bispecific antibody) was included to provide signal 1. Results for OVCAR-3 and PEO1 cells are summarized in Table 29 for IL-2 release and in Table 30 for proliferation.

The ability of bs24963D to activate human primary T cells, as determined by IL-2 release and T-cell proliferation, was evaluated in the presence of a MUC16⁺ human pancreatic cancer cell line (SW1990) and SW1990 engineered to overexpress human PD-L1 (SW1990/hPD-L1). Both cell lines provide an allogeneic response that is sufficient to serve as signal 1. In addition, the ability of fixed concentrations of cemiplimab (20 nM) to augment the effects of bs24963D was also assessed. Results for SW1990 and SW1990/hPD-L1 cells are summarized in Table 31 for IL-2 release and Table 32 for proliferation.

Ability of Bs24963D (REGN5668) to Enhance IL-2 Release from and Proliferation of Human Primary T Cells in the Presence or Absence of REGN4018 with OVCAR-3 and PEO1 Target Cells When incubated with OVCAR-3 and PEO1 cancer cells, bs24963D mediated concentration-dependent enhancement of IL-2 release from (FIG. 12) and proliferation of (FIG. 13) human T cells only in the presence of REGN4018. The CD3 and CD28 non-bridging control bispecific antibodies did not enhance IL-2 release in either the presence or absence of REGN4018.

In this assay, 5 nM REGN4018 alone did not increase IL-2 release but showed a moderate enhancement of T-cell proliferation relative to non-binding control.

TABLE 29

Summary of bs24963D-Mediated Enhancement of IL-2 Release from Human Primary T Cells in the Presence or Absence of REGN4018 with OVCAR-3 and PEO1 Target Cells

| Target Cell Line | Donor | Ab at Fixed Concentration (5 nM) | Antibody Tested at Varying Concentrations (7.6 pM to 500 nM) | $EC_{50}$ (M) | Max IL-2[a] (RFU) | Fold Increase[b] (IL-2) |
|---|---|---|---|---|---|---|
| OVCAR-3 | Donor 555014 | REGN4018 | bs24963D | $7.07 \times 10^{-10}$ | 46,931 | 20.01 |
| | | | Non-TAAxCD28 | NC | 4,741 | 1.89 |
| | | Non-TAAxCD3 | bs24963D | NC | 1,361 | 2.75 |
| | | | Non-TAAxCD28 | NC | 3,033 | 6.62 |
| | Donor 555109 | REGN4018 | bs24963D | $1.22 \times 10^{-9}$ | 36,725 | 32.10 |
| | | | Non-TAAxCD28 | NC | 1,638 | 1.38 |
| | | Non-TAAxCD3 | bs24963D | ND | 893 | 1.82 |
| | | | Non-TAAxCD28 | NC | 1,403 | 2.84 |
| | Donor 555131 | REGN4018 | bs24963D | $5.90 \times 10^{-10}$ | 46,209 | 13.08 |
| | | | Non-TAAxCD28 | NC | 4,443 | 1.33 |
| | | Non-TAAxCD3 | bs24963D | NC | 1,814 | 2.71 |
| | | | Non-TAAxCD28 | NC | 3,136 | 5.95 |
| PEO1 | Donor 555014 | REGN4018 | bs24963D | $1.95 \times 10^{-9}$ | 31024 | 30.30 |
| | | | Non-TAAxCD28 | NC | 2312 | 2.16 |
| | | Non-TAAxCD3 | bs24963D | NC | 2490 | 5.56 |
| | | | Non-TAAxCD28 | NC | 2776 | 6.12 |
| | Donor 555109 | REGN4018 | bs24963D | $3.10 \times 10^{-9}$ | 16,421 | 20.03 |
| | | | Non-TAAxCD28 | ND | 897 | 1.33 |
| | | Non-TAAxCD3 | bs24963D | NC | 2,039 | 4.36 |
| | | | Non-TAAxCD28 | NC | 1,360 | 2.35 |
| | Donor 555014 | REGN4018 | bs24963D | $2.42 \times 10^{-10}$ | 29,217 | 25.70 |
| | | | Non-TAAxCD28 | NC | 2,175 | 1.82 |
| | | Non-TAAxCD3 | bs24963D | NC | 2,911 | 5.77 |
| | | | Non-TAAxCD28 | NC | 2,443 | 4.42 |

[a]The maximum IL-2 concentration is the highest mean IL-2 concentration value recorded within the tested antibody concentration range.
[b]Fold increase of maximum IL-2 release mediated by bs24963D, in the presence or absence of REGN4018, was calculated relative to the maximum IL-2 release mediated by no antibody.
Abbreviations:
NC, Not calculated because the data did not fit a 4-parameter logistic equation, not determined because a concentration-dependent increase in IL-2 release was not observed.

TABLE 30

Summary of bs24963D-Mediated Enhancement of Proliferation from Human
Primary T Cells in the Presence or Absence of REGN4018 with OVCAR-3 and PEO1
Target Cells

| Target Cell Line | Donor | Ab at Fixed Concentration (5 nM) | Antibody Tested at Varying Concentrations (7.6 pM to 500 nM) | T-Cell Proliferation | | |
|---|---|---|---|---|---|---|
| | | | | EC$_{50}$ (M) | Max Proliferation[a] (CPM) | Fold Increase[b] (Proliferation) |
| OVCAR-3 | Donor 555014 | REGN4018 | bs24963D | $8.89 \times 10^{-11}$ | 13,968 | 2.03 |
| | | | Non-TAAxCD28 | NC | 11,260 | 1.59 |
| | | Non-TAAxCD3 | bs24963D | NC | 336 | 1.38 |
| | | | Non-TAAxCD28 | NC | 579 | 1.60 |
| | Donor 555109 | REGN4018 | bs24963D | $9.45 \times 10^{-11}$ | 14,818 | 3.18 |
| | | | Non-TAAxCD28 | $4.61 \times 10^{-8}$ | 8,141 | 1.66 |
| | | Non-TAAxCD3 | bs24963D | ND | 416 | 1.37 |
| | | | Non-TAAxCD28 | ND | 475 | 1.33 |
| | Donor 555131 | REGN4018 | bs24963D | $2.47 \times 10^{-11}$ | 13,607 | 1.66 |
| | | | Non-TAAxCD28 | NC | 10,154 | 1.16 |
| | | Non-TAAxCD3 | bs24963D | NC | 622 | 1.82 |
| | | | Non-TAAxCD28 | NC | 562 | 1.68 |
| PEO1 | Donor 555014 | REGN4018 | bs24963D | $1.73 \times 10^{-10}$ | 9,605 | 3.27 |
| | | | Non-TAAxCD28 | NC | 6,953 | 2.26 |
| | | Non-TAAxCD3 | bs24963D | NC | 603 | 2.58 |
| | | | Non-TAAxCD28 | NC | 551 | 3.09 |
| | Donor 555109 | REGN4018 | bs24963D | $4.04 \times 10^{-10}$ | 10,304 | 8.42 |
| | | | Non-TAAxCD28 | NC | 4,888 | 4.62 |
| | | Non-TAAxCD3 | bs24963D | NC | 733 | 2.84 |
| | | | Non-TAAxCD28 | NC | 419 | 1.72 |
| | Donor 555014 | REGN4018 | bs24963D | $2.22 \times 10^{-10}$ | 10,335 | 3.69 |
| | | | Non-TAAxCD28 | $4.22 \times 10^{-8}$ | 5,631 | 2.06 |
| | | Non-TAAxCD3 | bs24963D | NC | 835 | 4.44 |
| | | | Non-TAAxCD28 | NC | 523 | 2.29 |

[a]The maximum proliferation is the highest mean CPM value recorded within the tested antibody concentration range.
[b]Fold increase of maximum T-cell proliferation mediated by bs24963D, in the presence or absence of REGN4018, was calculated relative to the maximum proliferation mediated in the absence of bs24963D or non-TAAxCD28 control.
Abbreviations:
NC, Not calculated because the data did not fit a 4-parameter logistic equation;
ND, not determined because a concentration-dependent increase in proliferation was not observed Ability of Bs249630 (REGN5668) to Enhance IL-2 Release from and Proliferation of Human Primary T Cells in the Presence or Absence of Cemiplimab with SW1990 and SW1990/hPD-L1 Target Cells When incubated with SW1990 and SW1990/hPD-L1 MUC16$^+$ human pancreatic cancer cells, bs24963b mediated concentration-dependent enhancement of IL-2 release from (FIG. 14) and proliferation of (FIG. 15) human T cells in the presence and absence of cemiplimab. Overexpression of human PD-L1 in SW990 cells suppressed IL-2 and T-cell proliferation in the presence of bs24963D and these were modestly increased by the addition of cemiplimab. At high concentrations, the 0028 non-bridging control bispecific antibody mediated some IL-2 release in the presence of SW1990 and SW1990/hPD-L1 cells. In the absence of bs24963D, cemiplimab did not increase IL-2 release or T-cell proliferation relative to 0028 non-bridging control bispecific antibody.

TABLE 31

Summary of bs24963D-Mediated Enhancement of IL-2 Release from Human
Primary T Cells in the Presence or Absence of Cemiplimab with SW1990 and
SW1990/hPD-L1 Target Cells

| Target Cell Line | Donor | Ab at Fixed Concentration (20 nM) | Antibody Tested at Varying Concentrations (7.6 pM to 500 nM) | IL-2 Release from Human Primary T Cells | | |
|---|---|---|---|---|---|---|
| | | | | EC$_{50}$ (M) | Max IL-2[a] (RFU) | Fold Increase[b] (IL-2) |
| SW1990 | Donor 555109 | cemiplimab | bs24963D | $2.98 \times 10^{-9}$ | 3,773 | 3.31 |
| | | | Non-TAAxCD28 | ND | 1,415 | 1.98 |
| | | IgG4$^P$ control | bs24963D | $2.31 \times 10^{-9}$ | 2,922 | 4.83 |
| | | | Non-TAAxCD28 | ND | 944 | 1.31 |

TABLE 31-continued

Summary of bs24963D-Mediated Enhancement of IL-2 Release from Human
Primary T Cells in the Presence or Absence of Cemiplimab with SW1990 and
SW1990/hPD-L1 Target Cells

| Target Cell Line | Donor | Ab at Fixed Concentration (20 nM) | Antibody Tested at Varying Concentrations (7.6 pM to 500 nM) | IL-2 Release from Human Primary T Cells | | |
|---|---|---|---|---|---|---|
| | | | | $EC_{50}$ (M) | Max IL-2[a] (RFU) | Fold Increase[b] (IL-2) |
| | Donor 555129 | cemiplimab | bs24963D | $8.60 \times 10^{-10}$ | 4,833 | 3.39 |
| | | | Non-TAAxCD28 | NC | 2,927 | 2.28 |
| | | IgG4[P] control | bs24963D | $1.21 \times 10^{-9}$ | 3,589 | 2.89 |
| | | | Non-TAAxCD28 | NC | 2,027 | 1.51 |
| SW1990/hPD-L1 | Donor 555109 | cemiplimab | bs24963D | $1.01 \times 10^{-9}$ | 1,692 | 2.73 |
| | | | Non-TAAxCD28 | NC | 1,102 | 1.60 |
| | | IgG4[P] control | bs24963D | $2.55 \times 10^{-9}$ | 1,053 | 1.70 |
| | | | Non-TAAxCD28 | ND | 616 | 1.23 |
| | Donor 555129 | cemiplimab | bs24963D | $1.41 \times 10^{-9}$ | 3,391 | 2.33 |
| | | | Non-TAAxCD28 | NC | 1,977 | 1.57 |
| | | IgG4[P] control | bs24963D | $2.22 \times 10^{-9}$ | 2,161 | 2.14 |
| | | | Non-TAAxCD28 | ND | 1,459 | 1.49 |

[a]The maximum IL-2 concentration is the highest mean IL-2 concentration value recorded within the tested antibody concentration range.
[b]Fold increase of maximum IL-2 release mediated by bs24963D, in the presence or absence of cemiplimab, was calculated relative to the maximum IL-2 release mediated by no antibody.
Abbreviations:
NC, not calculated because the data did not fit a 4-parameter logistic equation;
ND, not determined because a concentration-dependent increase in IL-2 release was not observed

TABLE 32

Summary of bs24963D-Mediated Enhancement of Proliferation from Human
Primary T Cells in the Presence or Absence of Cemiplimab with SW1990 and
SW1990/hPD-L1 Target Cells

| Target Cell Line | Donor | Ab at Fixed Concentration (20 nM) | Antibody Tested at Varying Concentrations (7.6 pM to 500 nM) | T-Cell Proliferation | | |
|---|---|---|---|---|---|---|
| | | | | $EC_{50}$ (M) | Max Proliferation[a] (CPM) | Fold Increase[b] (Proliferation) |
| SW1990 | Donor 555109 | cemiplimab | bs24963D | $1.68 \times 10^{-9}$ | 557 | 4.52 |
| | | | Non-TAAxCD28 | ND | 161 | 1.41 |
| | | IgG4[P] control | bs24963D | $2.86 \times 10^{-9}$ | 421 | 4.36 |
| | | | Non-TAAxCD28 | ND | 123 | 1.46 |
| | Donor 555129 | cemiplimab | bs24963D | $4.59 \times 10^{-10}$ | 545 | 2.47 |
| | | | Non-TAAxCD28 | ND | 279 | 1.66 |
| | | IgG4[P] control | bs24963D | $4.83 \times 10^{-10}$ | 569 | 2.17 |
| | | | Non-TAAxCD28 | ND | 353 | 1.46 |
| SW1990/hPD-L1 | Donor 555109 | cemiplimab | bs24963D | $1.40 \times 10^{-9}$ | 279 | 4.70 |
| | | | Non-TAAxCD28 | ND | 151 | 1.98 |
| | | IgG4[P] control | bs24963D | $1.54 \times 10^{-9}$ | 140 | 2.35 |
| | | | Non-TAAxCD28 | ND | 84.0 | 1.42 |
| | Donor 555129 | cemiplimab | bs24963D | $2.53 \times 10^{-9}$ | 601 | 3.20 |
| | | | Non-TAAxCD28 | NC | 222 | 1.73 |
| | | IgG4[P] control | bs24963D | $1.66 \times 10^{-9}$ | 333 | 2.74 |
| | | | Non-TAAxCD28 | ND | 146 | 1.62 |

[a]The maximum proliferation is the highest mean CPM value recorded within the tested antibody concentration range.
[b]Fold increase of maximum T-cell proliferation mediated by bs24963D, in the presence or absence of cemiplimab, was calculated relative to the maximum proliferation mediated in the absence of bs24963D or non-TAAxCD28 control.
Abbreviations:
NC, not calculated because the data did not fit a 4-parameter logistic equation;
ND, not determined because a concentration-dependent increase in proliferation was not observed The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

| SEQ ID NO: | Sequence |
|---|---|
| 13 | ggtgcatcc |
| 14 | GAS |
| 37 | gctgcatcc |
| 38 | AAS |

5

What is claimed is:

1. A group of nucleic acid molecules encoding a bispecific antigen-binding molecule that binds human CD28 and human MUC16, wherein the group of nucleic acid molecules comprises:

(a) a first nucleic acid molecule encoding a heavy chain variable region (HCVR) comprising HCDR1, HCDR2, HCDR3 domains, respectively, wherein the first nucleic acid molecule comprises the nucleotide sequences of SEQ ID NOs: 19, 21, and 23;

(b) a second nucleic acid molecule encoding a HCVR comprising HCDR1, HCDR2, HCDR3 domains, respectively, wherein the second nucleic acid molecule comprises the nucleotide sequences of SEQ ID NOs: 3, 5 and 7; and (c) a third nucleic acid molecule encoding a light chain variable region (LCVR) comprising LCDR1, LCDR2, LCDR3 domains, respectively, wherein the third nucleic acid molecule comprises the nucleotide sequences of SEQ ID NOs: 11, 13 and 15.

2. The group of nucleic acid molecules of claim 1, wherein:

(a) the first nucleic acid molecule encodes a HCVR and comprises the nucleotide sequence of SEQ ID NO: 17;

(b) the second nucleic acid molecule encodes a HCVR and comprises the nucleotide sequence of SEQ ID NO: 1; and (c) the third nucleic acid molecule encodes a LCVR and comprises the nucleotide sequence of SEQ ID NO: 9.

3. The group of nucleic acid molecules of claim 1, wherein the bispecific antigen-binding molecule is a bispecific antibody, the first nucleic acid molecule encodes a first heavy chain, the second nucleic acid molecule encodes a second heavy chain, and the third nucleic acid molecule encodes a light chain.

4. The group of nucleic acid molecules of claim 3, wherein the first heavy chain or the second heavy chain, but not both, comprises a CH3 domain comprising a H435R (EU numbering) modification and a Y436F (EU numbering) modification.

5. The group of nucleic acid molecules of claim 3, wherein the first heavy chain, the second heavy chain, or both the first and second heavy chains comprise a human IgG1 heavy chain constant region.

6. The group of nucleic acid molecules of claim 3, wherein the first heavy chain, the second heavy chain, or both the first and second heavy chains comprise a human IgG4 heavy chain constant region.

7. An expression vector comprising the group of nucleic acid molecules of claim 1, or a group of expression vectors comprising, respectively, the group of nucleic acid molecules of claim 1.

8. An isolated host cell comprising the expression vector or the group of expression vectors of claim 7.

9. An isolated host cell comprising the group of nucleic acid molecules of claim 1.

10. An isolated host cell comprising the group of nucleic acid molecules of claim 2.

11. A method of producing a bispecific antigen-binding molecule that binds human CD28 and human MUC16, comprising culturing the host cell of claim 8 under conditions permitting production of the bispecific antigen-binding molecule, and recovering the bispecific antigen-binding molecule so produced.

12. The method of claim 11, further comprising formulating the bispecific antigen-binding molecule as a pharmaceutical composition with a suitable carrier.

13. An expression vector comprising the group of nucleic acid molecules of claim 2, or a group of expression vectors comprising, respectively, the group of nucleic acid molecules of claim 2.

14. A group of nucleic acid molecules encoding a bispecific antigen-binding molecule that binds human CD28 and human MUC16, wherein the group of nucleic acid molecules comprises:

(a) a first nucleic acid molecule encoding a heavy chain variable region (HCVR) comprising HCDR1, HCDR2, HCDR3 domains, respectively, comprising the amino acid sequences of SEQ ID NOs: 20, 22 and 24;

(b) a second nucleic acid molecule encoding a HCVR comprising HCDR1, HCDR2, HCDR3 domains, respectively, comprising the amino acid sequences of SEQ ID NOs: 4, 6 and 8; and (c) a third nucleic acid molecule encoding a light chain variable region (LCVR) comprising LCDR1, LCDR2, LCDR3 domains, respectively, comprising the amino acid sequences of SEQ ID NOs: 12, 14 and 16.

15. The group of nucleic acid molecules of claim 14, wherein:

(a) the first nucleic acid molecule encodes a HCVR comprising the amino acid sequence of SEQ ID NO: 18;

(b) the second nucleic acid molecule encodes a HCVR comprising the amino acid sequence of SEQ ID NO: 2; and (c) the third nucleic acid molecule encodes a LCVR comprising the amino acid sequence of SEQ ID NO: 10.

16. The group of nucleic acid molecules of claim 14, wherein the bispecific antigen-binding molecule is a bispecific antibody, the first nucleic acid molecule encodes a first heavy chain, the second nucleic acid molecule encodes a second heavy chain, and the third nucleic acid molecule encodes a light chain.

17. The group of nucleic acid molecules of claim 16, wherein the first heavy chain or the second heavy chain, but not both, comprises a CH3 domain comprising a H435R (EU numbering) modification and a Y436F (EU numbering) modification.

18. The group of nucleic acid molecules of claim 16, wherein the first heavy chain and the second heavy chain comprise a human IgG1 heavy chain constant region.

19. The group of nucleic acid molecules of claim 16, wherein the first heavy chain and the second heavy chain comprise a human IgG4 heavy chain constant region.

20. An expression vector comprising the group of nucleic acid molecules of claim 14, or a group of expression vectors comprising, respectively, the group of nucleic acid molecules of claim 14.

21. An expression vector comprising the group of nucleic acid molecules of claim 15, or a group of expression vectors comprising, respectively, the group of nucleic acid molecules of claim 15.

22. An isolated host cell comprising the expression vector or the group of expression vectors of claim 20.

23. An isolated host cell comprising the group of nucleic acid molecules of claim 14.

24. An isolated host cell comprising the group of nucleic acid molecules of claim 15.

25. A method of producing a bispecific antigen-binding molecule that binds human CD28 and human MUC16, comprising culturing the host cell of claim 22 under conditions permitting production of the bispecific antigen-binding molecule, and recovering the bispecific antigen-binding molecule so produced.

26. The method of claim 25, further comprising formulating the bispecific antigen-binding molecule as a pharmaceutical composition with a suitable carrier.

* * * * *